(12) United States Patent
Zheng et al.

(10) Patent No.: US 8,383,424 B2
(45) Date of Patent: Feb. 26, 2013

(54) METHODS FOR DETECTION OF CYCLOSPORIN A

(75) Inventors: Yi Feng Zheng, Wilmington, DE (US); Deb K. Vickery, Landenberg, PA (US); Susan C. Swann, Antioch, IL (US)

(73) Assignee: Siemens Healthcare Diagnostics, Tarrytown, NY (US)

( * ) Notice: Subject to any disclaimer, the term of this patent is extended or adjusted under 35 U.S.C. 154(b) by 0 days.

(21) Appl. No.: 13/095,506

(22) Filed: Apr. 27, 2011

(65) Prior Publication Data

US 2011/0230638 A1    Sep. 22, 2011

Related U.S. Application Data

(62) Division of application No. 11/968,349, filed on Jan. 2, 2008, now abandoned.

(51) Int. Cl.
*G01N 33/546* (2006.01)
(52) U.S. Cl. .......................................... 436/534; 514/1.1
(58) Field of Classification Search .................. None
See application file for complete search history.

(56) References Cited

U.S. PATENT DOCUMENTS

| | | | |
|---|---|---|---|
| 5,332,679 A | 7/1994 | Simons et al. |
| 5,484,701 A | 1/1996 | Cocuzza et al. |
| 5,504,091 A | 4/1996 | Molnar-Kimber |
| 5,750,413 A | 5/1998 | Morrison et al. |
| 5,876,935 A | 3/1999 | Pankratz et al. |
| 5,914,241 A | 6/1999 | Valkirs |
| 5,972,630 A | 10/1999 | Cromer et al. |
| 6,153,442 A * | 11/2000 | Pirio et al. |
| 6,187,547 B1 | 2/2001 | Legay et al. |
| 6,190,873 B1 * | 2/2001 | Davalian et al. |
| 6,207,398 B1 | 3/2001 | Wang |
| 6,410,340 B1 | 6/2002 | Soldin |
| 6,410,696 B1 | 6/2002 | Davalian et al. |
| 6,713,266 B1 | 3/2004 | Yatscoff et al. |
| 6,881,536 B1 | 4/2005 | Shah et al. |
| 7,090,993 B2 | 8/2006 | Brady et al. |
| 7,105,311 B2 | 9/2006 | Kovalenko |
| 2004/0175696 A1 | 9/2004 | Ullman et al. |
| 2006/0036075 A1 | 2/2006 | Hudson et al. |
| 2006/0246518 A1 | 11/2006 | Chen et al. |

OTHER PUBLICATIONS

NCI Drug Dictionary Jun. 16, 2012.*
Ullman et al., 1996. Luminescent Oxygen Channeling Assay (LOCI TM): Sensitive, Broadly Applicable Homogeneous Immunoassay Method. Clinical Chemistry 42: pp. 1518-1526.

* cited by examiner

*Primary Examiner* — Cecilia J Tsang
*Assistant Examiner* — Li Lee
(74) *Attorney, Agent, or Firm* — Theodore J. Leitereg

(57) ABSTRACT

Methods and reagents are disclosed for determining the presence and/or amount of cyclosporin A in a medium suspected of containing cyclosporin A. In the method a combination is provided in a medium. The combination comprises (i) the sample, (ii) a first member of a signal producing system (sps) associated with a first support wherein the first sps member is capable of activating a second member of the sps and wherein the first support is associated with a first member of a specific binding pair, and (iii) the second sps member associated with a second support wherein the second sps member is activatable by the first sps member. The second support comprises either (I) cyclosporin C or cyclosporin A and the combination further comprises a conjugate of an antibody for cyclosporin A and a second member of the specific binding pair or (II) antibody for cyclosporin A and the combination further comprises a conjugate of cyclosporin A and a second member of the specific binding pair. The combination is subjected to conditions for binding of cyclosporin A to the antibody for cyclosporin A. The first sps member is activated and the amount of signal generated by the second sps member is detected. The amount of signal is related to the presence and/or amount of cyclosporin A in the sample.

2 Claims, 36 Drawing Sheets

Figure 1. Structures of CsA and CsC
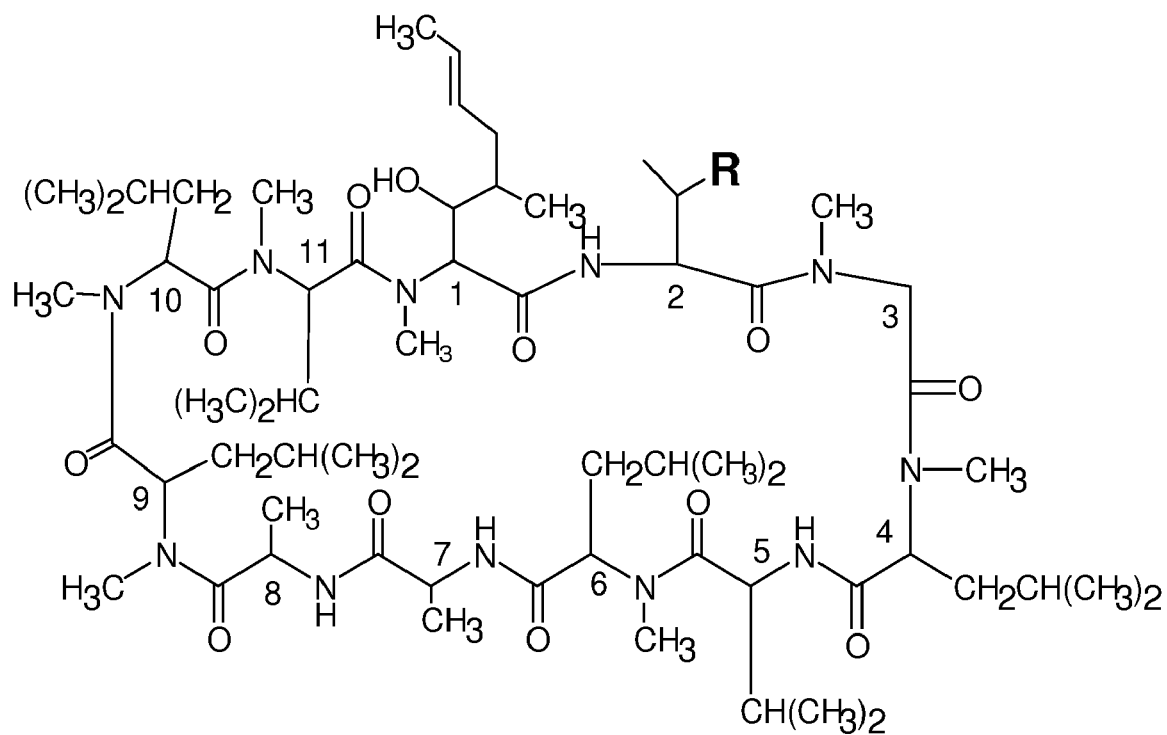
Cyclosporine A (CsA) : R = H (1);
Cyclosporine C (CsC) : R = OH (2);

Figure 2A. CsC-DA-10-EPRM Chemibeads
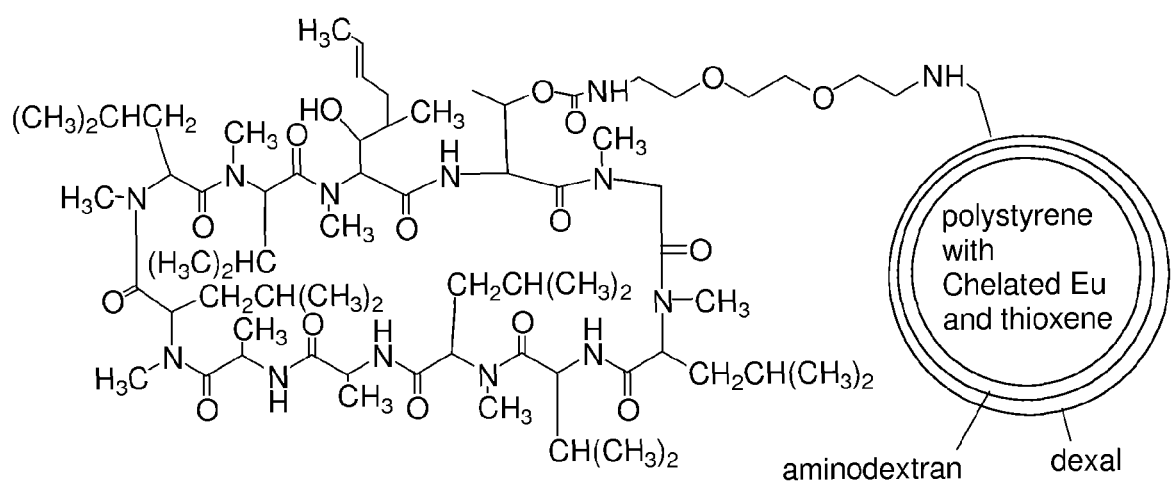
CsC-DA-10-EPRM Bead (4)

Figure 2B. CsC-DA-10-HG-APRM Chemibeads
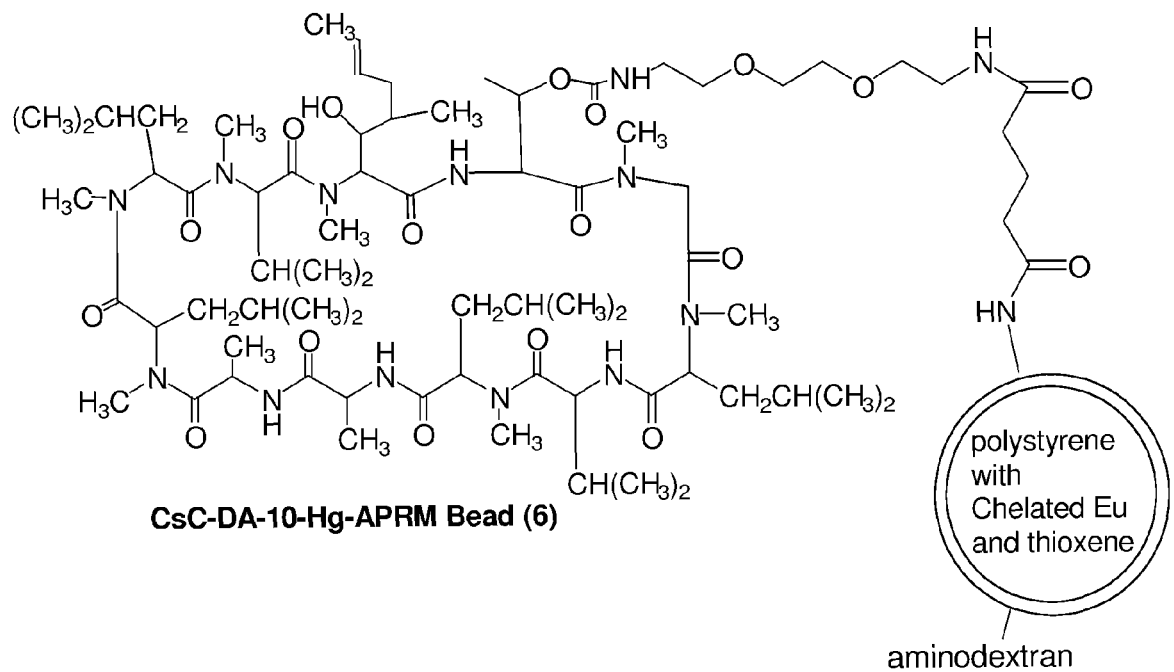

Figure 3A. CsA-DA-10-EPRM ChemiBeads
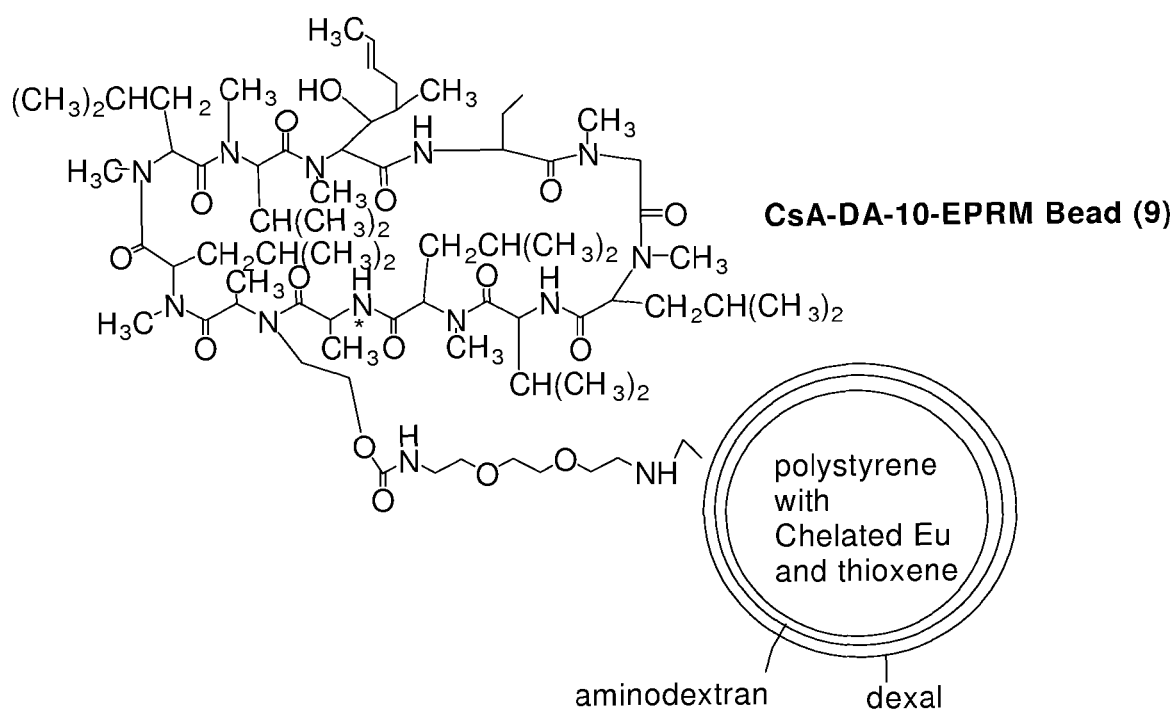
* one isomer has same linker linking through this nitrogen

Figure 3B. CsA-DA-10-HG-APRM ChemiBeads
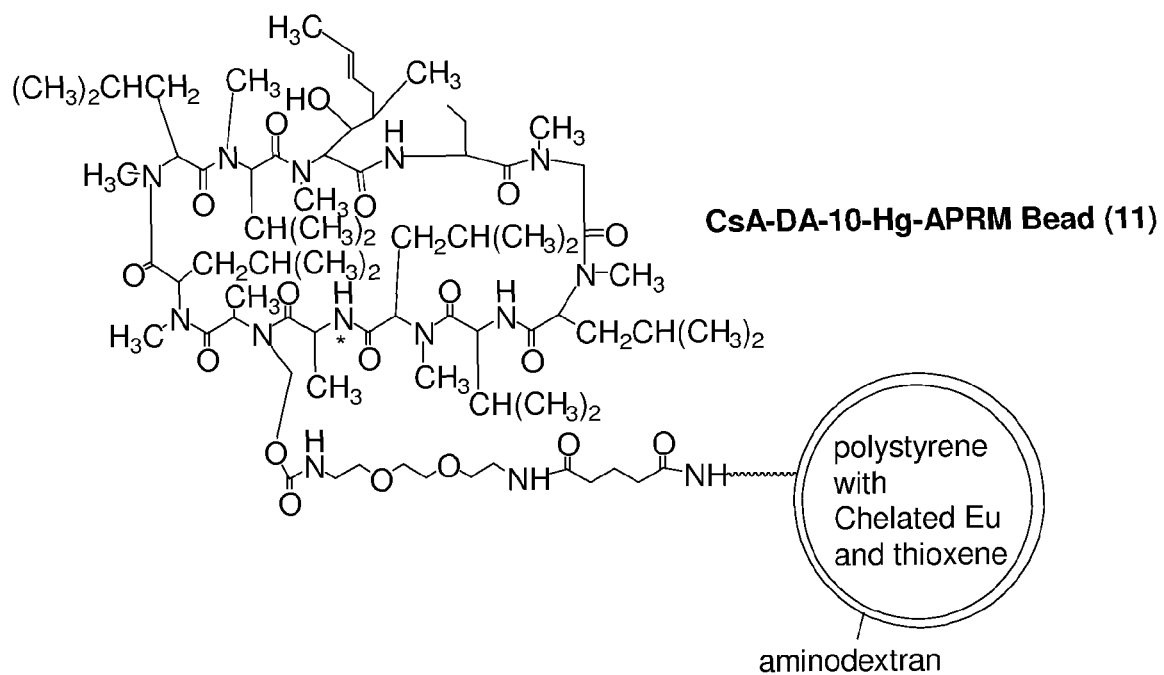
* one isomer has same linker linking through this nitrogen

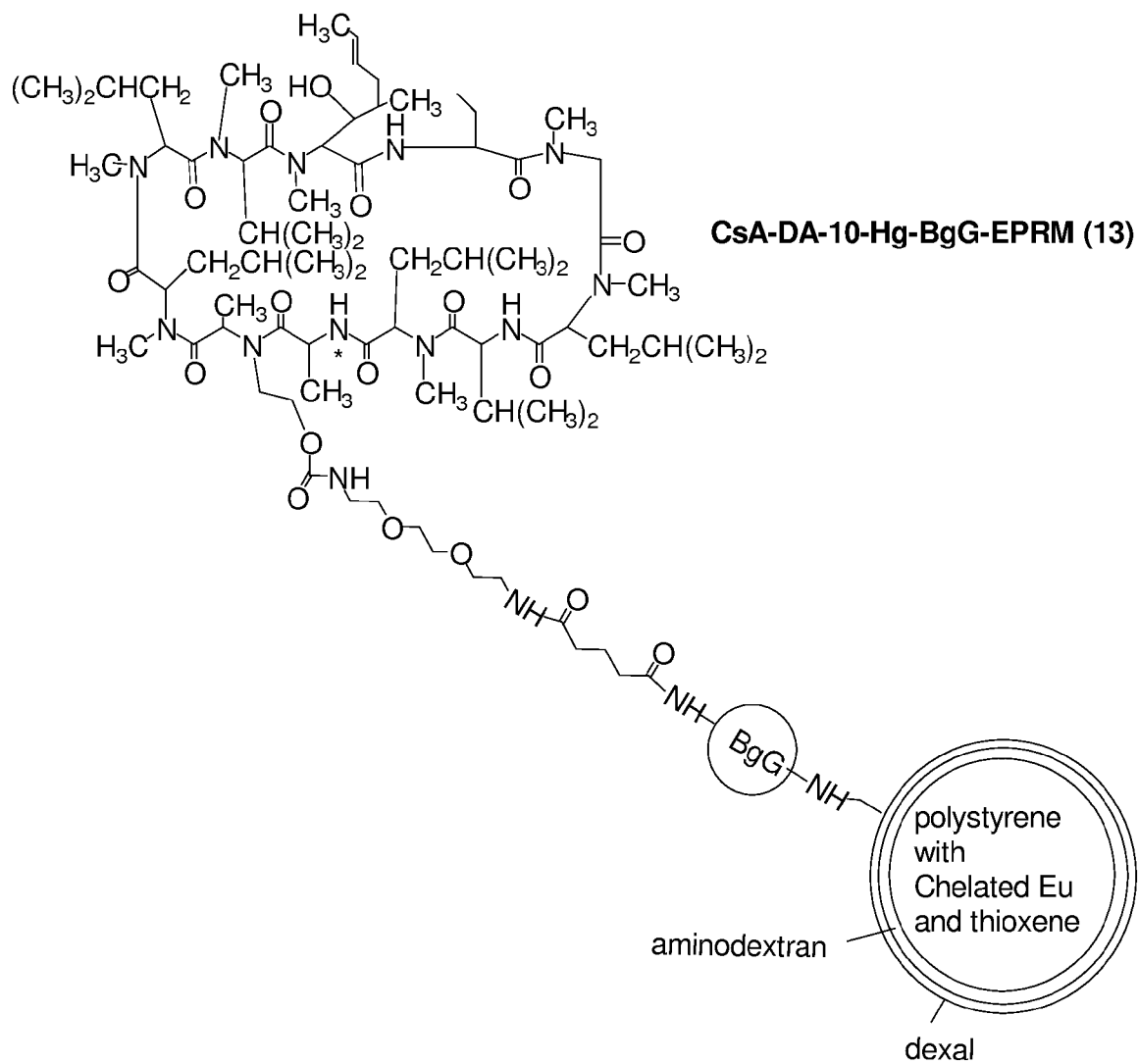
Figure 3C. CsA-DA-10-Hg-BgG-EPRM ChemiBeads
\* Same linker may link through this nitrogen as well Figure 4A. Structure of *anti*-CsA-*m*-Ab-LC-Biotin
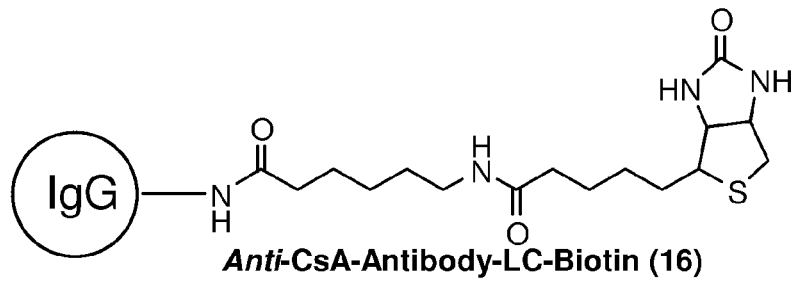
Anti-CsA-Antibody-LC-Biotin (16)
Figure 4B. Structure of anti-CsA-m-Ab-PEO4-Biotin
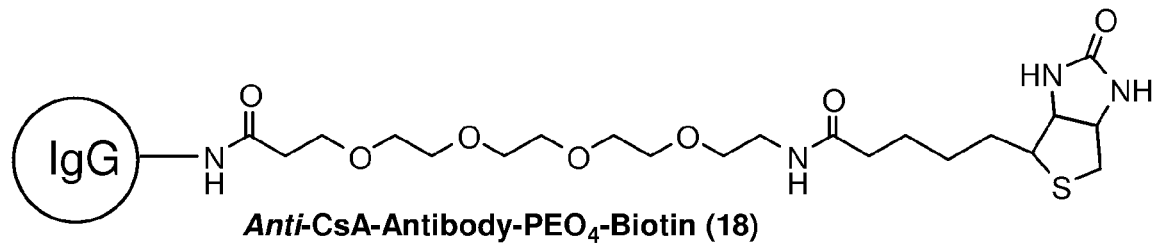
Anti-CsA-Antibody-PEO$_4$-Biotin (18)
Figure 5. *Anti*-CsA-Antibody-EPRM Chemibead
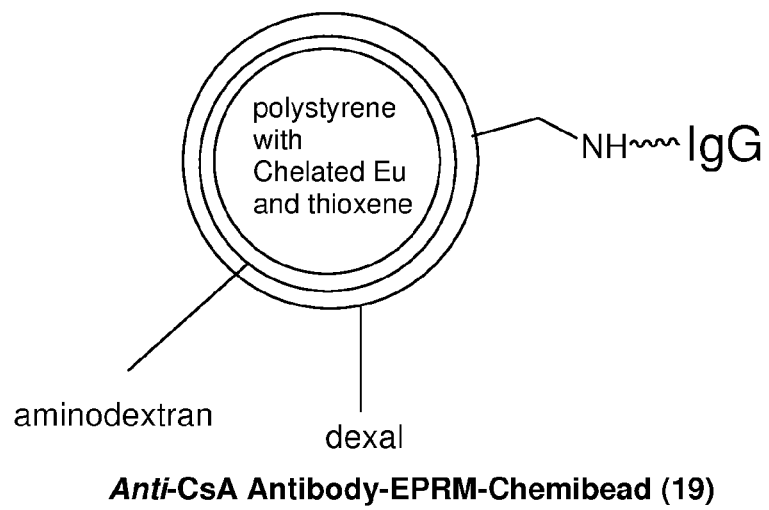
Anti-CsA Antibody-EPRM-Chemibead (19)

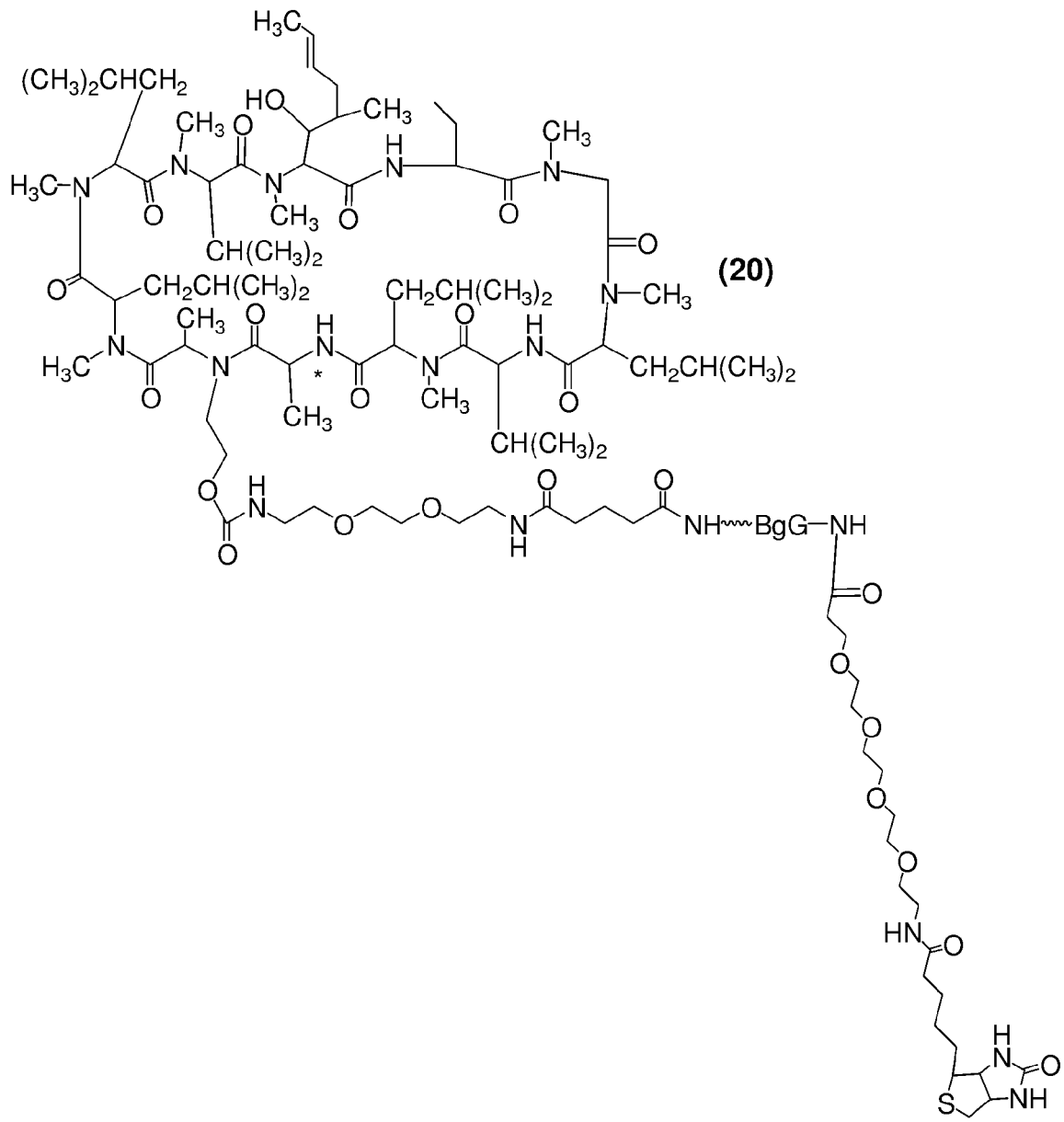
Figure 6. Structure of CsA-DA-10-BgG-PEO₄-Biotin

Figure 7. Structure of CsA-DA-10-PEO4-Biotin
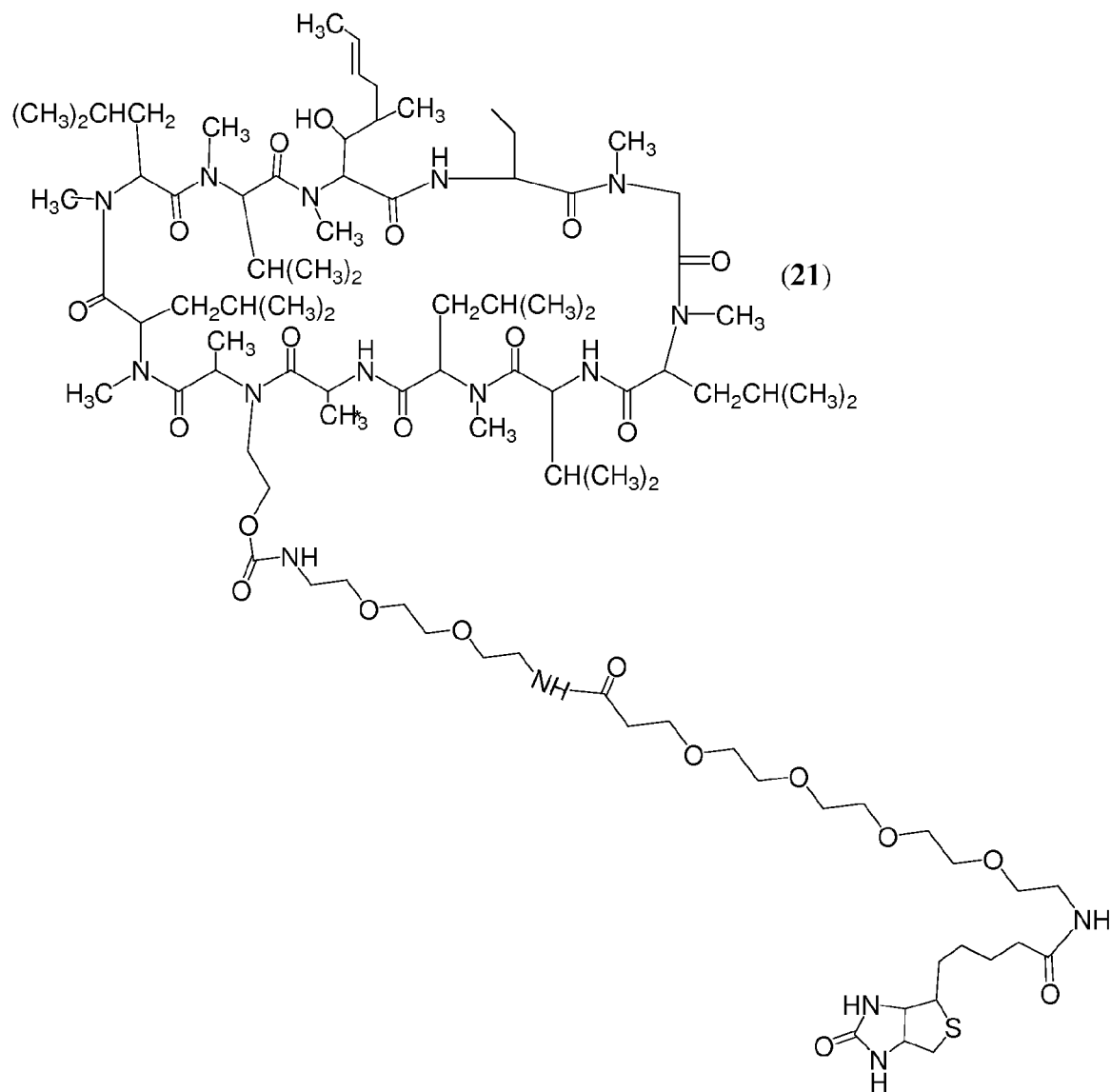
* one isomer has same linker linking through this nitrogen Figure 8. Structure of CsA-DA-10-Bis-Biotin.
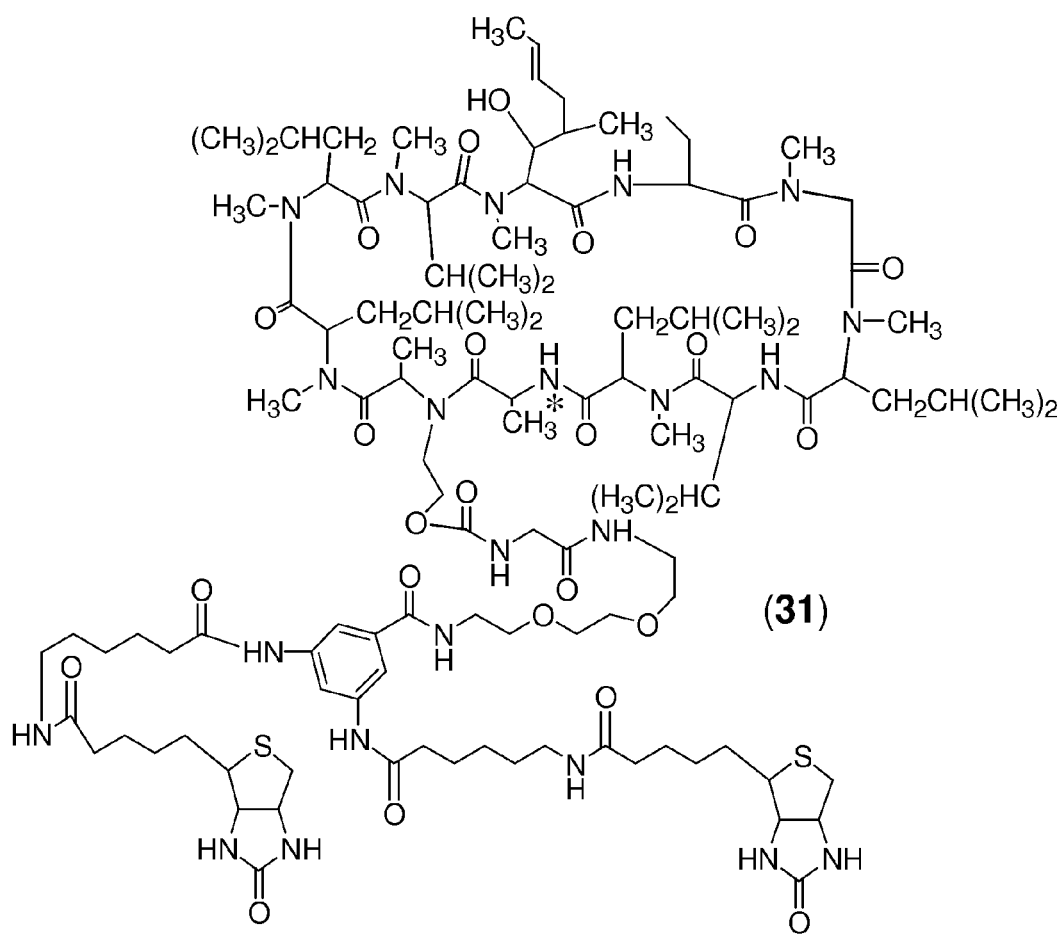
\* one isomer has same linker linking through this nitrogen

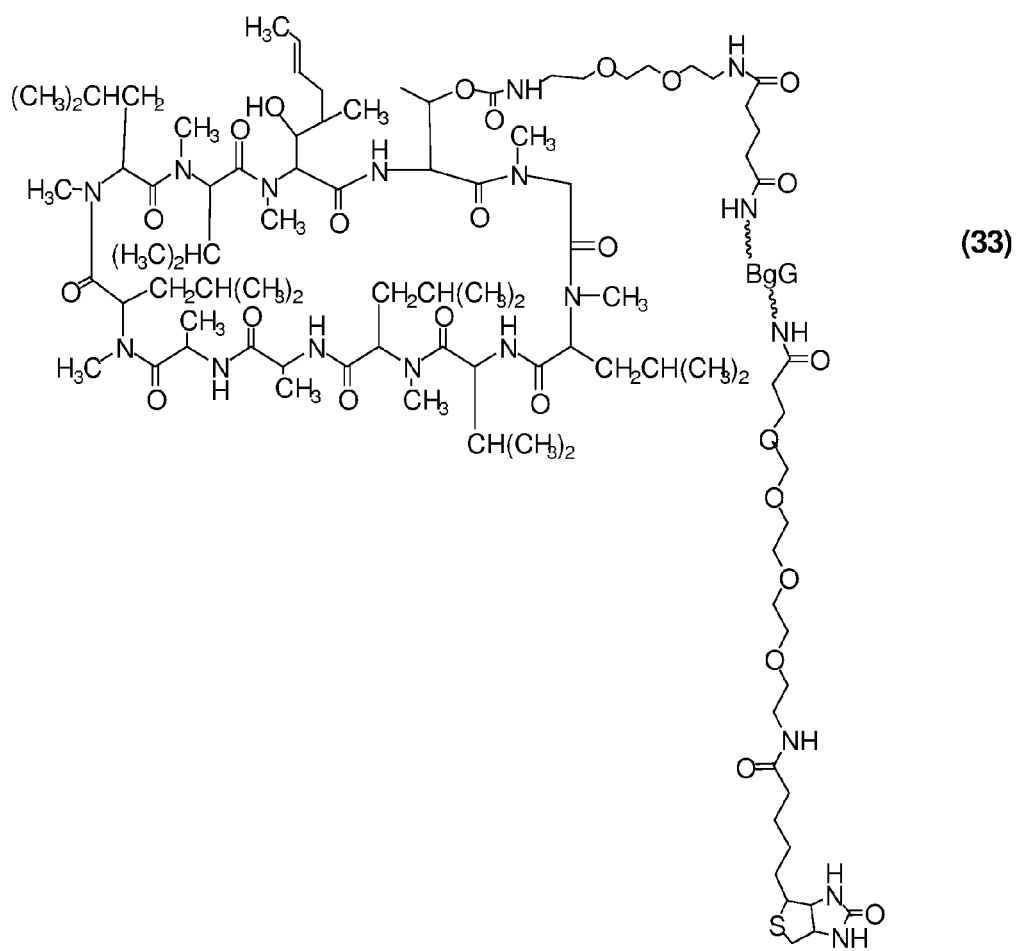
Figure 9. Structure of CsC-DA-10-BgG-PEO4-Biotin
(33)

Scheme 1. Preparation of CsC-DA-10 (3)

Figure 11
Scheme 2. Preparation of CsC-DA-10-EPRM Chemibead
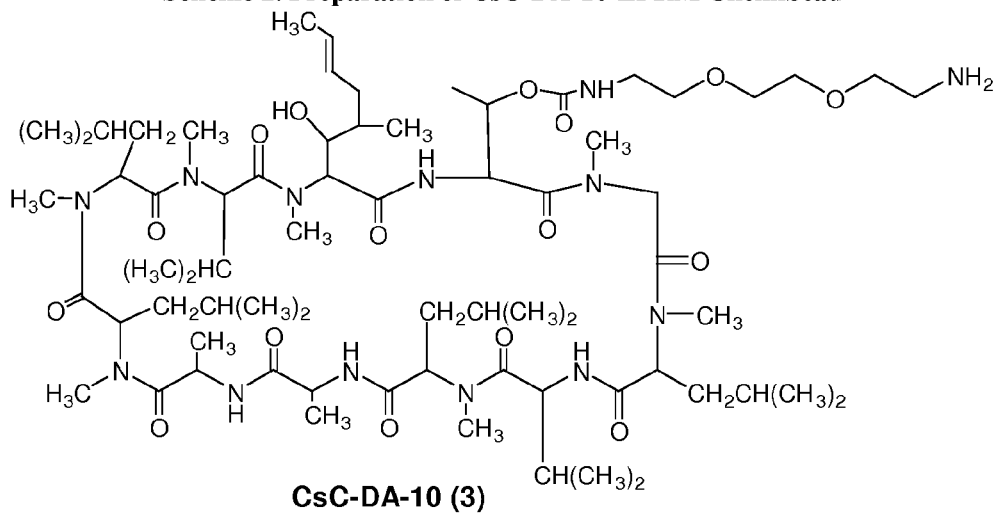
CsC-DA-10 (3)
1) pH =6.0
   NaBH₃CN
2) CMO
3) Wash process
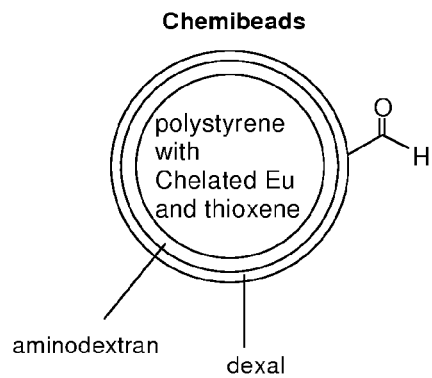
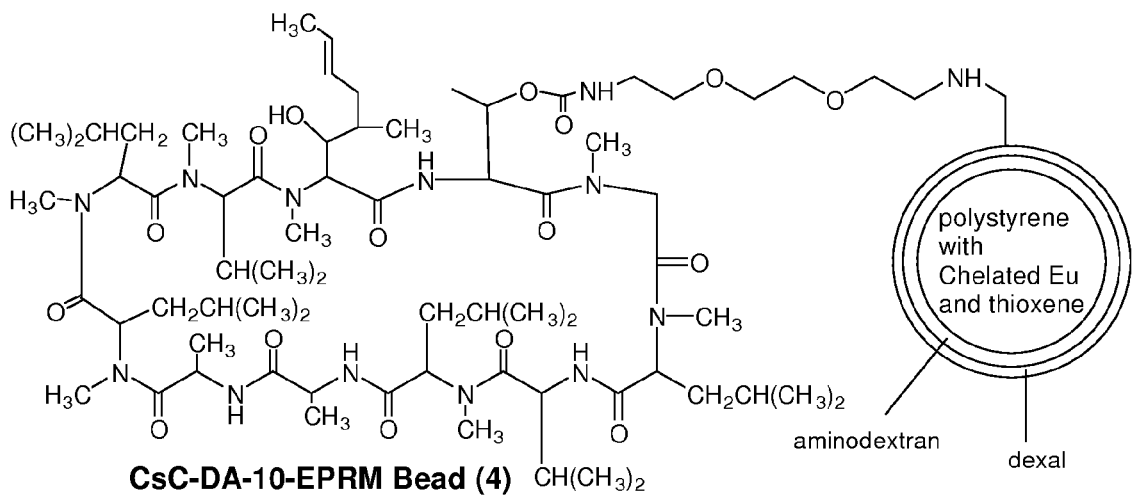
CsC-DA-10-EPRM Bead (4)

Scheme 3. Preparation of CsC-DA-10-Hg-APRM (6)

CsC-DA10-Hg-APRM
(6)

Scheme 4. Preparation of CsA-DA-10-EPRM Chemibead (9)

Scheme 5. Preparation of CsA-DA-10-Hg-APRM (11)

CsA-DA-10-Hg-APRM (11)

* one isomer has same linker linking through this nitrogen

Scheme 6. Synthesis of CsA-BgG-EPRM Bead (13)

1) NaBH₃CN
2) CMO Quench
3) Wash Process (13)

* Same linker may link through this nitrogen as well

Scheme 7. Biotinylation of *anti*-CsA Antibody

Scheme 8. Immobilization of *anti*-CsA antibody to EPRM.

Figure 18
Scheme 9. Preparation of CsA-DA-10-Hg-BgG-Biotin (20) with a protein linker BgG.
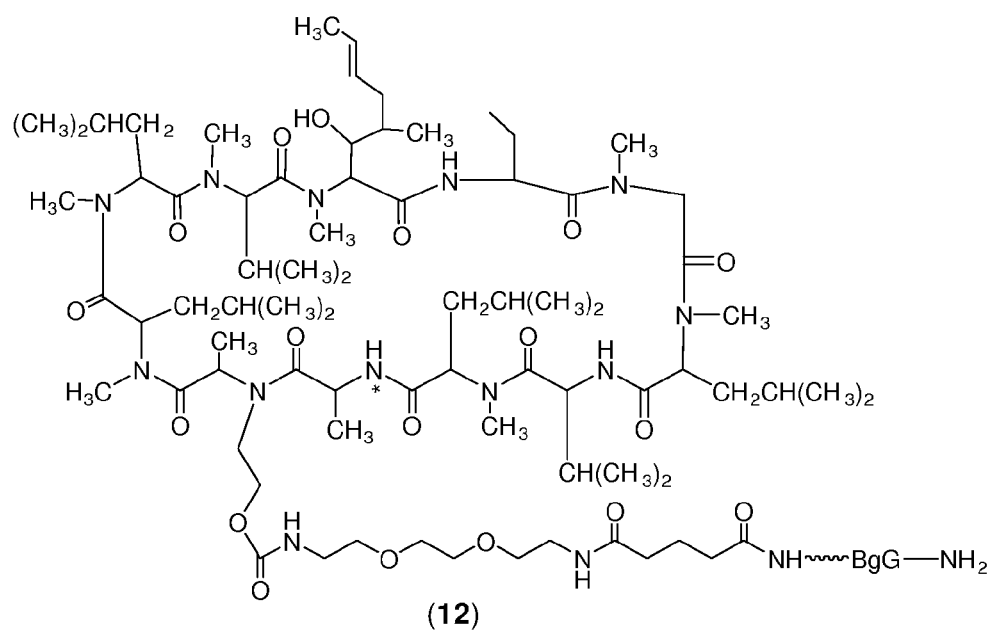
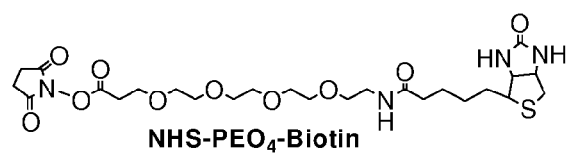
pH = 8.0, 100 mM NaH$_2$PO$_4$-Na$_2$HPO$_4$ \* One isomer has same linker linking through this nitrogen Scheme 10. Direct Biotinylation of CsA-DA-10 (8)

* one isomer has same linker linking through this nitrogen

Scheme 11. Synthesis of Bis-Biotin-Linker (26)

Scheme 12. Synthesis of CsA intermediate (30)

* one isomer has same linker linking through this nitrogen

Figure 22
Scheme 13. Synthesis of CsA-bis-Biotin (31)
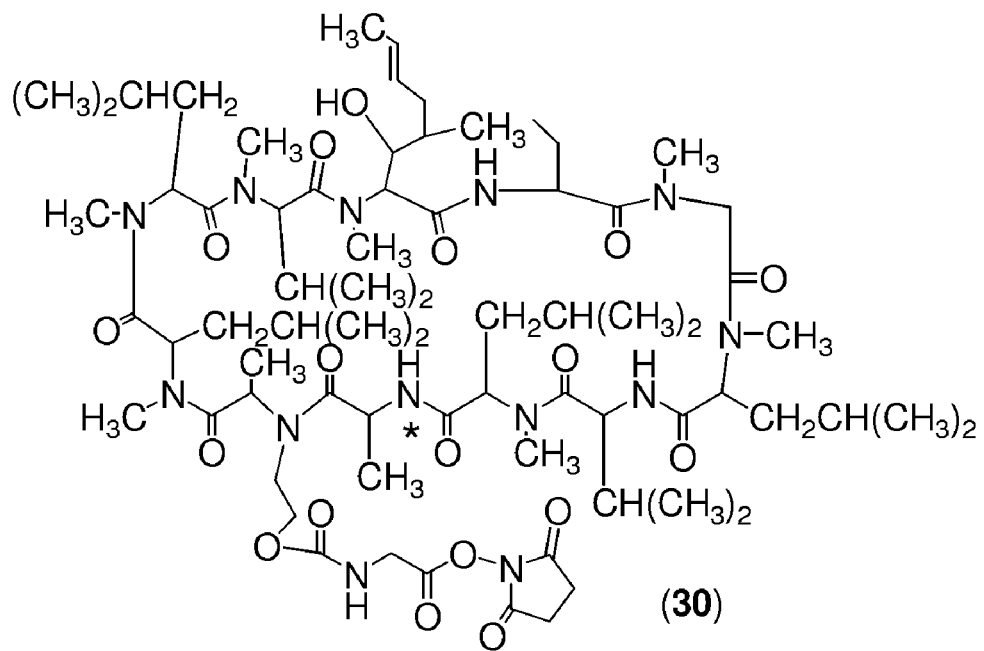
(30)
+
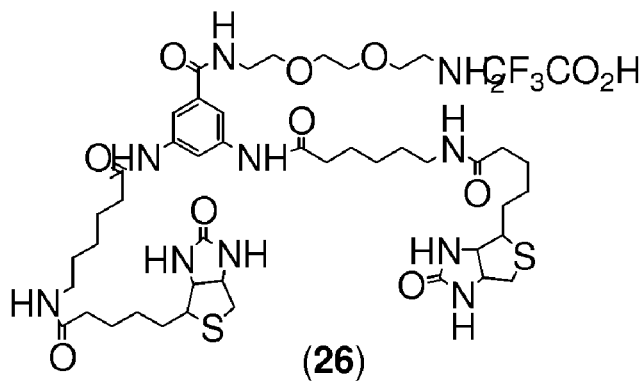
(26)
Et₃N, THF (31)

★ one isomer has same linker linking through this nitrogen

Scheme 14. Preparation of CsC-DA-10-Hg-BgG-Biotin (33).

METHODS FOR DETECTION OF CYCLOSPORIN A

CROSS-REFERENCE TO RELATED APPLICATION

This application is a Divisional of U.S. patent application Ser. No. 11/968,349 filed on Jan. 2, 2008.

BACKGROUND

The invention relates to compounds, methods and kits for the determination of cyclosporin A in samples, such as patient samples, known or suspected to contain cyclosporin A.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are carefully administered to transplant recipients in order to help prevent allograft rejection of non-self tissue. Two most commonly administered immunosuppressive drugs to prevent organ rejection in transplant patients are Cyclosporine (CSA) and FK-506 (FK or tacrolimus). Another drug that finds use as an immunosuppressant in the United States and other countries is sirolimus, also known as rapamycin. Derivatives of sirolimus are also said to be useful as immunosuppressants. Such derivatives include, for example, Everolimus, and the like.

As mentioned above, one drug that finds use as an immunosuppressant in the United States and other countries is cyclosporin A (CsA). CsA is a cyclic undecapeptide of the general structure shown in FIG. 1 wherein all of the alpha-amino acid residues that form the cyclic backbone of cyclosporin A are of the L-configuration except alpha-amino acid 8 which is of the D-configuration. Amino acid residue 1 is derived from an unusual 9 carbon amino acid [2S,3R,4R,6E]-3-hydroxy-4-methyl-2-methylamino-6-octenoic acid. Amino acid residues 1, 3, 4, 6, 9, 10 and 11 are N-methylated on the amide nitrogen atoms of the cyclic backbone of cyclosporin A. Cyclosporin A is described in U.S. Pat. Nos. 4,117,118 (1978) and 4,396,542 (1983), the relevant disclosures of which are incorporated herein by reference.

CsA may have other useful properties such as antibiotic, anti-arthritic and anti-inflammatory activities and may find use in the treatment of other conditions such as diabetes, malaria and autoimmune diseases.

A large number of CsA metabolites that retain the undecapeptide ring have been identified and reported (see Maurer, G.; Loosli, H. R.; Schreier, E.; Keller, B. Drug Metabolism and Disposition 1984, 12(1), 120-126, the structures, nomenclature and analytical data of the metabolites are incorporated herein by reference.

Even though CsA is a highly effective immunosuppressant drug, its use must be carefully managed because the effective dose range is narrow and excessive dosage can result in serious side effects. Renal dysfunction, hypertension, cardiovascular cramps, hirsutism, acne, tremor, convulsions, headache, gum hyperplasia, diarrhea, nausea, vomiting, hepatotoxicity, abdominal discomfort, paresthesia, flushing, leukopenia, lymphoma, sinusitis and gynecomastia have been observed in kidney, heart or liver transplant patients undergoing CsA treatment. The administration of too little CsA can lead to graft rejection.

Management of CsA dosage involves careful control of the level of the drug present in the patient. Because the distribution and metabolism of CsA varies greatly between patients, and because of the wide range and severity of adverse reactions, accurate monitoring of drug level is considered essential. The side effects associated with some immunosuppressant drugs can be controlled in part by carefully controlling the level of the drug present in a patient. Therapeutic monitoring of concentrations of immuno-suppressant drugs and related drugs in blood is required to optimize dosing regimes to ensure maximal immunosuppression with minimal toxicity. As mentioned above, although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because the distribution and metabolism of an immunosuppressant drug can vary greatly between patients and because of the wide range and severity of adverse reactions, accurate monitoring of the drug level is essential.

Laboratory methods for detection of cyclosporin have been developed. These techniques typically involve high performance liquid chromatography (HPLC), radioimmunoassay (RIA) or florescence polarization immunoassay (FPIA). Each of these techniques has certain limitations with regard to safety and complexity of the procedure and level of specificity for cyclosporins of interest. For example, HPLC requires long sample preparation and/or run times using high cost labor-intensive procedures; RIA presents the well-known hazards of handling radioactive materials; and FPIA, when based on non-specific mono- or polyclonal-antibodies, often fails to distinguish between CsA and its metabolites.

Immunoassay techniques have also been used for measuring the amount of cyclosporin in a sample suspected of containing cyclosporin. However, most available antibodies capable of recognizing cyclosporins of interest also recognize and cross-react with closely related compounds such as cyclosporin metabolites. Because of this cross-reactivity, immunoassays dependent on these antibodies are less specific to cyclosporins of interest than might be desired.

There is, therefore, a continuing need to develop fast and accurate diagnostic methods to measure levels of CsA or derivatives thereof in patients. A simple analytical method specific to CsA is needed for use in cyclosporin treatment management.

SUMMARY

One embodiment of the present invention is a method for determining the presence and/or amount of cyclosporin A in a medium suspected of containing cyclosporin A. In the method a combination is provided in a medium. The combination comprises (i) the sample, (ii) a first member of a signal producing system (sps) associated with a first support wherein the first sps member is capable of activating a second member of the sps and wherein the first support is associated with a first member of a specific binding pair, and (iii) the second sps member associated with a second support wherein the second sps member is activatable by the first sps member. The second support comprises either (I) cyclosporin C or cyclosporin A and the combination further comprises a conjugate of an antibody for cyclosporin A and a second member of the specific binding pair or (II) antibody for cyclosporin A and the combination further comprises a conjugate of cyclosporin A and a second member of the specific binding pair. The combination is subjected to conditions for binding of cyclosporin A to the antibody for cyclosporin A. The first sps member is activated and the amount of signal generated by the second sps member is detected. The amount of signal is related to the presence and/or amount of cyclosporin A in the sample.

Another embodiment of the present invention is a method for determining the presence and/or amount of cyclosporin A in a medium suspected of containing cyclosporin A. A combination is provided in a medium where the combination comprises (i) the sample, (ii) a sensitizer associated with a first particle wherein the sensitizer is capable of activating a chemiluminescent composition and wherein the first particle is associated with a first member of a specific binding pair, and (iii) a chemiluminescent composition associated with a second particle wherein the chemiluminescent composition is activatable by the sensitizer. The second particle may comprise (I) cyclosporin C and the combination further comprises a conjugate of an antibody for cyclosporin A and a second member of the specific binding pair or the second particle may comprise (II) antibody for cyclosporin A and the combination further comprises a conjugate of cyclosporin A and a second member of the specific binding pair. The combination is subjected to conditions for binding of cyclosporin A to the antibody for cyclosporin A. The sensitizer is activated and the amount of luminescence generated by the chemiluminescent composition is detected, the amount of luminescence being related to the presence and/or amount of cyclosporin A in the sample. In some embodiments the specific binding pair comprises streptavidin and biotin.

Another embodiment of the present invention is a method for determining the presence and/or amount of cyclosporin A in a medium suspected of containing cyclosporin A. A combination is provided in a medium wherein the combination comprises (i) the sample, (ii) a photosensitizer associated with a first particle and being capable of generating singlet oxygen wherein the first particle comprises a biotin binding partner, (iii) a conjugate of cyclosporin A and biotin, and (iv) a chemiluminescent composition activatable by singlet oxygen and associated with a second particle wherein the second particle comprises an antibody for cyclosporin A. The combination is subjected to conditions for binding of cyclosporin A to the antibody for cyclosporin A. The photosensitizer is irradiated with light and the amount of luminescence generated by the chemiluminescent composition is detected, the presence and/or amount of luminescence being related to the amount of cyclosporin A in the sample.

Another embodiment of the present invention is a method for determining the presence and/or amount of cyclosporin A in a medium suspected of containing cyclosporin A. The method comprises providing in combination in a medium (i) the sample, (ii) a photosensitizer associated with a first particle and being capable of generating singlet oxygen wherein the first particle comprises a biotin binding partner, (iii) a chemiluminescent composition activatable by the singlet oxygen and associated with a second particle wherein the second particle comprises cyclosporin C and (iv) a conjugate of an antibody for cyclosporin A and biotin. The combination is subjected to conditions for binding of cyclosporin A, if present, to the antibody for cyclosporin A. The photosensitizer is irradiated with light and the amount of luminescence generated by the chemiluminescent composition is detected, the amount of luminescence being related to the presence and/or amount of cyclosporin A in the sample.

BRIEF DESCRIPTION OF THE DRAWINGS

FIG. 1 is a depiction of the structures of cyclosporin A and cyclosporin C.

FIG. 2A is a depiction of the structure of a conjugate of cyclosporin C and chemiluminescent particles. FIG. 2B is a depiction of the structure of another conjugate of cyclosporin C and chemiluminescent particles.

FIG. 3A is a depiction of the structure of a conjugate of cyclosporin A and chemiluminescent particles. FIG. 3B is a depiction of the structure of another conjugate of cyclosporin A and chemiluminescent particles. FIG. 3C is a depiction of the structure of another conjugate of cyclosporin A and chemiluminescent particles.

FIG. 4A is a depiction of the structure of a conjugate of antibody for cyclosporin A and biotin. FIG. 4B is a depiction of the structure of another conjugate of antibody for cyclosporin A and biotin.

FIG. 5 is a depiction of the structure of a conjugate of an antibody for cyclosporin A and chemiluminescent particles.

FIG. 6 is a depiction of the structure of a conjugate of cyclosporin A and biotin.

FIG. 7 is a depiction of the structure of another conjugate of cyclosporin A and biotin.

FIG. 8 is a depiction of the structure of a conjugate of cyclosporin A and bis-biotin.

FIG. 9 is a depiction of the structure of a conjugate of cyclosporin C and biotin.

FIG. 11 is a depiction of the preparation of a reagent comprising cyclosporin C linked to a chemiluminescent particle.

DETAILED DESCRIPTION OF SPECIFIC EMBODIMENTS

General Discussion

Figure 10:
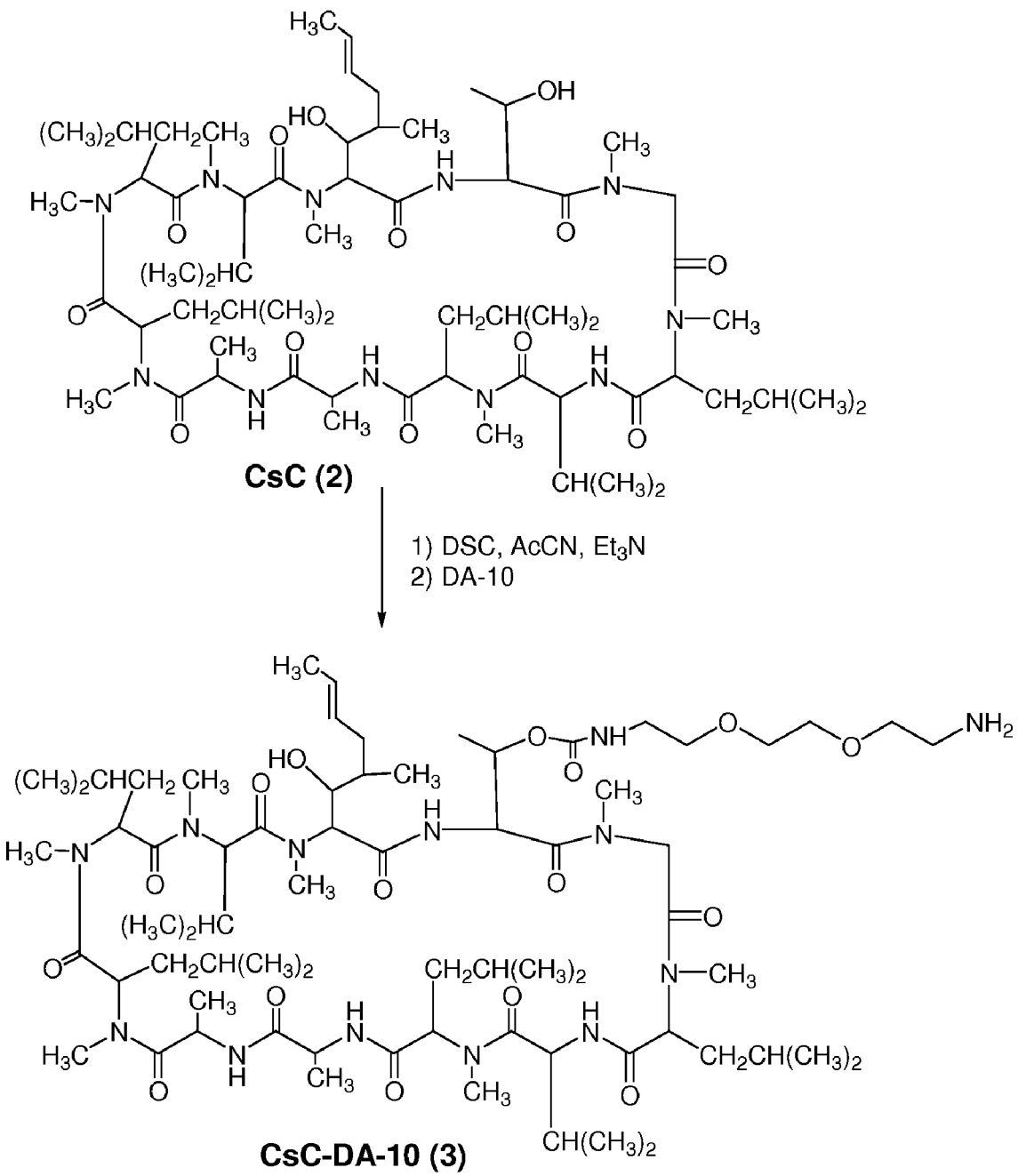
FIG. 10 is a depiction of the preparation of cyclosporin C with a linking group.

The methods and compositions of the present invention relate to simple, specific immunoassay methods for detecting CsA. The current methods comprise assay reagents and formats that achieve not only sufficient signal generation but also achieve good sensitivity at the low end of the medical decision range, typically about 30 ng/mL of cyclosporin A (CsA) in a patient sample. One can monitor sensitivity at the low end of the medical decision range by carrying out experiments with samples that contain know amounts of cyclosporin A. Such samples are often referred to as calibrators. Typically, the calibrators are tested in a manner similar to the testing of a sample suspected of containing CsA, the amount of which in the sample is usually unknown. The calibrators typically contain differing, but known, concentrations of CsA. Preferably, the concentration ranges present in the calibrators span the range of suspected CsA concentrations in unknown samples.

Sensitivity of a particular assay format at the low end of the medical decision range can be monitored by monitoring the difference in the amount of signal obtained for a calibrator that contains no CsA, arbitrarily designated calibrator 1, and the amount of signal obtained for a calibrator for the first sample containing a known amount of CsA above zero, arbitrarily designated calibrator 2. The concentration of CsA in calibrator 2 is about 60 to about 100 ng/mL, or about 65 to about 95 ng/mL, or about 70 to about 90 ng/mL, or about 75 to about 85 ng/mL, or about 80 ng/mL.

A large difference between the signal for calibrator 1 and calibrator 2 is desired. For good sensitivity in the medical decision range, the difference in the signal detected between calibrator 1 and calibrator 2 is at least about 30%, at least about 35%, at least 40%, at least about 45%, at least about 50%, at least about 55%, at least 60%, at least about 65%, at least about 70%, and so forth. In some embodiments the difference in the signal detected between calibrator 1 and calibrator 2 is about 40% to about 60%, or about 40% to about 55%, or about 40% to about 50%, or about 45% to about 60%, or about 45% to about 55%, or about 45% to about 50%, or about 50% to about 60%, or about 50% to about 55%, and the like.

Depending on the assay format, the difference in signal may be an increase in signal or a decrease in signal. In many embodiments the difference in signal is a decrease in signal with various embodiments of the instant methods. Typically, the results of the assays using the calibrators are presented in a graph format wherein the amount of signal is plotted against the concentration of the calibrators. In accordance with embodiments of the present invention the slope of the line between calibrator 1 and calibrator 2 is usually steeper compared with results obtained with assay formats not in accordance with the present embodiments.

To achieve the desired sensitivity in the medical decision range, the present inventors discovered that certain reagents and assay formats may be employed. In the present methods for determining the presence and/or amount of cyclosporin A in a medium suspected of containing cyclosporin A, a combination is provided in a medium where the combination comprises (i) the sample, (ii) a first sps member such as, for example, a sensitizer associated with a first support such as, for example, a particle, wherein the first sps member is capable of activating a second sps member and wherein the first support is associated with a first member of a specific binding pair, and (iii) the second sps member such as, for example, a chemiluminescent composition, associated with a second support such as, for example, particle, wherein the second sps member is activatable by the first sps member.

Two different approaches may be employed with the above reagents. In one approach, the second support may comprise (I) cyclosporin C and the combination further comprises a conjugate of an antibody for cyclosporin A and a second member of the specific binding pair. In another approach, the second support may comprise (II) antibody for cyclosporin A and the combination further comprises a conjugate of cyclosporin A and a second member of the specific binding pair. In either approach, the resulting combination is subjected to conditions for binding of cyclosporin A to the antibody for cyclosporin A. The first sps member is activated and the amount of signal generated by the second sps member is detected, the amount of signal being related to the presence and/or amount of cyclosporin A in the sample.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The sample to be analyzed is one that is suspected of containing CsA. The samples are preferably from humans or animals and include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum and, in a particular embodiment the sample is whole blood.

The sample can be prepared in any convenient medium. Conveniently, the sample may be prepared in an assay medium, which is discussed more fully below. In some instances a pretreatment may be applied to the sample such as, for example, to lyse blood cells, and the like. Such pretreatment is usually performed in a medium that does not interfere subsequently with an assay. An aqueous medium is preferred for the pretreatment and typically is one that may be solely water or may include from 0.1 to about 40 volume percent of a cosolvent such as, for example, an organic solvent, which may be an alcohol, ether, ester, and the like. The medium may also comprise one or more preservatives as are known in the art such as, for example, sodium azide, neomycin sulfate, PROCLIN® 300, Streptomycin, and the like. The pH for the medium will usually be in the range of about 4 to about 11, more usually in the range of about 5 to about 10, and preferably in the range of about 6.5 to about 9.5.

Various buffers may be used to achieve the desired pH and maintain the pH during the incubation period. Illustrative buffers include borate, phosphate, carbonate, tris, barbital, PIPES, HEPES, MES, ACES, MOPS, BICINE, and the like. The medium may also comprise agents for preventing the formation of blood clots. Such agents are well known in the art and include, for example, EDTA, EGTA, citrate, heparin, and the like. Various ancillary materials may be employed in the above methods.

In the methods discussed generally above, a signal producing system ("sps") is employed. The sps has at least first and second sps members. The designation "first" and "second" is completely arbitrary and is not meant to suggest any order or ranking among the sps members or any order of addition of the sps members in the present methods. The sps members may be labels. The sps members are related in that activation of one member of the sps produces a product such as, e.g., light, which results in activation of another member of the sps. In some embodiments the sps members comprise a sensitizer and a chemiluminescent composition where activation of the sensitizer results in a product that activates the chemiluminescent composition. The second sps member usually generates a detectable signal that relates to the amount of bound and/or unbound sps member, i.e. the amount of sps member bound or not bound to the CsA being detected or to an agent that reflects the amount of the CsA to be detected.

In some embodiments the first sps member is a sensitizer, such as, for example, a photosensitizer and the second sps member is a chemiluminescent composition that is activated as a result of the activation of the first sps member. The sensitizer may be any moiety that upon activation produces a product that activates the chemiluminescent composition, which in turn generates a detectable signal. In many embodiments the sensitizer is capable of generating singlet oxygen upon activation.

In many embodiments the sensitizer is a photosensitizer for generation of singlet oxygen usually by excitation with light. The photosensitizer can be photoactivatable (e.g., dyes and aromatic compounds) or chemi-activated (e.g., enzymes and metal salts). When excited by light the photosensitizer is usually a compound comprised of covalently bonded atoms, usually with multiple conjugated double or triple bonds. The compound should absorb light in the wavelength range of about 200 to about 1100 nm, or about 300 to about 1000 nm, or about 450 to about 950 nm, with an extinction coefficient at its absorbance maximum greater than about 500 $M^{-1}$ $cm^{-1}$, or at least about 5000 $M^{-1}$ $cm^{-1}$, or at least about 50,000 $M^{-1}$ $cm^{-1}$ at the excitation wavelength. Photosensitizers that are to be excited by light will be relatively photostable and will not react efficiently with singlet oxygen.

Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures. Typical photosensitizers include acetone, benzophenone, 9-thioxanthone, eosin, 9,10-dibromoanthracene, methylene blue, metallo-porphyrins, such as hematoporphyrin, phthalocyanines, chlorophylis, rose bengal, buckminsterfullerene, etc., and derivatives of these compounds having substituents of 1 to 50 atoms for rendering such compounds more lipophilic or more hydrophilic and/or as attaching groups for attachment, for example, to an sps member or an sbp member.

The photosensitizers useful in the present methods include other substances and compositions that can produce singlet oxygen with or, less preferably, without activation by an external light source. Thus, for example, molybdate salts and chloroperoxidase and myeloperoxidase plus bromide or chloride ion (Kanofsky, J. Biol. Chem. (1983) 259 5596) have been shown to catalyze the conversion of hydrogen peroxide to singlet oxygen and water. Also included within the scope of the invention as photo sensitizers are compounds that are not true sensitizers but which on excitation by heat, light, or chemical activation will release a molecule of singlet oxygen. The best known members of this class of compounds includes the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

Examples of other photosensitizers that may be utilized are those set forth in U.S. Pat. No. 6,153,442 and U.S. Patent Application Publication No. 20050118727A, the disclosures of which are incorporated herein by reference.

The chemiluminescent composition comprises a substance that undergoes a chemical reaction upon direct or sensitized excitation by light or upon reaction with singlet oxygen or upon chemical activation to form a metastable reaction product that is capable of decomposition with the simultaneous or subsequent emission of light, usually within the wavelength range of about 250 to about 1200 nm. In some embodiments the chemiluminescent composition comprises a substance that reacts with singlet oxygen to form dioxetanes or dioxetanones. The latter are usually electron rich olefins. Exemplary of such electron rich olefins are enol ethers, enamines, 9-alkylidene-N-alkylacridans, arylvinylethers, dioxenes, arylimidazoles, 9-alkylidene-xanthanes and lucigenin. Other compounds include luminol and other phthalhydrazides and chemiluminescent compounds that are protected from undergoing a chemiluminescent reaction by virtue of their being protected by a photochemically labile protecting group, such compounds including, for example, firefly luciferin, aquaphorin, luminol, and the like.

The chemiluminescent compounds preferably emit at a wavelength above 300 nm, preferably above 500 nm, and more preferably above 550 nm. Compounds that absorb and emit light at wavelengths beyond the region where the sample components contribute significantly to light absorption are of particular use in embodiments of the present methods. The electron rich olefins generally have an electron-donating group in conjugation with the olefin. The more preferred olefins are those that yield a dioxetane that decays rapidly at room temperature (less than 60 minutes, preferably less than 5 minutes, desirably less than 30 sec). The dioxetanes may be luminescent alone or in conjunction with a fluorescent energy acceptor. Such olefins include, for example, enol ethers, enamines, 9-alkylidene-N-alkylacridans, 9-alkylidene-xanthanes, 2,3-dihydro-1,4-phthalazinediones, 2,4,5-triphenylimidazoles, and the like.

Examples of other chemiluminescent compounds that may be utilized are those set forth in U.S. Pat. No. 6,153,442 and U.S. Patent Application Publication No. 20050118727A, the disclosures of which are incorporated herein by reference.

The sps members are each associated with a support, which may be the same type of support or a different type of support for each sps member. As used herein, the phrase "associated with" includes covalent binding of one moiety to another moiety either by a direct bond or through a linking group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The support may be comprised of an organic or inorganic, solid or fluid, water insoluble material, which may be transparent or partially transparent. The support can have any of a number of shapes, such as particulate including beads and particles, film, membrane, tube, well, strip, rod, planar surfaces such as, e.g., plate, DENDRIMERS, and the like. Depending on the type of assay, the support may or may not be suspendable in the medium in which it is employed. Examples of suspendable supports are polymeric materials such as latex, lipid bilayers or liposomes, oil droplets, cells and hydrogels, magnetic particles, and the like. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

In some embodiments the supports employed for the first and second sps members are particles. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli*, viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are chrome particles or latex particles.

The polymer particles can be formed of addition or condensation polymers. The particles will be readily dispersible in an aqueous medium and can be adsorptive or functionalizable so as to permit conjugation to an sps member, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

An sps member may be associated with a solid support in any manner known in the art. In some embodiments, the sps member may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the sps member. Other methods of binding the sps members are also possible. For instance, a solid support may have a coating of a binder for a small molecule such as, for example, avidin, an antibody, etc., and a small molecule such as, e.g., biotin, hapten, etc., can be bound to the CsA derivative or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.,* 245:3059 (1970).

The present methods employ at least one antibody for the CsA. By the phrase "antibody for the CsA" is meant an antibody that binds specifically to CsA and does not bind to any significant degree to non-cyclosporin entities such that the analysis for CsA would be distorted.

Antibodies specific for a CsA for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1-24 (1975); Broughton and Strong, Clin. Chem. 22: 726-732 (1976); and Playfair, et al., Br. Med. Bull. 30: 24-31 (1974).

Antibodies can also be obtained by somatic cell hybridization techniques, such antibodies being commonly referred to as monoclonal antibodies. Monoclonal antibodies may be produced according to the standard techniques of Köhler and Milstein, *Nature* 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites.

In addition to antibodies for CsA, reagents of the present methods also include members of a specific binding pair ("sbp") for binding particles to CsA analogs or to antibodies for CsA. The sbp member is one of two different molecules, having an area on the surface or in a cavity, which specifically binds to and is thereby defined as complementary with a particular spatial and polar organization of the other molecule. The members of the specific binding pair may be members of an immunological pair such as antigen-antibody, e.g., fluorescein-anti-fluorescein, etc., or other specific binding pairs such as, for example, biotin binding partner-biotin, hormones-hormone receptors, enzyme-substrate, nucleic acid duplexes, IgG-protein A, polynucleotide pairs such as DNA-DNA, DNA-RNA, and the like.

A "CsA analog" is a modified drug that can compete with the analogous CsA for a receptor, the modification providing means to join a CsA analog to another molecule. The CsA analog will usually differ from the CsA by more than replacement of a hydrogen with a bond which links the drug analog to a hub or label, but need not. The CsA analog binds to the receptor in a manner similar to the binding of CsA to the receptor. The CsA analog may be, for example, the CsA conjugated to another molecule through a linking group, an antibody directed against the idiotype of an antibody to the CsA, and so forth. A "conjugate" as used herein is a molecule comprised of two or more subunits bound together, optionally through a linking group, to form a single structure. The binding can be made either by a direct connection (e.g. a chemical bond) between the subunits or by use of a linking group. For example, in one context of the present invention, cyclosporin A conjugated, optionally through a linking group, to biotin is a cyclosporin A-biotin conjugate. "Conjugation" is any process wherein two subunits are linked together to form a conjugate. The conjugation process can be comprised of any number of steps.

In many embodiments the sbp members are biotin and biotin-binding partner. Biotin includes bis-biotin. The biotin-binding partner may be any moiety that binds to biotin such as, for example, avidin, streptavidin, antibody for biotin and the like.

In some embodiments the present methods involve induced luminescence, which is described in U.S. Pat. No. 5,340,716 (the '716 patent) (Ullman, et al.) entitled "Assay Method Utilizing Photoactivated Chemiluminescent Label" ("induced luminescence assay"), which disclosure is incorporated herein by reference. The induced luminescence assay utilizes a particle incorporating a photosensitizer and a label particle incorporating a chemiluminescent compound. The label particle is conjugated to an sbp member, for example, an antibody for the compound of interest, which is capable of binding to the compound of interest to form a complex, or to a second sbp member to form a complex, in relation to the presence of the compound of interest. If the compound of interest is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of the compound of interest present.

U.S. Pat. No. 7,189,582 (the '582 patent) discloses an assay that employs induced luminescence wherein a chemiluminescent particle is employed, which comprises a chemiluminescent compound associated therewith such as by incorporation therein or attachment thereto. An sbp member that binds to sirolimus, such as, for example, an antibody for sirolimus, is bound to a polysaccharide coating these particles. A second sbp member that binds to sirolimus is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are mixed with a sample suspected of containing sirolimus and with the photosensitizer particles. The reaction medium is incubated to allow the particles to bind to the sirolimus by virtue of the binding of the sbp members to the sirolimus. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of sirolimus, it is activated by the singlet oxygen and emits luminescence. The medium is then examined for the presence and/or the amount of luminescence or light emitted, the presence thereof being related to the presence of sirolimus in the sample.

Among others, the enhanced sensitivity at the low end of the medical decision range that is achieved in the present embodiments in an assay for CsA that utilizes CsC, rather than CsA, bound to a particle having a chemiluminescent composition associated therewith is unexpected. Furthermore, an assay method for CsA that employs antibody for CsA where the antibody is associated with a particle having a chemiluminescent composition associated therewith is undisclosed.

The assays discussed herein are normally carried out in an aqueous buffered medium at a moderate pH, generally that which provides optimum assay sensitivity. The aqueous medium may be solely water or may include from 0.1 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth. For example, in addition to buffers and preservatives, the medium may comprise stabilizers for the medium and for the reagents employed. The medium may comprise an agent for mitigating the effect of binding proteins in the sample where the binding proteins bind to CsA. Such agents may be, for example, an ester of CsA. All of the above materials are present in a concentration or amount sufficient to achieve the desired effect or function.

Various buffers may be used to achieve the desired pH and maintain the pH during the determination. Illustrative buffers include borate, phosphate, carbonate, tris, barbital and the like. The particular buffer employed is not critical, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; binding enhancers, e.g., polyalkylene glycols; or the like.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 24 hours, or about 1 second to about 6 hours, or about 2 seconds to about 1 hour, or about 1 to about 15 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., or from about 15 to about 40° C.

The concentration of CsA analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of CsA analyte present in the sample), the particular detection technique and the concentration of the analyte normally determine the concentrations of the various reagents.

The concentrations of the various reagents in the assay medium will generally be determined by the concentration range of interest of the CsA analyte, the nature of the assay, and the like. However, the final concentration of each of the reagents is normally determined empirically to optimize the sensitivity of the assay over the range. That is, a variation in concentration of CsA analyte that is of significance should provide an accurately measurable signal difference. Considerations such as the nature of the signal producing system and the nature of the analytes normally determine the concentrations of the various reagents.

As mentioned above, the sample and reagents are provided in combination in the medium. While the order of addition to the medium may be varied, there will be certain preferences for some embodiments of the assay formats described herein. For example in an assay format in which a conjugate of CsA and biotin is employed, adding the conjugate as the last reagent to be added to the assay medium enhances performance of the assay. The simplest order of addition, of course, is to add all the materials simultaneously and determine the effect that the assay medium has on the signal as in a homogeneous assay. Alternatively, the reagents can be combined sequentially. Optionally, an incubation step may be involved subsequent to each addition as discussed above.

Examination Step

In a next step of the methods in accordance with the present disclosure, the medium is examined for the presence of a complex comprising the CsA and the antibody for the CsA. The presence and/or amount of the complex indicates the presence and/or amount of the CsA in the sample.

The phrase "measuring the amount of a CsA analyte" refers to the quantitative, semiquantitative and qualitative determination of the CsA analyte. Methods that are quantitative, semiquantitative and qualitative, as well as all other methods for determining the CsA analyte, are considered to be methods of measuring the amount of the CsA analyte. For example, a method, which merely detects the presence or absence of the CsA analyte in a sample suspected of containing the CsA analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of the CsA in the sample. The particular mode of detection depends on the nature of the sps. As discussed above, there are numerous methods by which a label of an sps can produce a signal detectable by external means, desirably by visual examination, and include, for example, electromagnetic radiation, electrochemistry, heat, radioactivity detection, chemical reagents and so forth.

Activation of a signal producing system depends on the nature of the signal producing system members. For an sps member that is a sensitizer that is activated by light, the sps member is irradiated with light. Other activation methods will be suggested to those skilled in the art in view of the disclosures herein.

The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the CsA compound present in a sample. Temperatures during measurements generally range from about 10° to about 70° C., or from about 20° to about 45° C., or about 20° to about 25° C. In one approach standard curves are formed using known concentrations of the analytes to be screened. As discussed above, calibrators and other controls may also be used.

When a photosensitizer is used, the photosensitizer serves to activate the chemiluminescent composition when the medium containing the above reactants is irradiated. The medium is irradiated with light having a wavelength of sufficient energy to convert the photosensitizer to an excited state and render it capable of activating molecular oxygen to singlet oxygen. When bound to an sbp member, the photosensitizer concentration may be very low, frequently about $10^{-6}$ to about $10^{-12}$ M or lower. Generally, for the above embodiments involving a photosensitizer, the medium is irradiated with light having a wavelength of about 300 to about 1200 nm, or about 450 to about 950, or about 550 to about 800 nm.

The period of irradiation will depend on the lifetime of the activated chemiluminescent composition, the light intensity and the desired emission intensity. For short-lived activated chemiluminescent compositions, the period may be less than a second, usually about a millisecond but may be as short as a microsecond where an intense flashlamp or laser is used. For longer-lived activated chemiluminescent compositions, the irradiation period can be longer and a less intense steady light source can be used. In general, the integrated light intensity over the period of irradiation should be sufficient to excite at least 0.1% of the photosensitizer molecules, preferably at least 30%, and, most preferably, every photosensitizer molecule will be excited at least once.

The luminescence or light produced in any of the above approaches can be measured visually, photographically, actinometrically, spectrophotometrically or by any other convenient means to determine the amount thereof, which is related to the amount of analyte in the medium.

A helium-neon laser is an inexpensive light source for excitation at 632.6 nm. Photosensitizers that absorb light at this wavelength are compatible with the emission line of a helium-neon laser and are, therefore, particularly useful in the present methods in which photosensitizers are employed. Other light sources include, for example, other lasers such as Argon, YAG, He/Cd, and ruby; photodiodes; mercury, sodium and xenon vapor lamps; incandescent lamps such as tungsten and tungsten/halogen; and flashlamps.

Specific Embodiments of Assays

As mentioned above, in one embodiment of a method for determining the presence and/or amount of CsA in a medium suspected of containing CsA, a combination is provided in a medium wherein the combination comprises (i) the sample, (ii) a photosensitizer associated with a first particle and being capable of generating singlet oxygen wherein the first particle comprises a biotin-binding partner, (iii) a conjugate of cyclosporin A and biotin, and (iv) a chemiluminescent composition activatable by singlet oxygen and associated with a second particle wherein the second particle comprises an antibody for cyclosporin A. The combination is subjected to conditions for binding of cyclosporin A to the antibody for cyclosporin A. The photosensitizer is irradiated with light and the amount of luminescence generated by the chemiluminescent composition is detected, the presence and/or amount of luminescence being related to the amount of cyclosporin A in the sample.

Another embodiment of the present invention is a method for determining the presence and/or amount of cyclosporin A in a medium suspected of containing cyclosporin A. The method comprises providing in combination in a medium (i) the sample, (ii) a photosensitizer associated with a first particle and being capable of generating singlet oxygen wherein the first particle comprises a biotin binding partner, (iii) a chemiluminescent composition activatable by the singlet oxygen and associated with a second particle wherein the second particle comprises cyclosporin C and (iv) a conjugate of an antibody for cyclosporin A and biotin. The combination is subjected to conditions for binding of cyclosporin A, if present, to the antibody for cyclosporin A. The photosensitizer is irradiated with light and the amount of luminescence generated by the chemiluminescent composition is detected, the amount of luminescence being related to the presence and/or amount of cyclosporin A in the sample.

Reagents for Conducting the Specific Embodiments

In some embodiments the reagents for conducting an assay for CsA include a composition comprising cyclosporin C or cyclosporin A associated with a particle wherein the particle is associated with a chemiluminescent composition. Examples of such reagents are set forth in FIGS. 2 and 3 by way of illustration and not limitation. For the CsC-chemiluminescent particle, the particle is linked to a hydroxyl group of the ethylene group at position 2 of CsC by means of a linking group that comprises:

—C(O)NH(($CH_2$)$_2$O)$_n$($CH_2$)$_m$NH—(C(O)($CH_2$)$_p$C(O))$_q$— wherein n is 1 to 4, or 1 to 3, or 1 to 2, or 2 to 4, or 2 to 3, or 3 to 4 and m is 1 to 3, or 1 to 2 or 2 to 3 and p is 1 to 4, or 1 to 3, or 1 to 2, or 2 to 4, or 2 to 3, or 3 to 4 and q is 0 or 1. In some embodiments n is 2, m is 2 and q is 0 (p, therefore, being 0). In some embodiments n is 2, m is 2, p is 3 and q is 1. The particular linking group employed depends on the nature of the surface of the particle. In some embodiments the particle comprises a coating that possesses aldehyde groups such as, for example, dextran aldehyde (dexal) and the like and the linking group is as described above where q is 0 so that the terminal amine functionality of the linking group is reacted with the aldehyde functionality by reductive amination to give the desired CsC-particle reagent. In some embodiments the surface of the particle comprises a coating with amine functionalities such as, for example, aminodextran and the like, and the linking group is as described above where q is 1 so that the terminal carboxyl group of the linking group is reacted with the amine functionality of the particle to produce an amide linkage. In the above embodiments, the reagents have the formula:

—CsC-C(O)NH(($CH_2$)$_2$O)$_n$($CH_2$)$_m$NH—(C(O)($CH_2$)$_p$C(O))$_q$-chemiluminescent particle where n, m, p and q are as defined above.

For the CsA-chemiluminescent particle, the particle is linked to an amide nitrogen of CsA at position 7 or position 8 by means of a linking group that comprises:

—($CH_2$)$_s$OC(O)NH(($CH_2$)$_2$O)$_n$($CH_2$)$_m$NH—(C(O)($CH_2$)$_p$C(O))$_q$NH-(protein)$_t$-(NH)$_r$— wherein s is 1 to 3, or 2 to 3, or 1 to 2, and n is 1 to 4, or 1 to 3, or 1 to 2, or 2 to 4, or 2 to 3, or 3 to 4 and m is 1 to 3, or 1 to 2 or 2 to 3 and p is 1 to 4, or 1 to 3, or 1 to 2, or 2 to 4, or 2 to 3, or 3 to 4 and q is 0 or 1 and t is 0 or 1 and r is 0 or 1. Protein may be bovine gamma globulin (BgG), IgG and the like. In some embodiments s is 2, n is 2, m is 2, q is 0 (thus, p is not present), t is 0 and r is 0. In some embodiments s is 2, n is 2, m is 2, p is 3, q is 1, t is 0 and r is 0. In some embodiments s is 2, n is 2, m is 2, p is 3, q is 1, t is 1 and r is 1 and protein is BgG. The particular linking group employed depends on the nature of the surface of the particle. In some embodiments the particle comprises a coating that possesses aldehyde groups such as, for example, dexal and the like and the linking group is as described above where q is 0, t is 0 and r is 0 or where q is 1, t is 1 and r is 1, so that the terminal amine functionality of the linking group is reacted with the aldehyde functionality by reductive amination to give the desired CsA-chemiluminescent particle reagent. In some embodiments the surface of the particle comprises a coating with amine functionalities such as, for example, aminodextran and the like, and the linking group is as described above where q is 1, t is 0 and r is 0 so that the terminal carboxyl group of the linking group is reacted with the amine functionality of the particle to produce an amide linkage. In the above embodiments the reagents have the formula:

CsA-($CH_2$)$_s$OC(O)NH(($CH_2$)$_2$O)$_n$($CH_2$)$_m$NH—(C(O)($CH_2$)$_p$C(O))$_q$NH-(protein)$_t$-(NH)$_r$—chemiluminescent particle where s, n, m, p, q, t, and r are as defined above.

In some embodiments, the reagents for conducting an assay for CsA include a composition comprising biotin conjugated to an antibody for CsA (AbCsA). Examples of such AbCsA-biotin reagents are set forth in FIG. 4 by way of illustration and not limitation. Biotin is linked to the antibody employing the carboxylic acid functionality of the biotin and amine functionalities of the antibody. The linking group comprises:

—C(O)NH(($CH_2$)$_2$O)$_u$($CH_2$)$_v$NH— wherein u is 0 to 5, or 1 to 5, or 2 to 5, or 3 to 5 or 4 to 5, or 0 to 4, or 1 to 4, or 2 to 4, or 3 to 4, or 0 to 3, or 1 to 3, or 2 to 3, or 0 to 2 or 1 to 2, or 0 to 1 and v is 1 to 6, or 2 to 6, or 3 to 6, or 4 to 6, or 5 to 6, or 1 to 5, or 2 to 5, or 3 to 5, or 4 to 5, or 1 to 4, or 2 to 4, or 3 to 4, or 1 to 3, or 2 to 3, or 1 to 2. In some embodiments u is 4, and v is 2. In some embodiments u is 0, v is 5. In the above embodiments, the reagents have the formula:

AbCsA-C(O)NH(($CH_2$)$_2$O)$_u$($CH_2$)$_v$NH-biotin where u and v are as defined above.

In some embodiments the reagents include biotin, including bis-biotin, conjugated to CsA at an amide nitrogen at position 7 or position 8 employing the carboxylic acid functionality of the biotin. Examples of such reagents are set forth in FIGS. 6-7 by way of illustration and not limitation. In some embodiments, the linking group comprises:

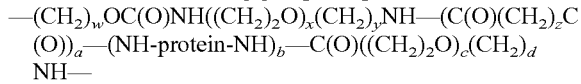

wherein w is 1 to 3, or 2 to 3, or 1 to 2, and x is 1 to 4, or 1 to 3, or 1 to 2, or 2 to 4, or 2 to 3, or 3 to 4, and y is 1 to 3, or 1 to 2 or 2 to 3, and z is 1 to 4, or 1 to 3, or 1 to 2, or 2 to 4, or 2 to 3, or 3 to 4, and a is 0 or 1, and b is 0 or 1, and c is 1 to 6, or 2 to 6, or 3 to 6, or 4 to 6, or 5 to 6, or 1 to 5, or 2 to 5, or 3 to 5, or 4 to 5, or 1 to 4, or 2 to 4, or 3 to 4, or 1 to 3, or 2 to 3, or 1 to 2, and d is 1 to 3, or 2 to 3, or 1 to 2. In some embodiments w is 2, x is 2, y is 2, z is 3, a is 1, b is 1, c is 4 and d is 2 and protein is bovine gamma globulin (BgG). In some embodiments w is 2, x is 2, y is 2, z is 3, a is 0, b is 0, c is 4 and d is 2. In the above embodiments the reagents have the formula:

CsA-(CH$_2$)$_w$OC(O)NH((CH$_2$)$_2$O)$_x$(CH$_2$)$_y$NH—(C(O)(CH$_2$)$_z$C(O))$_a$—(NH-protein-NH)$_b$—C(O)((CH$_2$)$_2$O)$_c$(CH$_2$)$_d$NH-biotin where w, x, y, z, a, b, c and d are as defined above.

Examples of CsA-bis-biotin reagents are set forth in FIG. 8 by way of illustration and not limitation. In some embodiments, the linking group comprises:

—(CH$_2$)$_e$OC(O)NH(CH$_2$)$_f$C(O)NH((CH$_2$)$_2$O)$_g$(CH$_2$)$_h$NHC(O)D wherein D is

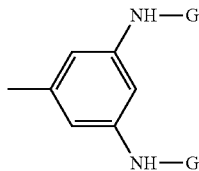

wherein G is —C(O)(CH$_2$)$_j$NH— wherein e is 1 to 3, or 2 to 3, or 1 to 2, and f is 1 to 3, or 1 to 2, or 2 to 3, and g is 1 to 4, or 1 to 3, or 1 to 2, or 2 to 4, or 2 to 3, or 3 to 4, and h is 1 to 3, or 1 to 2 or 2 to 3, and j is 1 to 6, or 2 to 6, or 3 to 6, or 4 to 6, or 5 to 6, or 1 to 5, or 2 to 5, or 3 to 5, or 4 to 5, or 1 to 4, or 2 to 4, or 3 to 4, or 1 to 3, or 2 to 3, or 1 to 2. In some embodiments e is 2, f is 1, g is 2, h is 2 and j is 5. In the above embodiments the reagents have the formula:

CsA-(CH$_2$)$_e$OC(O)NH(CH$_2$)$_f$C(O)NH((CH$_2$)$_2$O)$_g$(CH$_2$)$_h$NHC(O)D wherein D is

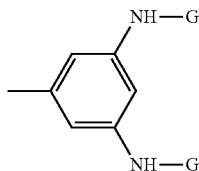

wherein G is —C(O)(CH$_2$)$_j$NH-biotin
wherein e, f, g, h and j are as defined above.

In some embodiments the reagents include a conjugate of CsC and biotin. Examples of such reagents are set forth in FIG. 9 by way of illustration and not limitation. In some embodiments the linking group linking CsC and biotin employing the hydroxyl group on the ethylene group at position 2 of CsC comprises:

—C(O)NH((CH$_2$)$_2$O)$_x$(CH$_2$)$_y$NH—(C(O)(CH$_2$)$_z$C(O))$_a$—(NH-protein-NH)$_b$—C(O)((CH$_2$)$_2$O)$_c$(CH$_2$)$_d$NH— wherein w' is 1 to 3, or 2 to 3, or 1 to 2, and x' is 1 to 4, or 1 to 3, or 1 to 2, or 2 to 4, or 2 to 3, or 3 to 4, and y' is 1 to 3, or 1 to 2 or 2 to 3, and z' is 1 to 4, or 1 to 3, or 1 to 2, or 2 to 4, or 2 to 3, or 3 to 4, and a' is 0 or 1, and b' is 0 or 1, and c' is 1 to 6, or 2 to 6, or 3 to 6, or 4 to 6, or 5 to 6, or 1 to 5, or 2 to 5, or 3 to 5, or 4 to 5, or 1 to 4, or 2 to 4, or 3 to 4, or 1 to 3, or 2 to 3, or 1 to 2, and d' is 1 to 3, or 2 to 3, or 1 to 2. In some embodiments x' is 2, y' is 2, z' is 3, a' is 1, b' is 1, c' is 4 and d' is 2 and protein is BgG. In the above embodiments the reagents have the formula:

CsC-C(O)NH((CH$_2$)$_2$O)$_{x'}$(CH$_2$)$_{y'}$NH—(C(O)(CH$_2$)$_{z'}$C(O))$_{a'}$—(NH-protein-NH)$_{b'}$—C(O)((CH$_2$)$_2$O)$_{c'}$(CH$_2$)$_{d'}$NH-biotin where x', y', z', a', b', c' and d' are as defined above.

Preparation of Reagents

The following synthetic schemes are directed to specific embodiments by way of illustration and not limitation. It will be appreciated that similar reagents may be prepared by means of the reactions described below.

Preparation of CsC-Chemiluminescent Particle: an Embodiment of the Preparation of this reagent is illustrated in FIG. 10, Scheme 1, and FIG. 11, Scheme 2. The preparation of CsC-DA-10-EPRM chemibead (4) as the CsC-chemiluminescent particle reagent is discussed by way of illustration and not limitation. The hydroxy group of CsC (2) is activated employing a suitable activation agent reactive with the hydroxyl of the ethylene group at position 2 of CsC, such as, for example, disuccinimidyl carbonate (DSC) and the like. The activated CsC intermediate is reacted with diamine linking group reagent DA-10 (—NH((CH$_2$)$_2$O)$_2$(CH$_2$)$_2$NH—) to give CsC derivative (3) (FIG. 10, Scheme 1). The reaction is carried out at a temperature of about 0 to about 40° C., for a period of about 8 to about 24 hours under basic conditions at a pH of about 7 to about 13, or about 8 to about 11, such as, for example, in the presence of triethyl amine (Et$_3$N), diisopropyl ethyl amine, potassium carbonate, sodium carbonate, sodium hydroxide and the like in an organic solvent such as, for example, a nitrile, e.g., acetonitrile (AcCN), etc., an ether, e.g., THF, diethyl ether, etc., DMF, DMSO, and the like. Compound (3) is attached to the EPRM chemibead (polystyrene with chelated europium and thioxene as the chemiluminescent composition) with a reductive amination (for example, in the presence of, for example, sodium cyanoborohydride, or the like) in buffer to generate the CsC-DA-10-EPRM chemibead (4) (FIG. 11, Scheme 2).

The EPRM chemibead is prepared in a manner similar to the method described in U.S. Pat. No. 6,153,442 and U.S. Patent Application Publication No. 20050118727A, the relevant disclosures of which are incorporated herein by reference. The EPRM chemibead comprises an aminodextran inner layer and a dexal outer layer having free aldehyde functionalities. Dexal is dextran aldehyde; see, for example, U.S. Pat. Nos. 5,929,049 and 7,172,906. The reaction is carried out at a temperature of about 0 to about 40° C., for a period of about 16 to about 64 hours at a pH of about 5.5 to about 7.0, or about 6, in a buffered aqueous medium employing a suitable buffer such as, for example, MES or the like. The reaction is quenched by addition of a suitable quenching agent such as, for example, carboxymethoxyoxime (CMO), or the like and subsequent washing of the particles.

Figure 12:
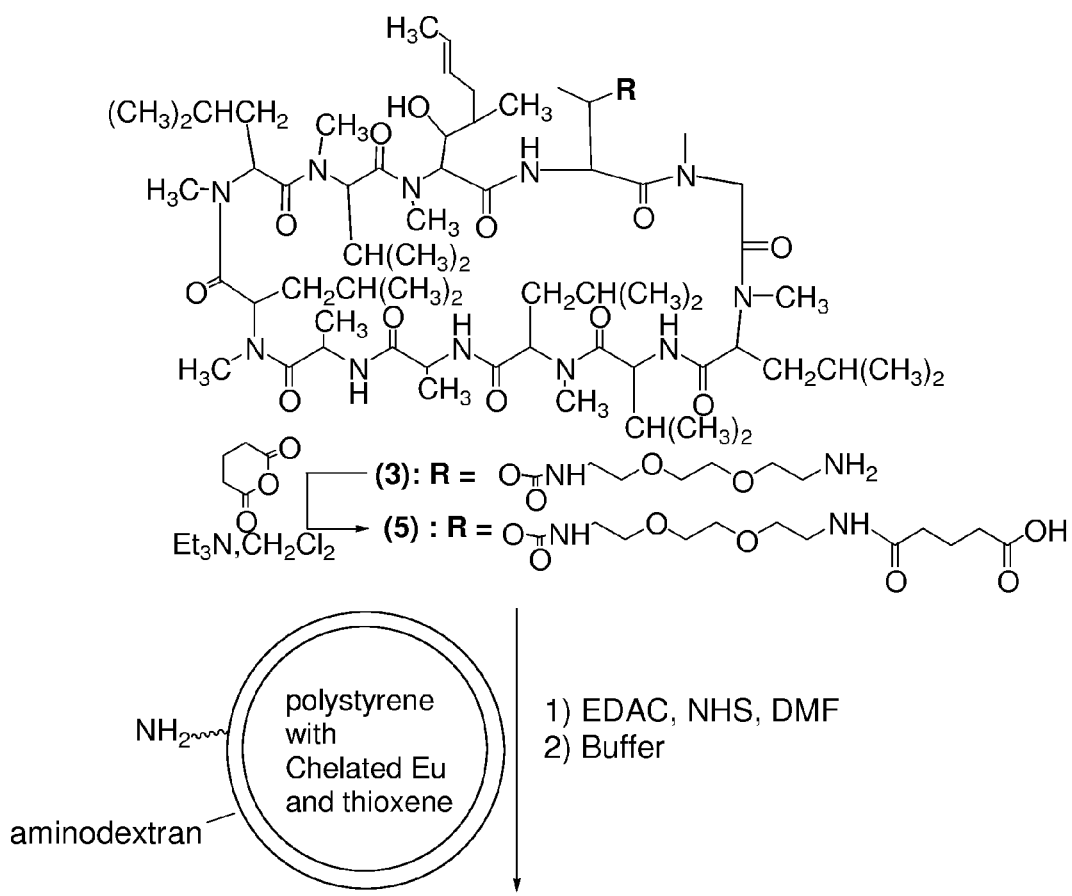
FIG. 12 is a depiction of the preparation of another reagent comprising cyclosporin C linked to a chemiluminescent particle.
Figure 12:
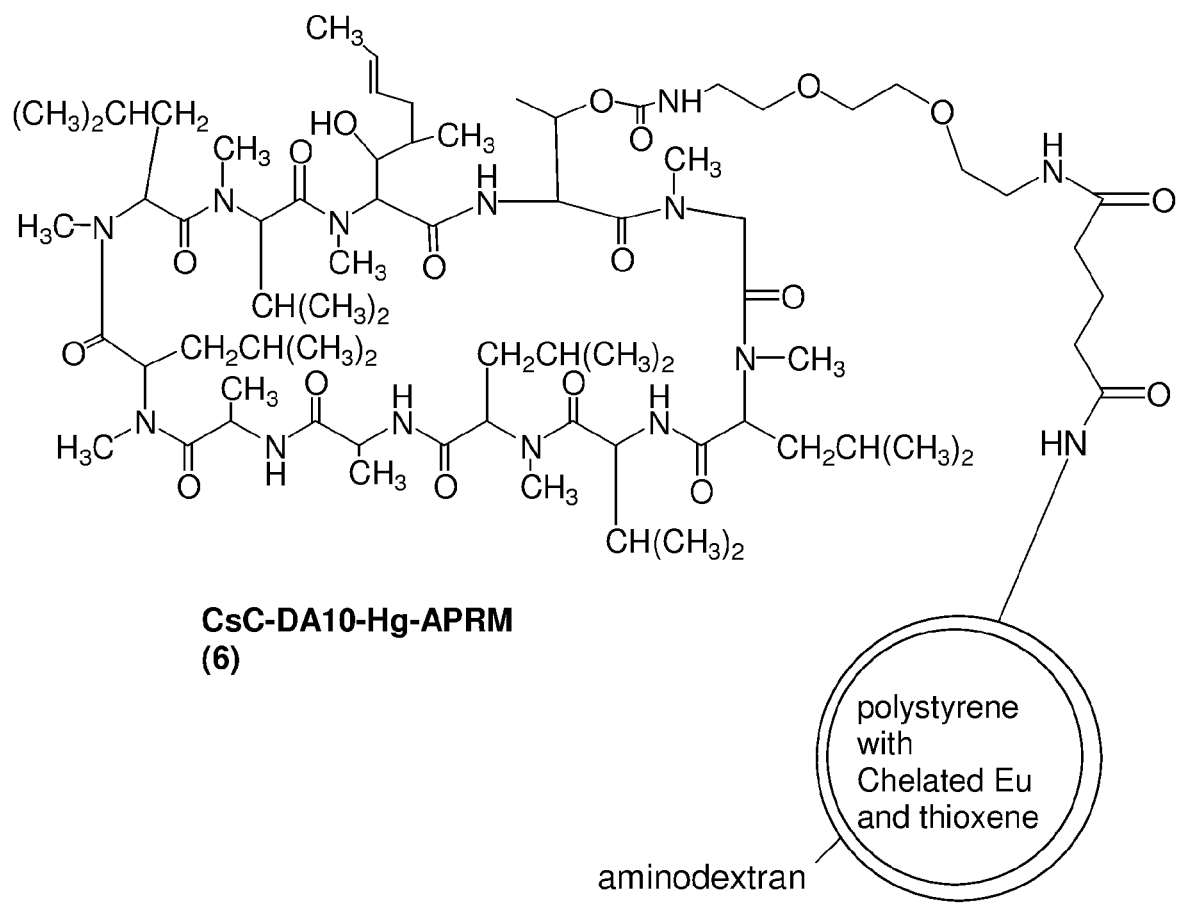

Another embodiment of the preparation of CsC-chemiluminescent particle is illustrated by way of example in FIG. 12, Scheme 3. Compound 3 is treated to introduce a carboxylic acid group on the terminal amine group of the DA-10 moiety. In one embodiment, reaction of 3 with glutaric anhydride under basic conditions introduces an acid group to the CsC molecule to give CsC-Carbamate (5) (FIG. 12, Scheme 3).

The acid (5) is then activated by means of a suitable activation agent such as, for example, 1-ethyl-3-(3-dimethylaminopropyl)-carbodiimide hydrochloride (EDAC) and N-hydroxysuccinimidyl (NHS) ester, dicyclohexylcarbodiimide (DCC) or the like in an organic solvent such as, for example, dimethylformamide (DMF), THF, dichloromethane, AcCN or the like. A buffer such as, for example, sodium phosphate or the like is added to adjust the pH to about 7.0 to about 8.0 together with an APRM chemibead with free amine groups on its surface to give CsC-DA-10-Hg-APRM (6) (FIG. 12, Scheme 3). The APRM chemibead is a polystyrene bead with chelated europium and thioxene as the chemiluminescent composition. The APRM chemibead is prepared in a manner similar to the method described in U.S. Pat. No. 6,153,442, the relevant disclosure of which is incorporated herein by reference. The APRM chemibead comprises an aminodextran layer having free amine functionalities. The reaction is carried out at a temperature of about 0 to about 40° C., for a period of about 8 to about 24 hours.

Figure 13:
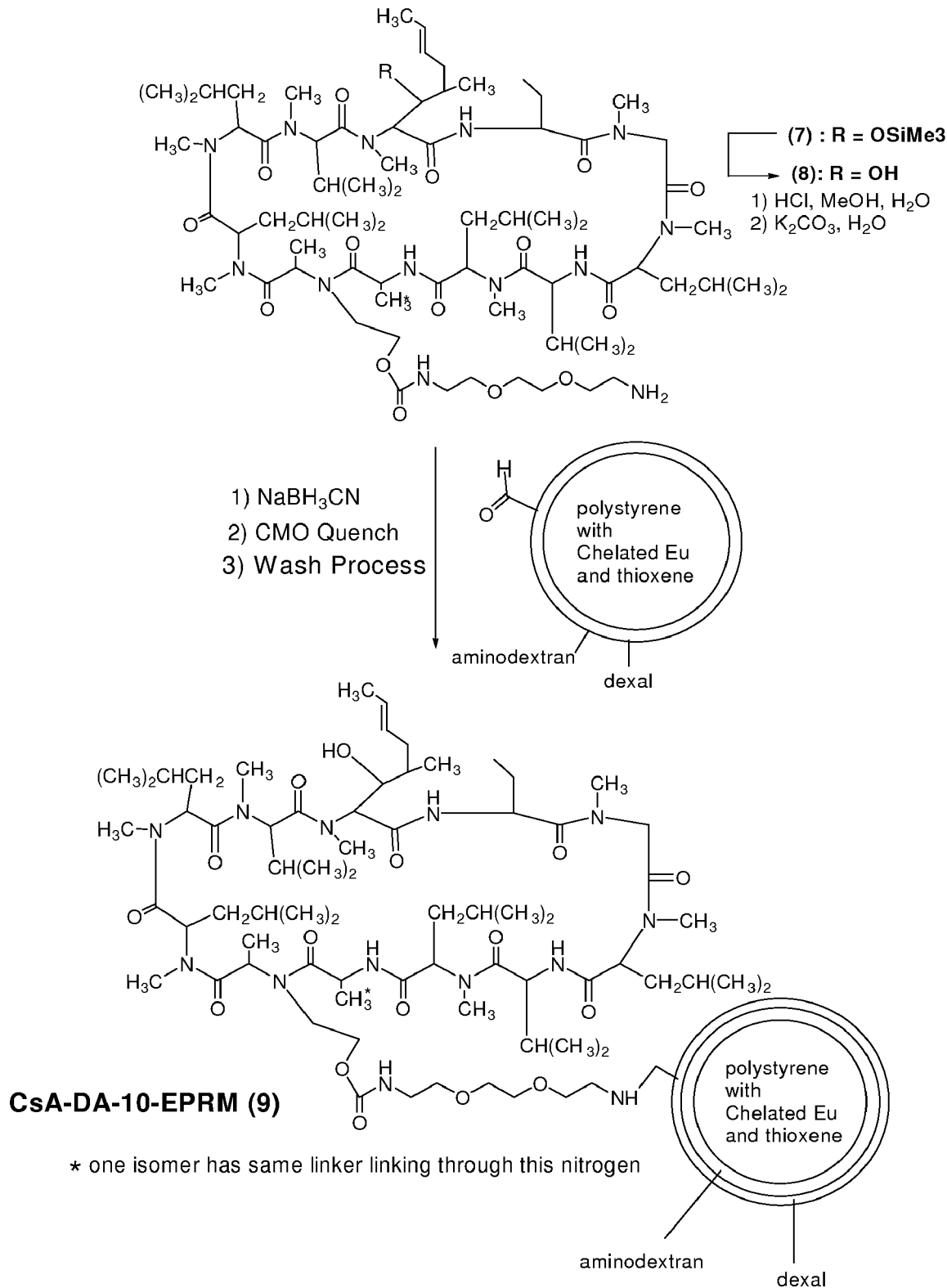
FIG. 13 is a depiction of the preparation of a reagent comprising cyclosporin A linked to a chemiluminescent particle.

Preparation of CsA-chemiluminescent particle: an Embodiment of the Preparation of this reagent is illustrated in FIG. 13, Scheme 4. The preparation of CsA-DA-10-EPRM chemibead (9) as the CsA-chemiluminescent particle reagent is discussed by way of illustration and not limitation. CsA derivative (7) is prepared as described in U.S. Pat. No. 6,054,303. The removal of the silicon protecting group on CsA-DA-10 (7) is performed using either basic conditions or acidic conditions to give compound (8). Basic conditions include, for example, potassium carbonate, sodium carbonate, or the like in an aqueous medium. The acidic conditions include dilute acid such as, for example, mineral acids, e.g., HCl, sulfuric acid, etc., or the like in an aqueous organic solvent such as, for example, water/alcohol, where the alcohol may be, for example, methanol, ethanol, etc., or the like, water/ether where the ether is water soluble to the extent necessary, and so forth. The reaction is carried out at a temperature of about 0 to about 40° C., for a period of about 8 to about 24 hours. Attachment of 8 to the chemibeads is achieved by reductive amination followed by quenching and washing such as discussed above to give CsA-DA-10-EPRM chemibead (9).

Figure 14:
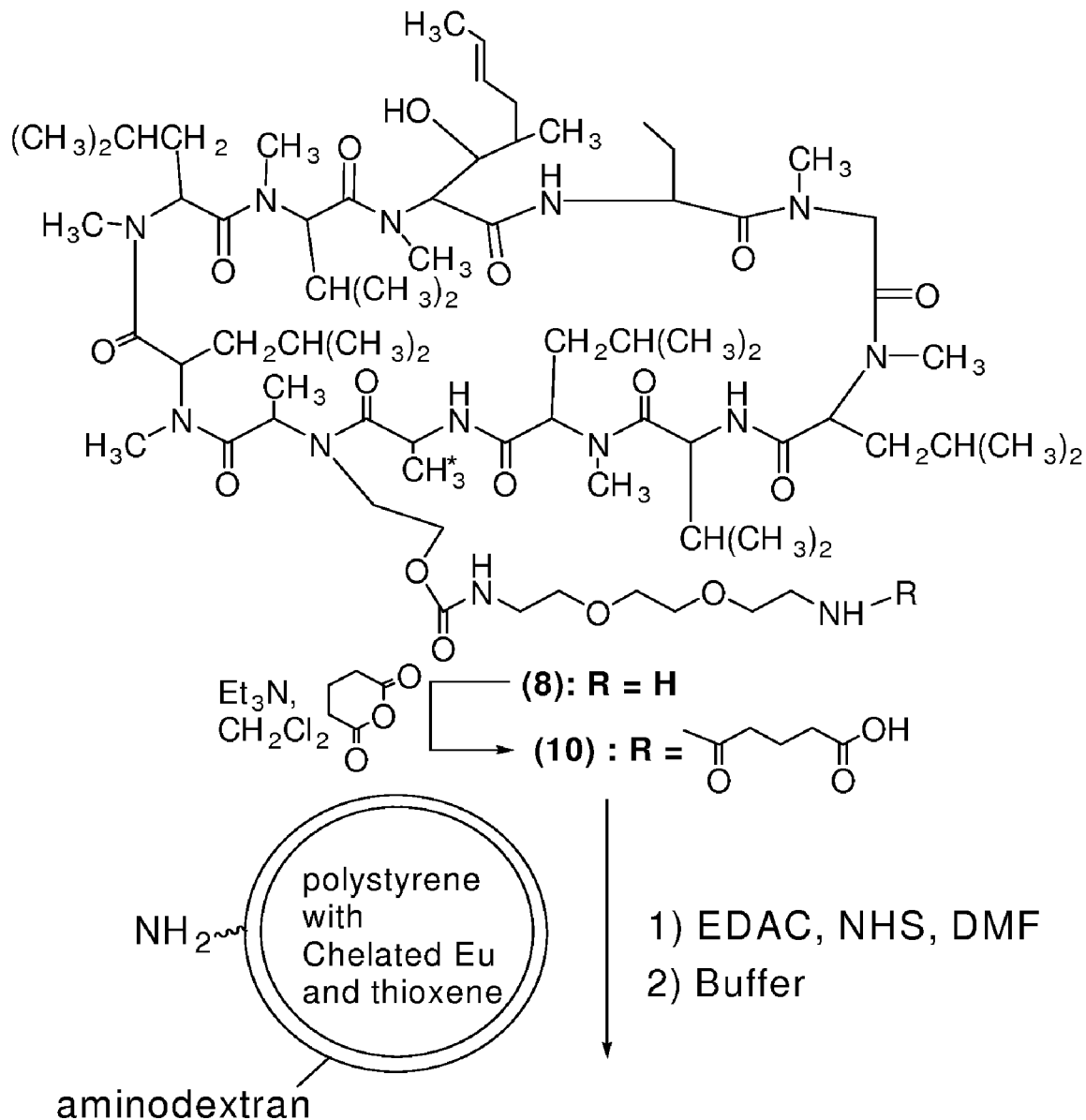
FIG. 14 is a depiction of the preparation of another reagent comprising cyclosporin A linked to a chemiluminescent particle.
Figure 14:
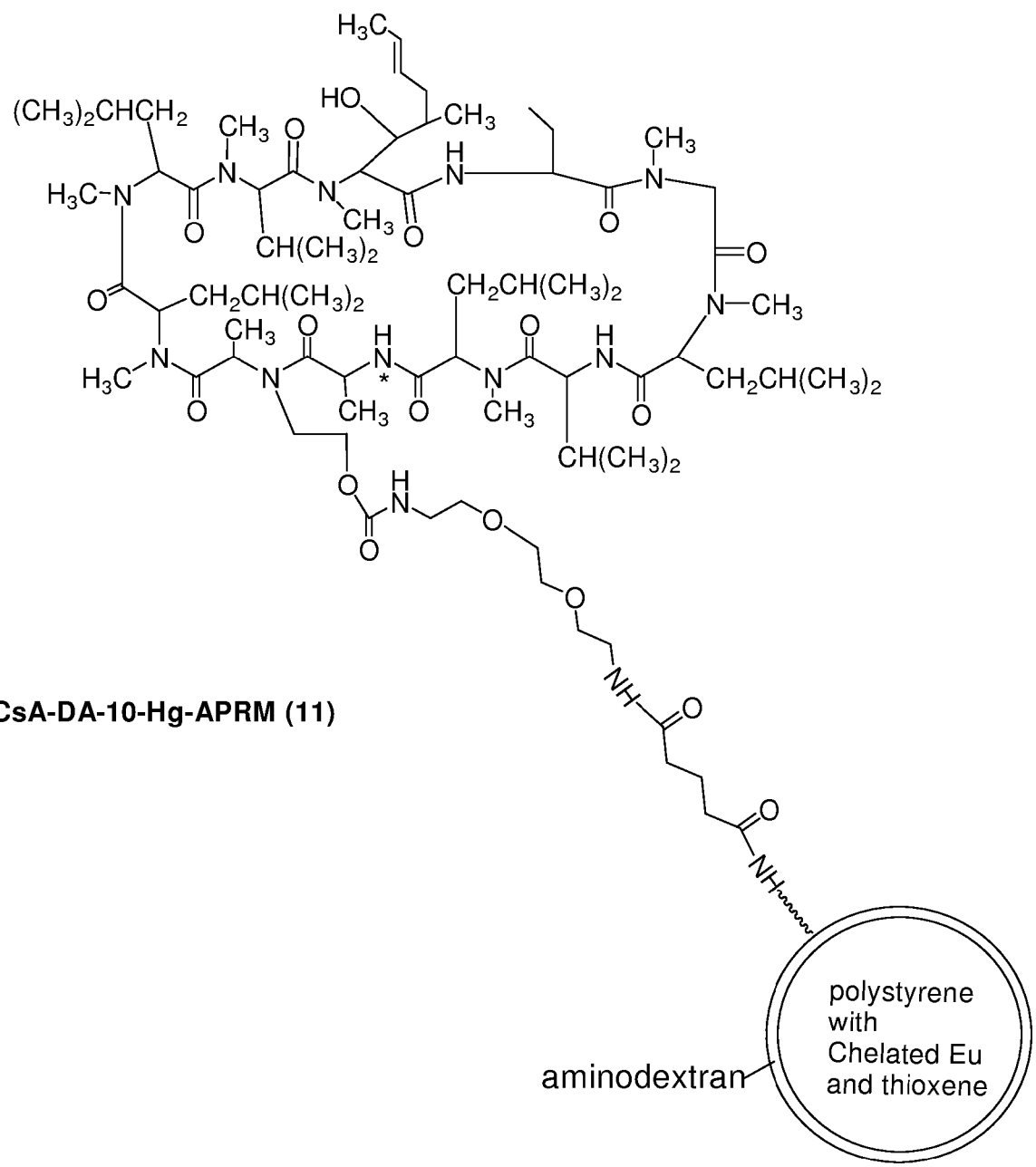

In another embodiment, the preparation of CsA-DA-10-Hg-APRM chemibead (11) as the CsA-chemiluminescent particle reagent is discussed by way of illustration and not limitation (FIG. 14, Scheme 5). Reaction of (8) with glutaric anhydride gives acid (10) under basic conditions such as, for example, an amine, e.g., triethyl amine, diisopropyl ethyl amine or the like in a suitable organic solvent such as, for example, methylene chloride, DMF, an ether, e.g., diethyl ether, etc., or the like (FIG. 14, Scheme 5). The reaction is carried out at a temperature of about 0 to about 40° C., for a period of about 1 to about 20 hours. An activated ester is formed from acid (10) employing an activation agent such as, for example, EDAC/NHS reagents to form a NHS ester, or the like. The reaction is carried out at a temperature of 0 to about 40° C., for a period of about 6 to about 24 hours. The resulting NHS ester is attached to the APRM chemibead by reaction of the free amine groups on the surface of the bead with the carboxylic acid functionality of acid (10) to give CsC-DA-10-Hg-APRM (11) where Hg is hemiglutamate.

Figure 15:
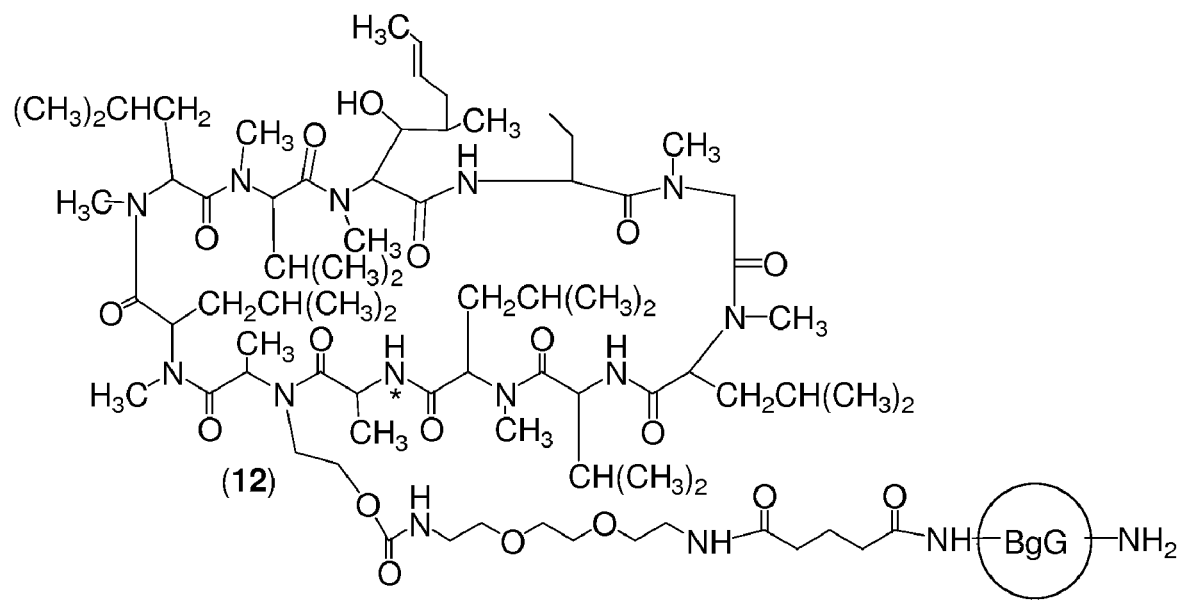
FIG. 15 is a depiction of the preparation of another reagent comprising cyclosporin A linked to a chemiluminescent particle.
Figure 15:
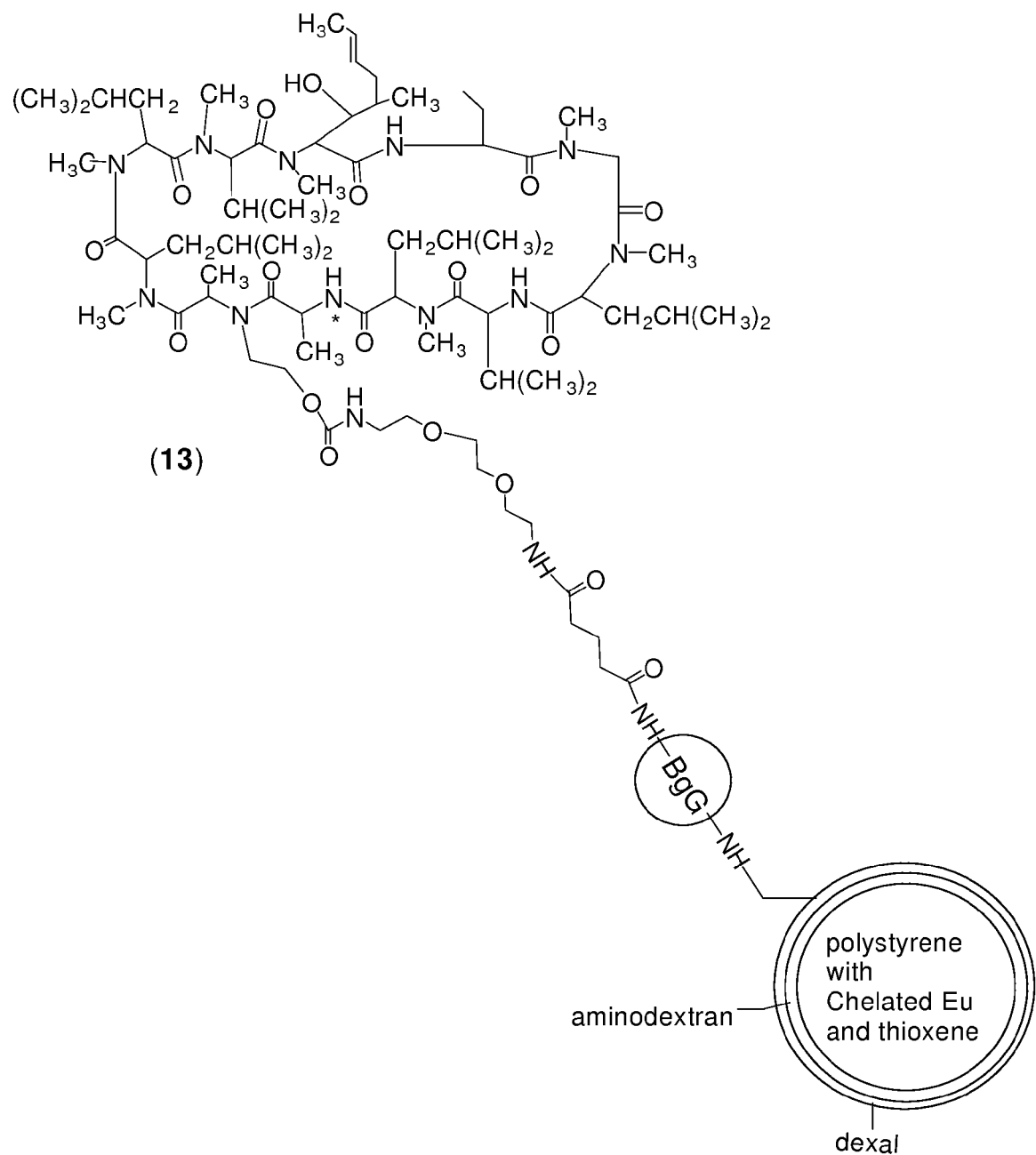

In another embodiment, the preparation of CsA-BgG-EPRM chemibead (13) as the CsA-chemiluminescent particle reagent is discussed by way of illustration and not limitation (FIG. 15, Scheme 6). CsA-BgG bio-conjugate (12) may be prepared in a manner similar to that discussed above for the preparation of compound (10) and further including the reaction of the terminal carboxylic acid with an amine functionality of BgG to form an amide linkage. The reaction of an amine functionality of BgG of the bio-conjugate (12) with the aldehyde of EPRM chemibead under reductive amination conditions followed by quenching and washing as described above gives the CsA-BgG-EPRM chemibead (13) (FIG. 15, Scheme 6).

Figure 16:
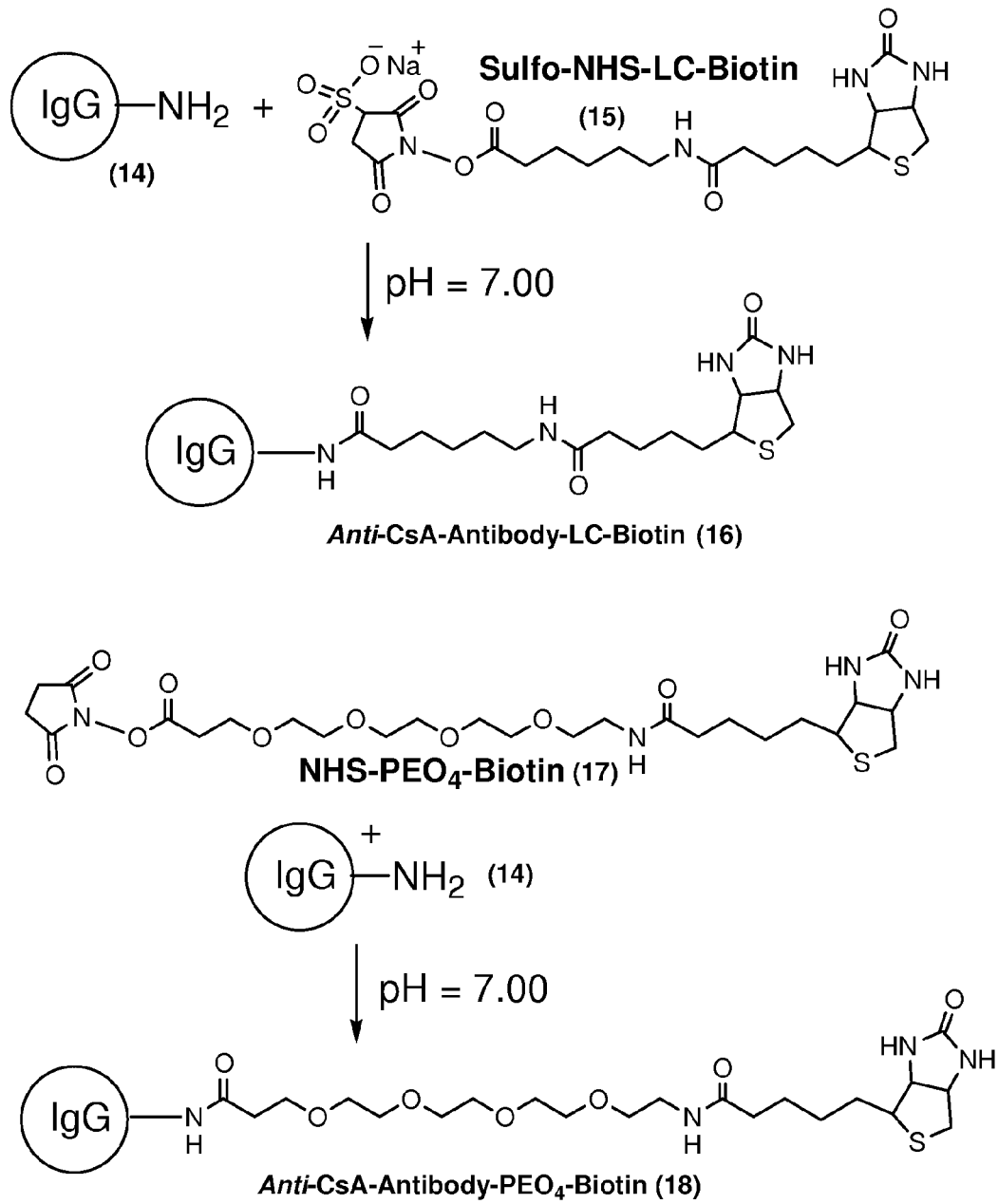
FIG. 16 is a depiction of the preparation of various conjugates of an antibody for cyclosporin A and biotin.

Preparation of CsA antibody-biotin reagent. The preparation of anti-CsA-LC-Biotin (16) and anti-CsA-PEO$_4$-biotin (18) as biotinylated CsA antibody reagents is discussed by way of illustration and not limitation (FIG. 16, Scheme 7). Monoclonal CsA antibody (14) may be biotinylated with a hydrophilic (sulfo-NHS-LC-Biotin) moiety or hydrophobic (NHS-PEO$_4$-Biotin) moiety. LC is an alkylene of 5 carbons although other alkylene groups may be employed such as, for example, alkylene of 3 to 8 carbons, or 4 to 7 carbons, or 4 to 6 carbons, and PEO$_4$ is four repeating ethylene oxide units (—((CH$_2$)$_2$O)$_4$—). The hydrophilic linker LC reagent and the hydrophobic linker reagent are available, for example, from Pierce (Woburn Mass.). The reactions employing the hydrophilic linker reagent or the hydrophobic linker reagent may be performed in neutral buffer such as, for example, sodium phosphate and sodium chloride, or the like. The reactions are carried out at a temperature of about 0 to about 40° C., for a period of about 1 to about 24 hours.

Figure 17:
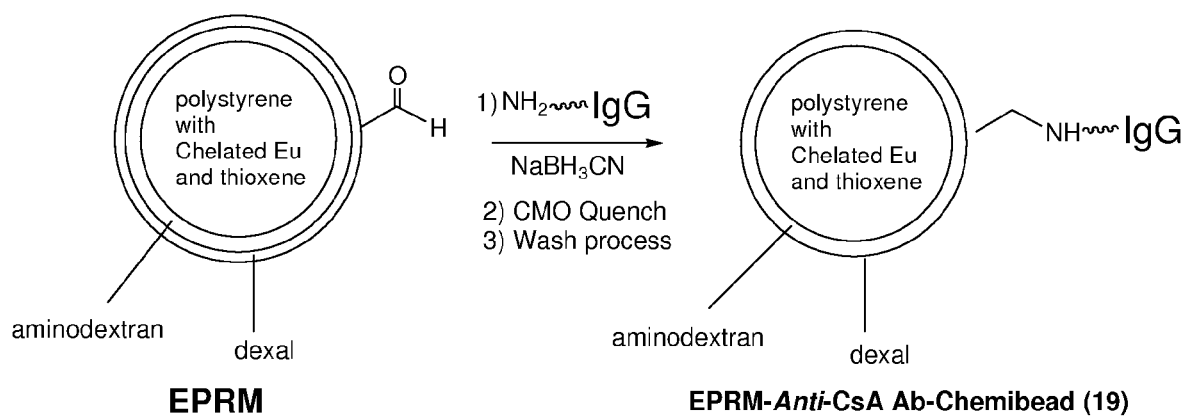
FIG. 17 is a depiction of the preparation of a conjugate of an antibody for cyclosporin A and a chemiluminescent particle.

Preparation of CsA antibody-chemiluminescent particle reagent. The Preparation of conjugates of CsA antibody and particles may be accomplished according to the following embodiments. For example, EPRM-anti-CsA-antibody-chemibead (19) is prepared in buffer (for example, MES, pH=6.0, neowater (83%) and MES buffer (50 mM), or the like) with reductive amination of free amine groups of the antibody with aldehyde groups of the EPRM chemibead in the presence of NaBH$_3$CN (FIG. 17, Scheme 8) under reductive amination conditions as discussed above. Any remaining aldehyde groups from ERPM are quenched as described above and the resulting particles are washed as discussed above.

Figure 18:
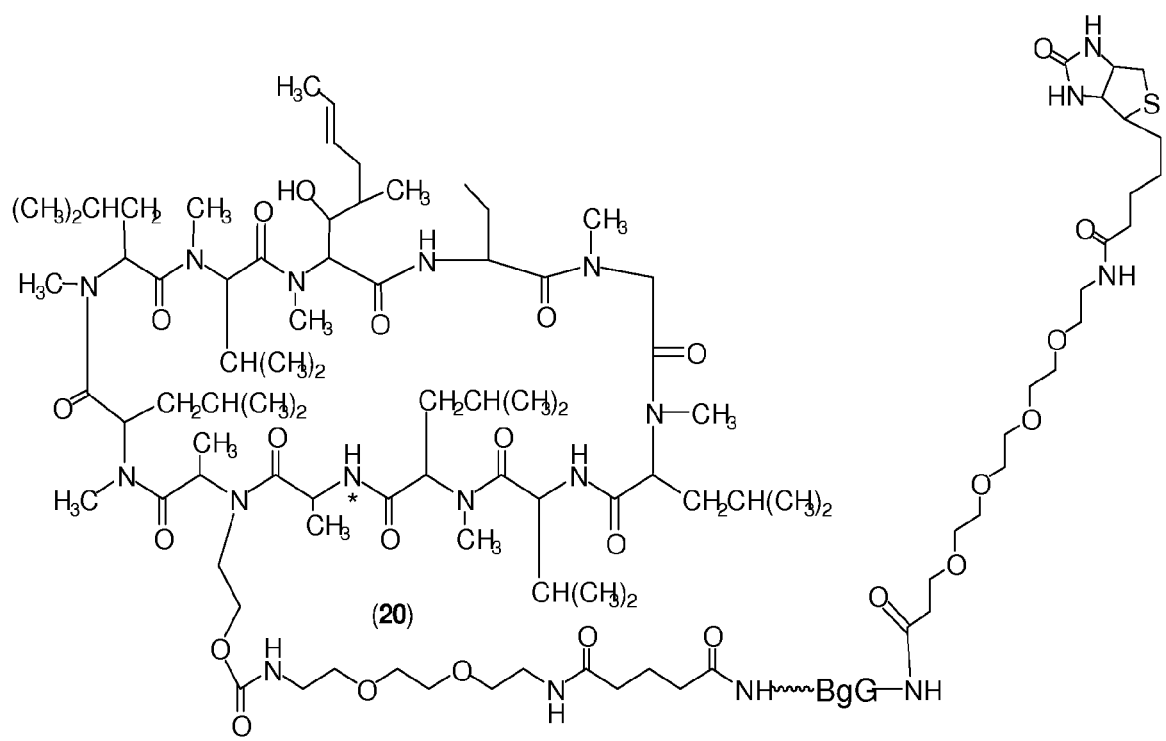
FIG. 18 is a depiction of the preparation of another conjugate of cyclosporin A and biotin.

Preparation of CsA-biotin conjugates with protein linker. In some embodiments, the free amine groups of the BgG of the CsA-BgG bio-conjugate (12), prepared as discussed above, are reacted with a suitable activated linking group such as, for example, an activated NHS ester linked to biotin by means of a PEO$_4$ linker (NHS-PEO$_4$-Biotin) to give CsA-DA-10-Hg-BgG-biotin (20) (FIG. 18, Scheme 9). The reaction is carried out at a temperature of about 0 to about 40° C., for a period of about 5 to about 24 hours at a pH of about 7.5 to about 9.5.

Figure 19:
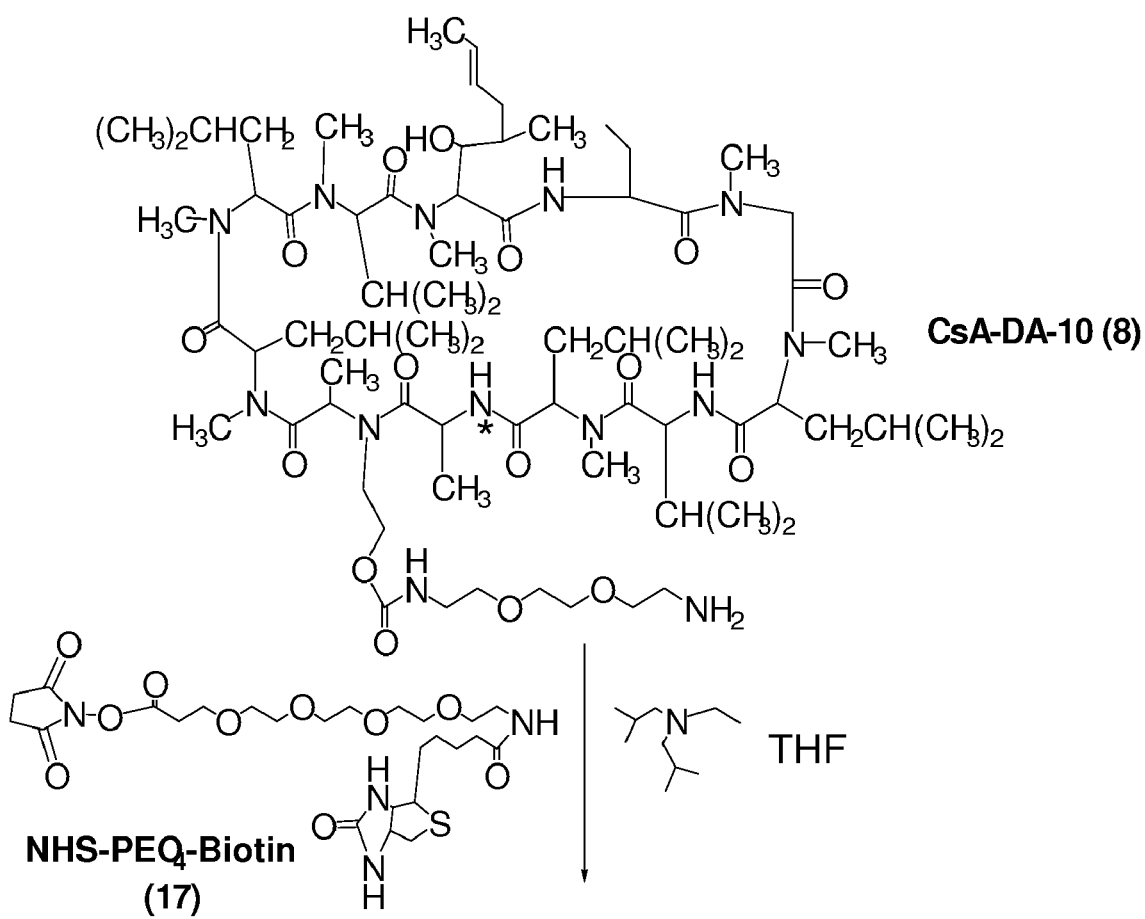
FIG. 19 is a depiction of the preparation of another conjugate of cyclosporin A and biotin.
Figure 19:
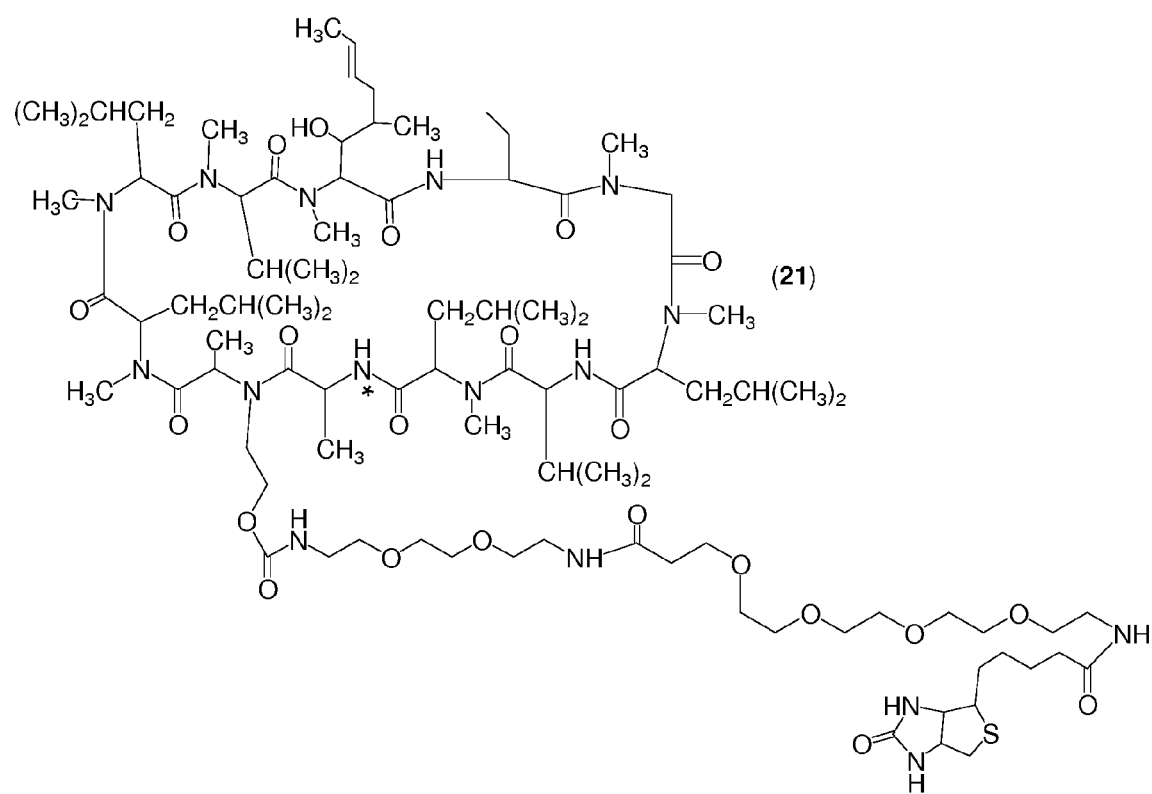

Preparation of CsA-biotin conjugates without protein linker. In some embodiments, direct biotinylation of CsA-DA-10 (8) with the linker, NHS-PEO$_4$-Biotin is accomplished without using protein linker to give CsA-DA-10-Biotin (21) (FIG. 19, Scheme 10). Compound (8) is obtained as described above. The reaction is carried out at a temperature of about 0 to about 40° C., for a period of about 2 to about 24 hours at a pH of about 7 to about 13. Various purification techniques such as, for example, preparative TLC (thin layer chromatography) may be employed to purify the derivative (21).

Figure 20:
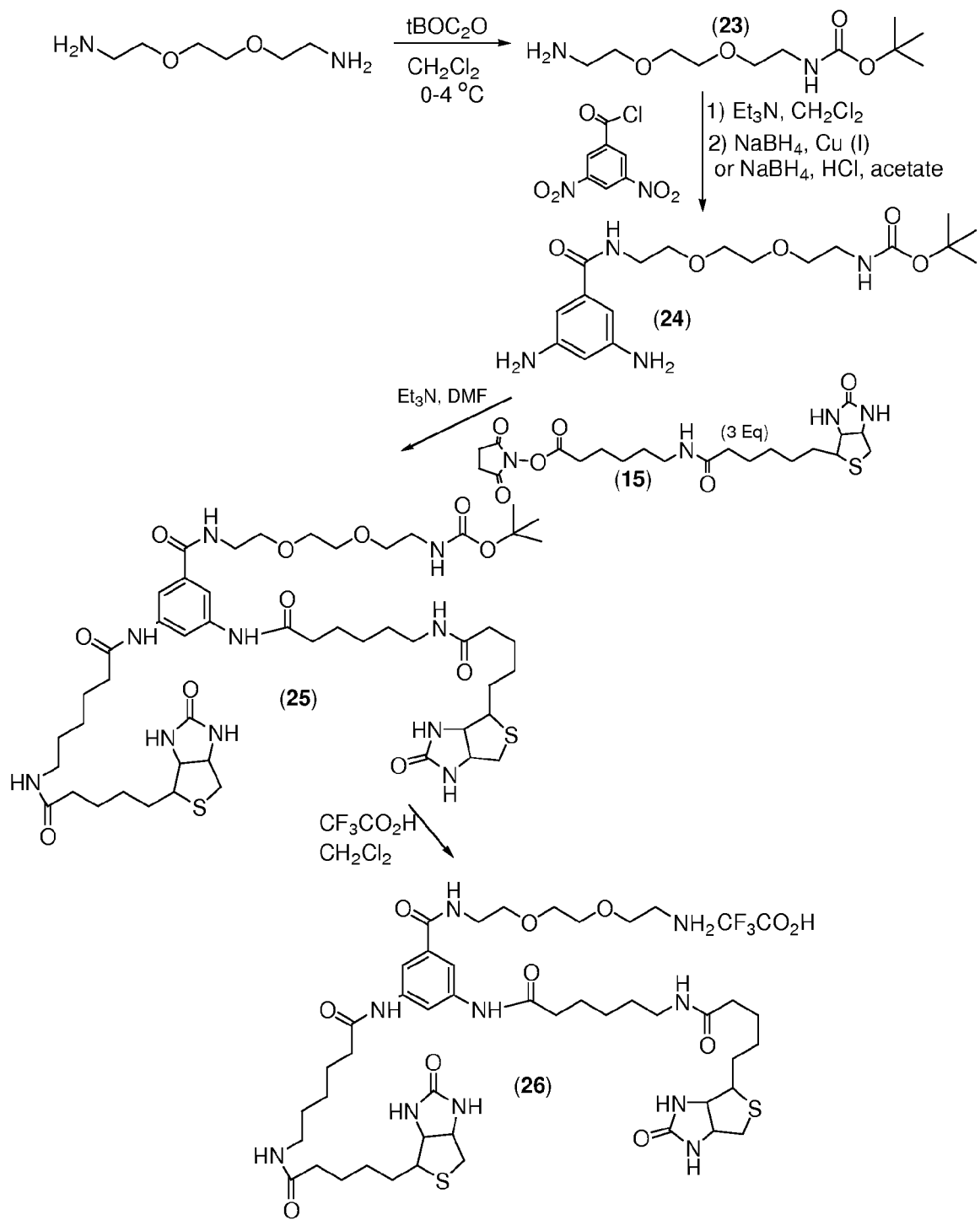
FIG. 20 is a depiction of the preparation of bis-biotin having a linking group.
Figure 21:
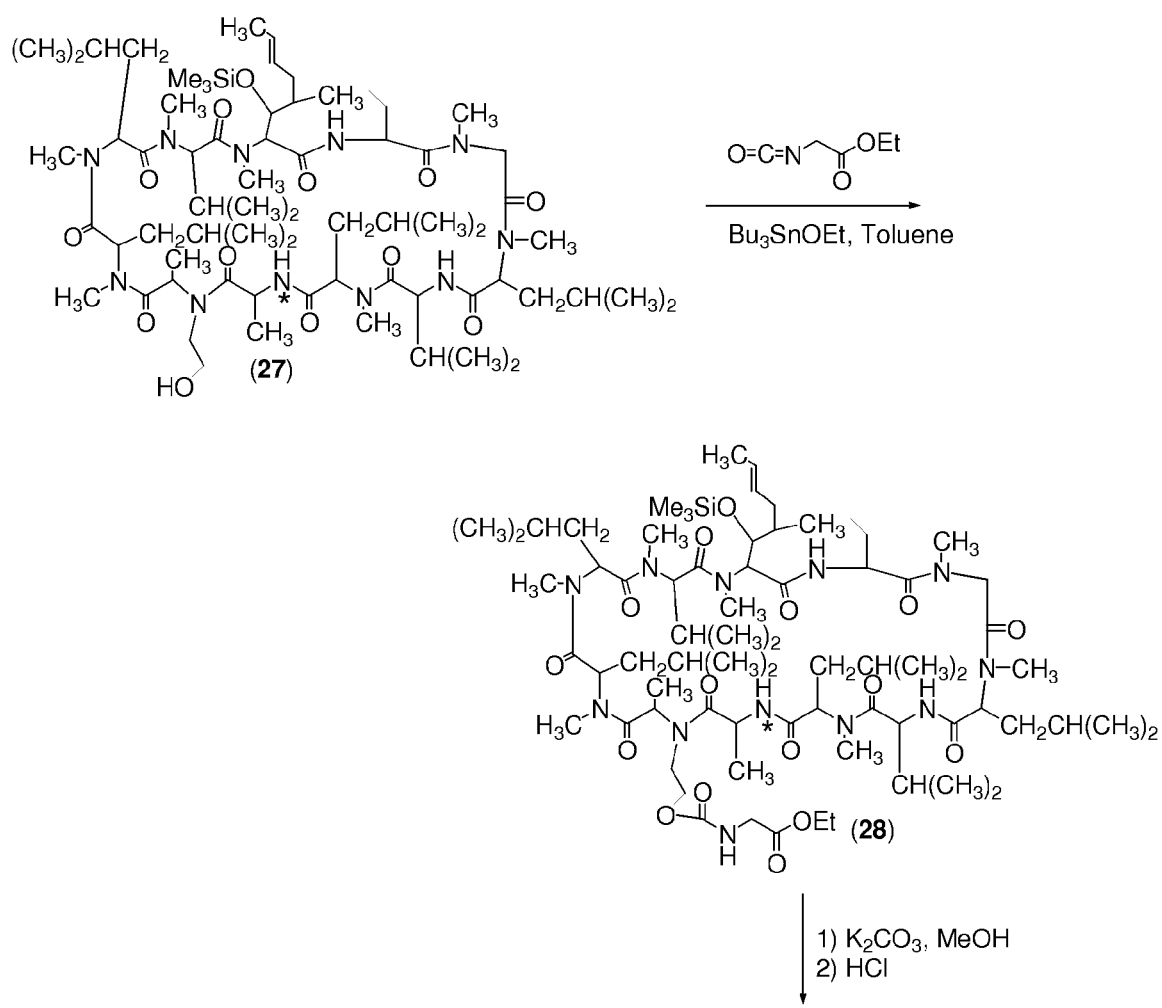
FIG. 21 is a depiction of the preparation of a cyclosporin A intermediate.
Figure 21:
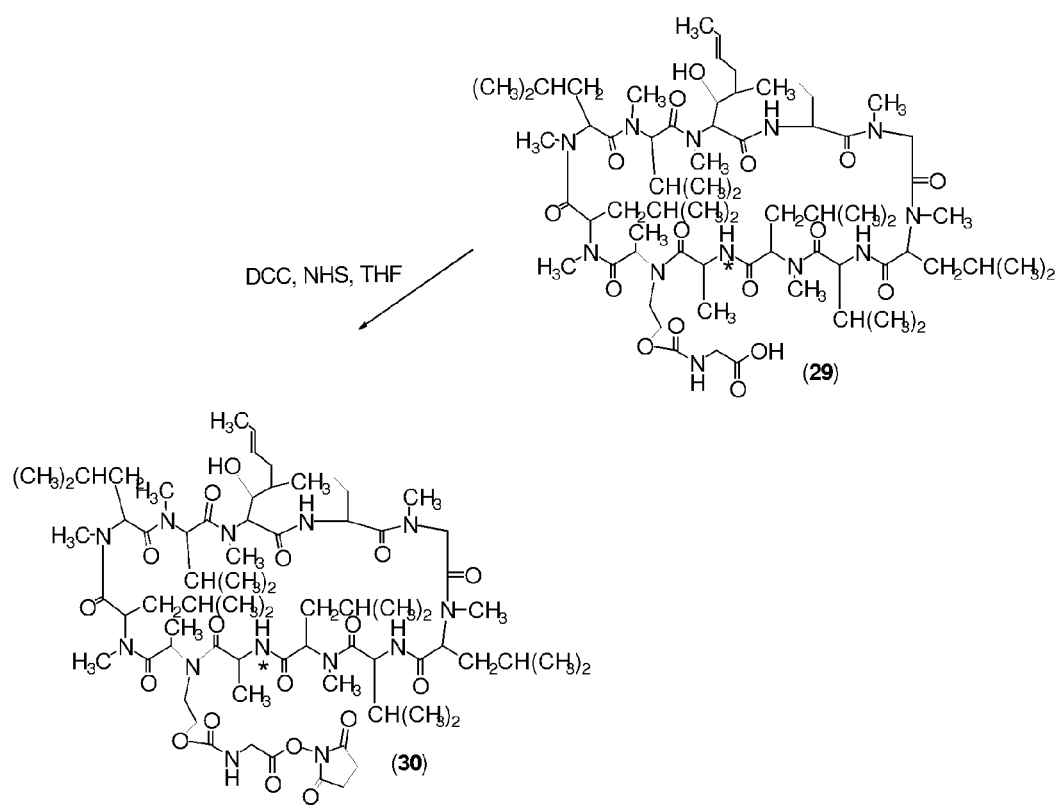
Figure 22:
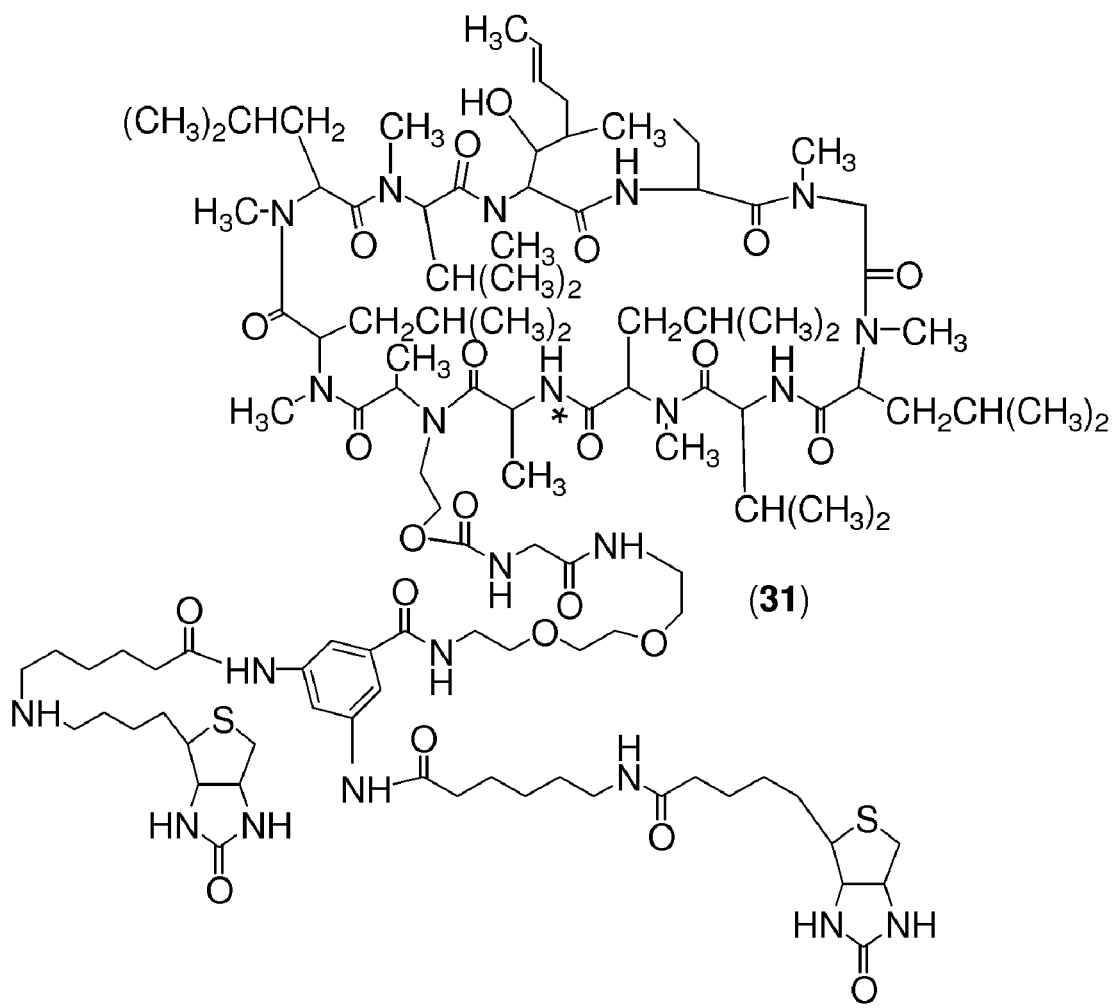
FIG. 22 is a depiction of the preparation of a conjugate of cyclosporin A and bis-biotin.

Preparation of CsA-bis-biotin conjugates. In some embodiments, a CsA-bis-biotin (31) may be prepared by way of illustration and not limitation. The preparation of CsA-bis-biotin (31) may be achieved, for example, using two coupling partners, bis-biotin linker (26) and CsA-derivative (30) (FIGS. 20-22, Schemes 11-13). A synthetic pathway for preparation of 26 is carried out in a total of five-steps. (A preparation of compound (26) is described in U.S. Pat. No. 6,153,442, the relevant disclosure of which is incorporated herein by reference. However, the previous synthesis of 26 required ten reaction steps. The synthetic approach disclosed herein is more efficient and cost-effective than the previous synthesis.) In the present embodiments the synthesis of 26 commences with selective protection of one amine in DA-10 with a suitable protection agent such as, for example, t-butyl anhydride, or the like to give compound (23) (FIG. 20, Scheme 11). The reaction is carried out in an organic solvent such as, for example, methylene chloride, DMF, or the like, at a temperature of about 0° C. to about 5° C., for a period of about 1 to about 24 hours at a pH of about 7.5 to about 13. Acylation of 23 with N-benzyloxycarbonyl-5-aminopentanoic anhydride under basic conditions. The reaction is carried out at a temperature of about 0 to about 80° C., for a period of about 3 to about 16 hours under basic conditions at a pH of about 7.5 to about 11 such as, for example, in the presence of triethyl amine ($Et_3N$), diisopropyl ethyl amine, and the like in an organic solvent such as, for example, methylene chloride, acetonitrile (AcCN), DMF, THF, diethyl ether and the like. Reduction of the nitro groups to amine is carried out using a suitable reducing agent such as, for example, $NaBH_4$, or Cu (I) acetyl acetone or $NaBH_4$, HCl or 10% Pd on carbon, or the like, gives diamine compound (24). Reaction conditions are chosen that are appropriate for the particular reducing agent employed. Reaction of diamine (24) with a commercially available linker, for example, sulfo-NHS-LC-Biotin, $NHS-PEO_4$-biotin or the like gives compound (25). Selective deprotecting of the t-Boc protecting group of 25 under acidic conditions such as, for example, trifluoroacetic acid, a mineral acid, e.g., HCl, etc., or the like in an organic solvent such as, for example, methylene chloride, DMF, or the like gives the desired bis-biotin linker (26) (FIG. 20, Scheme 11).

The synthesis of 30 is depicted in FIG. 21, Scheme 12. Compound 27 is treated to obtain an activated ester using an activation agent such as, for example, ethyl isocyantoacetate, or the like under conditions appropriate for the activation agent. For example, with ethyl isocyantoacetate as the activation agent, the reaction is carried out under tributyltin ethoxide in toluene at a temperature of about 0 to about 40° C., for a period of about 2 to about 16 hours, to give ester (28). Hydrolysis of the ethyl ester and de-protecting of the silicon protecting group on 28 is achieved in a one-step reaction to give acid (29) by treatment under basic conditions such as, for example, sodium carbonate, potassium carbonate, sodium hydroxide, or the like, in an organic solvent such as, for example, an alcohol, e.g., methanol, ethanol, etc., or by treatment under acidic conditions such as, for example, dilute mineral acid as discussed above.

The acid group on 29 is activated by treatment with an activation agent such as, for example, NHS and DCC, carbodiimide, or the like, in an organic solvent such as, for example, an ether, e.g., THF, DMF, or the like, to give NHS ester (30) (FIG. 21, Scheme 12). The above reaction is carried out at a temperature of about 0 to about 40° C., for a period of about 3 to about 16 hours. The coupling reaction of 30 with 26 is carried out under basic conditions such as, for example, triethyl amine, diisopropyl ethyl amine, or the like in an organic solvent such as, for example, an ether, e.g., THF, DMF, dichloromethane, or the like to give final product, CsA-Bis-Biotin (31) (FIG. 22, Scheme 13). The coupling reaction is carried out at a temperature of about 0 to about 40° C., for a period of about 4 to about 16 hours at a pH of about 9 to about 11.

Figure 23:
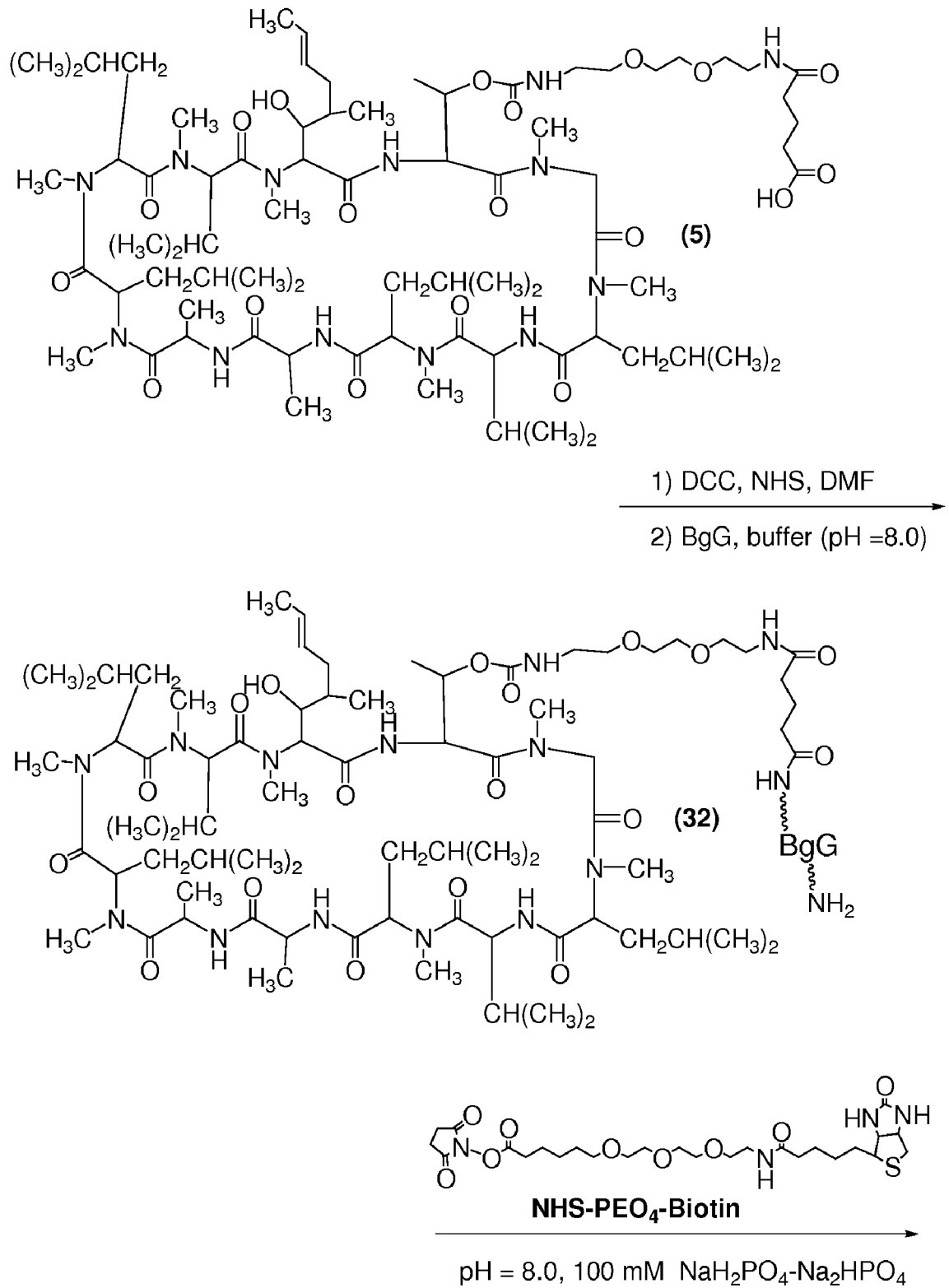
FIG. 23 is a depiction of the preparation of conjugate comprising cyclosporin C linked to biotin.
Figure 23:
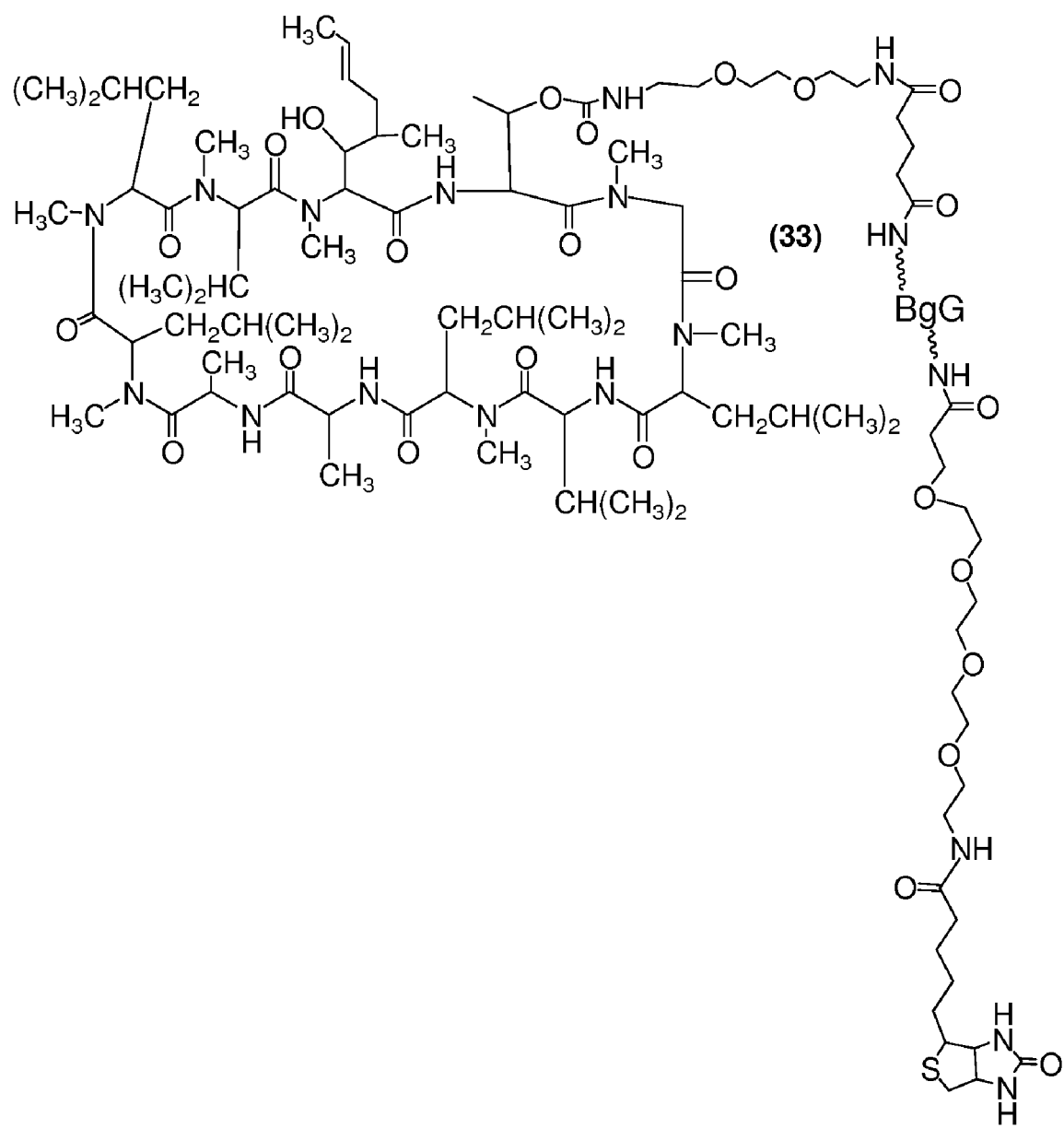

Preparation of CsC-biotin conjugate with protein linker. The synthesis of CsC-DA-10-Hg-BgG-biotin (33) is depicted, by way of illustration and not limitation, in FIG. 23, Scheme 14. An activated ester of 5 is formed with a suitable activation agent, for example, NHS/DCC, as discussed above, in an organic solvent such as, for example, DMF, an ether, e.g., THF, dichloromethane, or the like. The activated NHS ester reacts with free amine groups of BgG to yield CsC-DA-10-Hg-BgG conjugate (32). The reaction is carried out at a temperature of about 0 to about 40° C., for a period of about 6 to about 16 hours at a pH of about 7.5 to about 8.5 or pH of about 8. Reaction of 32 with a linker, $NHS-PEO_4$-Biotin, gives CsC-DA-10-Hg-BgG-PEO4-Biotin (33) FIG. 23, (Scheme 14). The reaction is carried out in an aqueous buffered medium at a temperature of about 0 to about 40° C., for a period of about 6 to about 24 hours at a pH of about 7.5 to about 8.5 or pH of about 8. Buffers that may be employed include sodium hydrogen phosphate, sodium dihydrogen phosphate, or combinations thereof.

Kits Comprising Reagents for Conducting Assays for CsA

The reagents for conducting a particular assay may be present in a kit useful for conveniently performing an assay for the determination of a CsA analyte. In some embodiments a kit comprises in packaged combination a conjugate of an antibody for CsA and biotin, streptavidin-sensitizer particles and CsC-chemiluminescent particles as well as any other reagents for performing the assay, the nature of which depend upon the particular assay format. In some embodiments a kit comprises, as separate reagents, antibody for CsA bound to chemiluminescent particles, streptavidin-sensitizer particles and a conjugate of CsA and biotin as well as any other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional sbp members, ancillary reagents, and so forth.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

Other Embodiments

An embodiment is a composition comprising cyclosporin C or cyclosporin A associated with a particle wherein the particle is associated with a chemiluminescent composition. In a specific embodiment of the above composition, the particle is a polystyrene particle and the cyclosporin A is linked to the polystyrene particle by means of a linking group that has the formula:

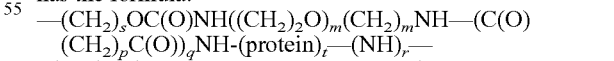

wherein s is 1 to 3, or 2 to 3, or 1 to 2, n is 1 to 4, or 1 to 3, or 1 to 2, or 2 to 4, or 2 to 3, or 3 to 4 and m is 1 to 3, or 1 to 2 or 2 to 3 and p is 1 to 4, or 1 to 3, or 1 to 2, or 2 to 4, or 2 to 3, or 3 to 4 and q is 0 or 1 and t is 0 or 1 and r is 0 or 1, or wherein cyclosporin C is linked to the polystyrene particle by means of a linking group that has the formula:

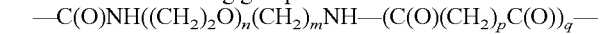

wherein n is 1 to 4, or 1 to 3, or 1 to 2, or 2 to 4, or 2 to 3, or 3 to 4 and m is 1 to 3, or 1 to 2 or 2 to 3 and p is 1 to 4, or 1 to 3, or 1 to 2, or 2 to 4, or 2 to 3, or 3 to 4 and q is 0 or 1.

An embodiment is a composition comprising cyclosporin A or cyclosporin C conjugated to bis-biotin. In a specific embodiment of the above composition, cyclosporin A is conjugated to bis-biotin, at an amide nitrogen at position 7 or position 8 employing the carboxylic acid functionality of the biotin, by means of a linking group that has the formula:

—(CH$_2$)$_e$OC(O)NH(CH$_2$)$_f$C(O)NH((CH$_2$)$_2$O)$_g$(CH$_2$)$_h$NHC(O)D wherein D is

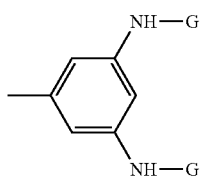

wherein G is —C(O)(CH$_2$)$_j$NH—, and wherein e is 1 to 3, or 2 to 3, or 1 to 2, f is 1 to 3, or 1 to 2, or 2 to 3, g is 1 to 4, or 1 to 3, or 1 to 2, or 2 to 4, or 2 to 3, or 3 to 4, h is 1 to 3, or 1 to 2 or 2 to 3 and j is 1 to 6, or 2 to 6, or 3 to 6, or 4 to 6, or 5 to 6, or 1 to 5, or 2 to 5, or 3 to 5, or 4 to 5, or 1 to 4, or 2 to 4, or 3 to 4, or 1 to 3, or 2 to 3, or 1 to 2.

The following examples further describe the specific embodiments of the invention by way of illustration and not limitation and are intended to describe and not to limit the scope of the invention. Parts and percentages disclosed herein are by volume unless otherwise indicated.

EXAMPLES

General Comments

General Method Analytical thin layer chromatography (TLC) was the usual analysis method and performed on Analtech Uniplate Silica Gel GF (0.25 mm) (Analtech, Inc., Newark Del.) glass-backed plates using the specified solvent. The spots on TLC were visualized by ultraviolet light (short and/or long wave) and/or iodine vapors. Flash chromatography was carried out on Whatman silica gel 60 Å (230-400 mesh) (Whatman Inc., Florham Park, N.J.). Preparative thin layer chromatography (PTLC) separations were carried out on pre-coated silica gel plates from Analtech, Newark Del. (Catalog No: 02015, silica gel, 2000 μm). Unless otherwise specified, reagents were obtained from Sigma Chemical Company (St. Louis Mo.), Aldrich Chemical Company (Milwaukee Wis.), or Fluka Chemical Corporation (Milwaukee Wis.) and used as received. The streptavidin-sensitizer bead was prepared in a method analogous to that described in U.S. Pat. Nos. 6,153,442, 7,022,529, 7,229,842 and U.S. Patent Application Publication No. 20050118727A. Assays were conducted using the DIMENSION® RxL analyzer available from Dade Behring Inc., Newark Del. The instrument was employed using induced luminescence immunoassay technology and was equipped with an appropriate reader.

Preparation of Compounds

Preparation of CsC-DA-10 (3): See FIG. 10 and U.S. Pat. No. 5,990,274. To a solution of CsC (2) (500 mg, 0.4103 mmol) in AcCN (9.0 mL) were added disuccinimidyl carbonate (DSC) (421 mg, 1.64 mmol) and Et$_3$N (0.917 ml). The reaction mixture was stirred at room temperature for 4 hours. TLC analysis of the mixture showed the completion of the reaction. (DA-10) (2430 mg, 16.4 mmol) and Et$_3$N (0.917 ml) were added to the mixture. The reaction was stirred at room temperature for 24 hours. Most of AcCN and Et$_3$N were removed by rotary evaporation. Dichloromethane (80 mL) was added and the organic phase was washed with deionized water (DE water) (4×50 ml) until neutral (pH=7.0). The organic phase was dried over MgSO$_4$, filtered and concentrated to dryness. The residue was put in high vacuum to give compound (3) (500 mg).

Preparation of CsC-DA-10-EPRM Chemibead (4): See FIG. 11. To an EPRM chemibead suspension (2 ml, 117.1 mg/ml) was added 0.2 ml of DMSO solution of CsC-DA-10 (3) (34.4 mg) in a greenroom avoiding daylight. An MES buffer (50 mM, 1 ml, pH=6.0) was used to rinse the bottle of DMSO solution and the rinse was added to the mixture. To the suspension was added 0.103 ml of NaCNBH$_3$ (25 mg/ml) solution. The suspension was rocked at ADAMS™ Nutator at 37° C. for 40 hours. 1M CMO (0.25 mL) was added to the mixture, which was rocked at 37° C. for 2.5 hours. The mixture was centrifuged at 15,000 rpm for 25 minutes and the resulting pellet was re-suspended by sonication with 30 ml of phosphate buffer (50 mM, pH=8.0). The wash process was repeated (30×40 ml) with the same buffer and (3×40 ml) with the suspension buffer (10 mM HEPES, 150 mM NaCl, 1 mM EDTA, 1 mg/ml BSA, 0.1% TX-405®, 0.15% Proclin 300, 0.1 mg/ml neomycin sulfate, pH=8.0). The CsC-DA-10-EPRM chemibead (4) was re-suspended in 4 ml of the same suspension buffer and the solid % was determined to be 26.6 mg/ml.

Preparation of Compound (5) and CsC-DA-10-Hg-APRM (6): See FIG. 12. To a solution of CsC-DA-10 (3) (100 mg, 0.0718 mmol) in CH$_2$Cl$_2$ (5 ml) was added glutaric anhydride (18 mg, 0.157 mmol) and trimethylamine (110 μL, mmol). The reaction was stirred at room temperature for 2 hours. Water (10 mL) was added and the aqueous phase was adjusted to pH 3 by adding 0.1 N HCl. The aqueous phase was extracted with CH$_2$Cl$_2$ (3×20 ml). The combined organic phases were washed with water (3×20 mL) and dried over Na$_2$SO$_4$. The organic phase was filtered and concentrated to dryness. The residue was subjected to high vacuum to give compound (5) (95 mg). To a solution of compound (5) (95 mg, 0.063 mmol) in THF (5 mL) were added EDAC (36 mg, 0.18 mmol) and NHS (22 mg, 0.191 mmol). The reaction mixture was stirred at room temperature for 6 hours. TLC analysis of the mixture showed the completion of the reaction. Most of the THF was removed by rotary evaporation. The residue was subjected to high vacuum for 1 hour and dissolved in DMSO (0.5 ml) for the next reaction. To an APRM chemibead suspension (6.5 ml, 30.6 mg/ml) in phosphate buffer (100 mM, pH=8.0) was added 0.5 ml of the above DMSO solution of the activated NHS ester of compound (5) in a greenroom avoiding daylight. A phosphate buffer (100 mM, 2 ml, pH=8.0) was used to rinse the bottle of DMSO solution and the rinse was added to the reaction mixture. The reaction mixture was rocked in an ADAMS Nutator (Model No. 421105, Becton, Dickinson and Company, Sparks, Md.) at room temperature for 24 hours. The mixture was centrifuged at 15,000 rpm for 25 minutes and the resulting pellet was re-suspended by sonication with 30 ml of the same phosphate buffer (30 ml). The wash process was repeated (30×40 ml) with the same buffer and (3×30 ml) with the suspension buffer (10 mM HEPES, 150 mM NaCl, 1 mM EDTA, 1 mg/ml BSA, 0.1% TX-405, 0.15% Proclin 300, 0.1 mg/ml neomycin sulfate, pH=8.0). The CsC-DA-10-Hg-APRM chemibead (6) was re-suspended in 8 ml of the same suspension buffer and the solid % was determined to be 22.6 mg/ml.

Preparation of CsA-DA-10 (8) and CsA-DA-10-EPRM Chemibead (9): See FIG. 13.

To a solution of CsA-OSiMe$_3$ (7) (150 mg, 0.10 mmol) in MeOH (5 mL) were added K$_2$CO$_3$ (138 mg, 1.0 mmol). The reaction mixture was stirred at room temperature for 16 hours. Most of the MeOH was removed by rotary evaporation and water (10 ml) was added. The aqueous phase was extracted with $CH_2Cl_2$ (3×30 ml). The combined organic phases were washed with water (2×20 mL) and dried over $Na_2SO_4$ The organic phase was filtered and concentrated to dryness. The residue was put in high vacuum to give compound (8) (131 mg). To EPRM chemibead suspension (2 ml, 117.1 mg/ml) was added 0.2 ml of DMSO solution of CsA-DA-10 (8) (32 mg) in a greenroom avoiding daylight. An MES buffer (50 mM, 1 ml, pH=6.0) was used to rinse the bottle of DMSO solution and the rinse was added to the mixture. To this suspension was added 0.10 ml of $NaCNBH_3$ (25 mg/ml) solution. The reaction mixture was rocked in an ADAMS Nutator at 37° C. for 40 hours. 1M CMO (0.25 mL) was added to the mixture, which was rocked at 37° C. for 2.5 hours. The mixture was centrifuged at 15,000 rpm for 25 minutes and the pellet was re-suspended by sonication with 30 ml of phosphate buffer (50 mM, pH=8.0). The wash process was repeated (30×40 ml) with the same buffer and (3×20 ml) with the suspension buffer (10 mM HEPES, 150 mM NaCl, 1 mM EDTA, 1 mg/ml BSA, 0.1% TX-405, 0.15% Proclin 300, 0.1 mg/ml neomycin sulfate, pH=8.0). The CsA-DA-10-EPRM chemibead (9) was re-suspended in 4 ml of the same suspension buffer and the solid % was determined to be 18 mg/ml.

Preparation of CsA-DA-10-Hg-APRM (11): See FIG. 14. To a solution of compound (10) (112 mg, 0.073 mmol) in THF (5 mL) were added EDAC (47.5 mg, 0.18 mmol) and NHS (39 mg, 0.191 mmol). The reaction mixture was stirred at room temperature for 6 hours. TLC analysis of the mixture showed the completion of the reaction. Most of the THF was removed by rotary evaporation. The residue was put in high vacuum for 1 hour and dissolved in DMSO (0.5 ml) for the next reaction. To APRM chemibead suspension (6.5 ml, 30.6 mg/ml) in phosphate buffer (100 mM, pH=8.0) was added 0.5 ml of DMSO hapten solution in a greenroom avoiding daylight. A phosphate buffer (100 mM, 2 ml, pH=8.0) was used to rinse the bottle of DMSO solution and the rinse was added to the reaction mixture. The reaction mixture was rocked in an ADAMS Nutator at room temperature for 24 hours. The mixture was centrifuged at 15,000 rpm for 25 minutes and the pellet was re-suspended by sonication with 30 ml of same phosphate buffer (30 ml). The wash process was repeated (30×40 ml) with the same buffer and (3×30 ml) with the suspension buffer (10 mM HEPES, 150 mM NaCl, 1 mM EDTA, 1 mg/ml BSA, 0.1% TX-405, 0.15% Proclin 300, 0.1 mg/ml neomycin sulfate, pH=8.0). The CsA-DA-10-Hg-APRM chemibead (11) was re-suspended in 8 ml of the same suspension buffer and the solid % was determined to be 20 mg/ml.

Preparation of CsA-BgG-EPRM (13): See FIG. 15. To an EPRM chemibead suspension (1 ml, 100 mg/ml) was added 1 ml of CsA-BgG (12) (CsA-DA-10-Hg-BgG) solution (20 mg/ml) in MES buffer (50 mM, 1 ml, pH=6.0) in a greenroom avoiding daylight. To this suspension was added 0.045 ml of $NaCNBH_3$ (25 mg/ml) solution. The reaction mixture was rocked in an ADAMS Nutator at 37° C. for 63 hours. 1M CMO (0.13 mL) was added to the mixture, which was rocked at 37° C. for 2.5 hours. The mixture was centrifuged at 15,000 rpm for 25 minutes and the pellet was re-suspended by sonication with 30 ml of phosphate buffer (50 mM, pH=8.0). The wash process was repeated (13×40 ml) with the same buffer and (3×20 ml) with the suspension buffer (50 mM HEPES, 300 mM NaCl, 1 mM EDTA, 1 mg/ml BSA, 0.1% TX-405, 0.15% Proclin 300, 0.1 mg/ml neomycin sulfate, pH=8.0). The CsA-DA-10-EPRM chemibead (9) was re-suspended in 2.5 ml of the same suspension buffer and the solid % was determined to be 33.3 mg/ml.

Preparation of anti-CsA-Antibody-LC-Biotin (16) and anti-CsA-Antibody-PEO4-Biotin (18): See FIG. 16. To anti-CsA antibody (2G4, IgG1) (14) (2.33 ml, 3 mg/ml) in buffer solution (10 mM $NaH_2PO_4$—$Na_2HPO_4$-300 mM NaCl, pH=7.0) was added 0.078 ml of Sulfo-NHS-LC-Biotin (15) (10 mg/ml) in the same buffer solution. The molar ratio of antibody to Sulfo-NHS-LC-Biotin is 1 to 30. The reaction mixture was rocked in an ADAMS Nutator at ambient temperature for 3 hours. Glycine solution (2M) was adjusted to pH=8.0 by addition of 1M HCl. The adjusted glycine solution (0.035 ml) was added to the reaction mixture, which was rocked in an ADAMS Nutator at ambient temperature for 1 hour. The anti-CsA-Antibody-LC-Biotin (16) was purified by an AMICON® concentrator equipped with a membrane (MW cut off 30000) and the filtrate was monitored to ensure removal of biotin linker. The concentration of anti-CsA-Antibody-LC-Biotin (16) was measured at UV 280 nm using coefficient factor 1.41. This gave the biotin compound (16) (5 ml, 1.5 mg/ml).

To anti-CsA antibody (2G4, IgG1) (14) (2.33 ml, 3 mg/ml) in buffer solution (10 mM $NaH_2PO_4$—$Na_2HPO_4$-300 mM NaCl, pH=7.0) was added 0.087 ml of NHS-$PEO_4$-Biotin (17) (10 mg/ml) in the same buffer solution. The molar ratio of antibody to NHS-$PEO_4$-Biotin was 1 to 30. The reaction mixture was rocked in an ADAMS Nutator at ambient temperature for 3 hours. Glycine solution (2M) was adjusted to pH=8.0 by addition of 1M HCl. The adjusted glycine solution (0.035 ml) was added to the reaction mixture, which was rocked in an ADAMS Nutator at ambient temperature for 1 hour. The anti-CsA-Antibody-LC-Biotin (16) was purified in an AMICON concentrator equipped with a membrane (MW cut off 30000) and the filtrate was monitored to ensure removal of the biotin linker. The concentration of anti-CsA-Antibody-$PEO_4$-Biotin (18) was measured at UV 280 nm using coefficient factor 1.41. This gave the biotin (18) (6 ml, 1.16 mg/ml). This biotinylation procedure was used with different molar ratios and/or different kinds of biotin linkers.

Preparation of EPRM-anti-CsA-Ab-Chemibead (19): See FIG. 17. To EPRM chemibead suspension (2 ml, 100 mg/ml) was added 2 ml of anti-CsA-Antibody (2G4, IgG1) solution (20 mg/ml) in MES buffer (50 mM, 1 ml, pH=6.0) in a greenroom avoiding daylight. To this suspension was added 0.09 ml of $NaCNBH_3$ (25 mg/ml) solution. The reaction mixture was rocked in an ADAMS Nutator at 37° C. for 63 hours. 1M CMO solution (0.25 mL) was added to the mixture, which was rocked at 37° C. for 2.5 hours. The mixture was centrifuged at 15,000 rpm for 25 minutes and the pellet was re-suspended by sonication with 30 ml of phosphate buffer (50 mM, pH=8.0). The wash process was repeated (13×30 ml) with the same buffer and (5×30 ml) with the suspension buffer (50 mM HEPES, 300 mM NaCl, 1 mM EDTA, 1 mg/ml BSA, 0.1% TX-405, 0.15% Proclin 300, 0.1 mg/ml neomycin sulfate, pH=8.0). The EPRM-anti-CsA-Ab-chemibead (19) was re-suspended in 5 ml of the same suspension buffer and the solid % was determined to be 28.3 mg/ml.

Preparation of CsA-DA-10-Hg-BgG-Biotin (20): See FIG. 18. To CsA-DA-10-Hg-BgG (12) (5 ml, 5 mg/ml) in buffer solution (100 mM $NaH_2PO_4$—$Na_2HPO_4$, pH=8.0) was added 0.4 ml of NHS-$PEO_4$-Biotin (17) (12.5 mg/ml) buffer solution (100 mM $NaH_2PO_4$—$Na_2HPO_4$, pH 7.0). The molar ratio of CsA-DA-10-Hg-BgG (12) to NHS-$PEO_4$-Biotin was 1 to 50. The reaction mixture was rocked in an ADAMS Nutator at 4° C. (cold room) for 16 hours. The CsA-DA-10-Hg-BgG-Biotin (20) was purified using an AMICON concentrator equipped with a membrane (MW cut off 30000) with buffer solution 100 mM $NaH_2PO_4$—$Na_2HPO_4$, pH 7.0). The filtrate was monitored by UV to ensure removal of biotin linker. The concentration of CsA-DA-10-Hg-BgG-Biotin (20) was measured at UV 280 nm using coefficient factor 1.41. This gave the biotin (20) (25 ml, 0.97 mg/ml). This biotinylation procedure was used with different molar ratios and/or different kind of biotin linkers.

Preparation of CsA-DA-10-PEO4-Biotin (21): See FIG. 19. To a solution of CsA-DA-10 (8) (40 mg, 0.028 mmol) in THF (5 mL) was added a solution of NHS-PEO$_4$-Biotin (17) (40 mg, 0.068 mmol) and diisopropylethylamine (0.05 ml, 0.287 mmol). The reaction mixture was stirred at room temperature for 2 hours. Most of the THF was evaporated by rotary evaporation and water (30 ml) was added. The aqueous phase was extracted with CH$_2$Cl$_2$ (3×30 ml). The combined organic phases were washed with water (30 ml), dried over Na$_2$SO$_4$, filtered and evaporated to dryness. The residue was dissolved in CH$_2$Cl$_2$ (0.5 ml) and the solution was applied to a preparative THC plate (Analtech, Catalog No: 02015, silica gel, 2000 μm). The TLC was developed in mixed solvent (MeOH/CH$_2$Cl$_2$=1/9) and the major band was collected and extracted with (MeOH/CH$_2$Cl$_2$=1/9) (30 ml). The solvent was evaporated to dryness and the residue was put in high vacuum to give the desired product (21) (15.5 mg).

Preparation of compound (23): Compound (23) was prepared by methods similar to those previously described in U.S. Pat. No. 6,153,442.

Preparation of compound (24): Compound (24) was prepared as follows: See FIG. 20. To a solution of 23 (10 g, 40.7 mmol) in THF (100 ml) was added dropwise Et$_3$N (4.6 g) and 3,5-dinitrobenzoyl chloride (9.2 g, 39.9 mmol) in THF (100 ml). The reaction mixture was stirred at room temperature for 2 hours. Most of the THF was removed by rotary evaporation under reduced pressure. The residue was dissolved in CH$_2$Cl$_2$ (200 ml) and water (120 ml) was added. The mixture was poured into a separation funnel and extracted with 0.2N HCl (2×100 ml), 0.1 N sodium carbonate (2×50 ml) and water (1×100 ml). The organic phase was dried over sodium sulfate, filtered and evaporated to dryness. The residue was subjected to high vacuum to give the intermediate (15.5 g) as a viscous oil. This intermediate (486 mg, 1.1 mmol) was dissolved in ethanol (EtOH) (30 ml) containing 10% Pd on carbon (400 mg). The mixture was bubbled with nitrogen for 20 minutes to remove oxygen in the solution. To this solution was added sodium borohydride (400 mg) under nitrogen and the mixture was stirred at room temperature for 5 minutes. HCl (1N, 1 ml) was added dropwise into the mixture (Caution: hydrogen was formed from the reaction) under nitrogen in the period of time (10 minutes). The mixture was stirred for 30 minutes. An additional 1 ml of HCl (1N) was added to the mixture, which was stirred for an additional 30 minutes followed by one more addition of 1 ml of HCl (1 N). The mixture was stirred for 120 minutes and bubbled with nitrogen for 10 minutes. The ethanol was filtered with celite and the celite was washed with ethanol (2×10 ml). The combined ethanol was concentrated to dryness and the residue was purified by flash column chromatography (silica gel) using MeOH/CH$_2$Cl$_2$ (1/9) to give the desired product (24) (264 mg).

Preparation of Compound (25): See FIG. 20. To a solution of 24 (88 mg, 0.23 mmol) in THF (10 ml) was added Et$_3$N (0.3 mL) and sulfo-NHS-LC-biotin (260 mg, 0.467 mmol). The reaction mixture was stirred at room temperature for 5 hours. Additional sulfo-NHS-LC-biotin (125 mg, 0.224 mmol) and Et$_3$N (0.15 ml) was added to the mixture. The mixture was stirred for additional 5 hours. Most of the THF was removed by rotary evaporation under reduced pressure. The residue was dissolved in MeOH/CH$_2$Cl$_2$ (1/9) (0.3 ml) and the solution was applied to a preparative THC plate (Analtech, Catalog No: 02015, silica gel, 2000 μm). The TLC was developed in mixed solvent (MeOH/CH$_2$Cl$_2$=2/8) and the major band was collected and extracted with (MeOH/CH$_2$Cl$_2$=3/7) (50 ml). The solvent was evaporated to dryness and the residue was put in high vacuum to give the desired product (25) (39 mg).

Preparation of Compound (26): See FIG. 20. To a solution of compound (25) (39 mg, 0.0367 mmol) in CH$_2$Cl$_2$ (2 ml) was added trifluoroacetic acid (TFA) (1.5 mL). The reaction mixture was stirred at room temperature for 20 minutes. TLC analysis of the reaction showed that starting material (25) disappeared and a new more polar spot was displayed (silica gel, ethyl acetate). Most of the CH$_2$Cl$_2$ and TFA were removed by rotary evaporation under reduced pressure. The residue was put in 20 ml of hexane and 15 ml of CH$_2$Cl$_2$. The solvent was evaporated to dryness again to remove a trace of TFA and the residue was put under high vacuum for 2 hours. This gave the desired product (26) used for next reaction without further purification.

Preparation of CsA Intermediate (28): See FIG. 21. To a solution of compound (27) (240 mg, 0.1819 mmol) (prepared according to a procedure similar to that described in U.S. Pat. No. 6,190,873, example 5, the relevant disclosure of which is incorporated herein by reference) in toluene (3 mL) was added tributyltin ethoxide (112 mg, 0.112 ml, 0.0969 mmol) under nitrogen. The reaction was stirred at room temperature for 5 minutes. To this solution was added ethyl isocyanatoacetate (73 μL, 84 mg, 0.652 mmol). The reaction was stirred at room temperature for 2 hours. TLC analysis of the reaction showed that starting material (27) disappeared and a new less polar spot was displayed (silica gel, MeOH/ethyl acetate=3/97). Water (10 ml) was added and the aqueous phase was extracted with ethyl acetate (2×30 ml). The combined organic phase was washed with water (30 ml), brine (30 ml), dried over Na$_2$SO$_4$, filtered and evaporated to dryness. The residue was purified by flash column chromatography (silica gel) using MeOH/ethyl acetate (3/97) to give the desired product (28) (224 mg).

Preparation of CsA Intermediate (29): See FIG. 21. To a solution of compound (28) (112 mg, 0.0774 mmol) in MeOH (6.0 ml) and H$_2$O (0.5 ml) was added K$_2$CO$_3$ (140 mg, 1.01 mmol). The reaction mixture was stirred at room temperature for 16 hours. Water (10 ml) was added and HCl (1N) was added to the mixture to adjust the pH to 1. The reaction mixture was stirred for 10 minutes. The aqueous phase was extracted with CH$_2$Cl$_2$ (3×30 ml). The combined organic phase was washed with brine/water (1/1) (50 ml). The organic phase was dried over Na$_2$SO$_4$, filtered and evaporated to dryness. The residue was put in high vacuum for 16 hours. The residue was dissolved at CH$_2$Cl$_2$/MeOH (2/8) (0.5 ml) and the solution was applied to a preparative THC plate (Analtech, Catalog No: 02015, silica gel, 2000 μm). The TLC was developed in mixed solvent (MeOH/CH$_2$Cl$_2$=1/9) and the major band was collected and extracted with (MeOH/CH$_2$Cl$_2$=3/7) (50 ml). The solvent was evaporated to dryness and the residue was put in high vacuum under P$_2$O$_5$ for 16 hours to give the desired product (29) (55.6 mg).

Preparation of CsA-Bis-Biotin (31): See FIGS. 21-22. To a solution of compound (29) (55.6 mg, 0.04125 mmol) in THF (5 mL) was added DCC (20 mg, 0.0969 mmol) and NHS ester (15 mg, 0.13 mmol). The reaction mixture was stirred at room temperature under argon for 6 hours. TLC analysis of the mixture showed that a less polar spot displayed in comparison with compound (29) (MeOH/CH$_2$Cl$_2$=1/9). The precipitate from the reaction was filtered off and washed with anhydrous THF (3 ml). The combined organic phase was evaporated to dryness to give activated hapten (30), which was dissolved in DMF (1 ml) for the next reaction.

Compound (26) (FIG. 20) was dissolved in DMF (5 ml) and Et3N (0.1 ml). To this solution was added the activated hapten (30) in DMF solution (1 mL). The reaction was stirred at room temperature for 4 hours. Most of the DMF was removed by rotary evaporation under reduced pressure. The residue was subjected to high vacuum for 2 hours to give crude product (31). The crude product was dissolved in 0.3 ml of MeOH/CH$_2$Cl$_2$ (1/9) and the solution was applied to two preparative THC plates (Analtech, Catalog No: 02015, silica gel, 2000 μm). The TLC was developed using a mixed solvent (MeOH/CH$_2$Cl$_2$=1/9) and the major band was collected from two TLC plates and extracted with (MeOH/CH$_2$Cl$_2$=2/8) (50 ml). The solvent was evaporated to dryness and the residue was put in high vacuum to give the desired product (31) (54 mg).

Preparation of CsC-DA-10-Hg-BgG (32): See FIG. 23. To a solution of compound (5) (58 mg, 0.0385 mmol) in THF (6 mL) was added DCC (15 mg, 0.0727 mmol) and NHS ester (9 mg, 0.078 mmol). The reaction was stirred at room temperature for 6 hours. The complete reaction was observed by checking TLC (silica gel, MeOH/CH$_2$Cl$_2$=1/9). The precipitate from the reaction was filtered off and washed with anhydrous THF (3 ml). The combined organic phase was evaporated to dryness and the activated hapten was dissolved in DMF (1.2 ml) for next reaction.

To a solution of Bovine BgG (200 mg) in NaH$_2$PO$_4$—Na$_2$HPO$_4$ buffer (pH=8.0, 0.1M, 50 ml) and MeOH (5 ml) was added the activated hapten in DMF solution (1.2 ml). The reaction mixture was stirred at room temperature for 16 hours. The mixture was centrifuged at 8.000 rpm for 20 minutes and the supernatant was collected and filtered through 0.45 um cartridge. The filtered supernatant was concentrated to 20 ml using an AMICON concentrator with a membrane (MW cut off 10000). The solution (20 ml) was applied to a SEPHADEX G-25® column, eluting with NaH$_2$PO$_4$—Na$_2$HPO$_4$ buffer (pH 7.00, 0.1M). The eluted fractions from the column were monitored by UV at 280 nm. A clean separation between the CsC-DA-10-Hg-BgG (32) and the hapten was obtained. Fractions containing the product were pooled together and concentrated to 21 ml by an AMICON concentrator. The concentration of compound (32) was measure at UV 280 nm to be 3 mg/ml. This gave the desired CsC-DA-10-Hg-BgG (32) (21 ml, 3 mg/ml).

Preparation of CsC-DA-10-Hg-BgG-Biotin (33): See FIG. 23. To CsC-DA-10-Hg-BgG (32) (6 ml, 3 mg/ml) in buffer solution (100 mM NaH$_2$PO$_4$—Na$_2$HPO$_4$, pH 7.0) was added 0.212 ml of NHS-PEO$_4$-Biotin (17) (10 mg/ml) in the same buffer solution. The molar ratio of CsC-DA-10-Hg-BgG (32) to NHS-PEO$_4$-Biotin is 1 to 30. The reaction mixture was rocked in an ADAMS Nutator at room temperature for 3 hours. The CsC-DA-10-Hg-BgG-Biotin (33) was purified with buffer solution (100 mM NaH$_2$PO$_4$—Na$_2$HPO$_4$, pH 7.0) by using an AMICON concentrator equipped with a membrane (MW cut off 10000). The filtrate was monitored by UV to ensure removal of biotin linker. The concentration of CsC-DA-10-Hg-BgG-Biotin (33) was measured at UV 280 nm using coefficient factor 1.41. This gave CsC-DA-10-Hg-BgG-Biotin (33) (7.1 ml, 1.3 mg/ml). This biotinylation procedure was used with different molar ratios and/or different kind of biotin linkers.

The following assay formats were conducted using reagents as described above.

Format 1: In this embodiment of an assay method for the determination of CsA, a combination is provided in a medium wherein the combination comprises (i) the sample, (ii) a photosensitizer associated with a first particle and being capable of generating singlet oxygen wherein the first particle comprises a biotin binding partner, (iii) a chemiluminescent composition activatable by the singlet oxygen and associated with a second particle wherein the second particle comprises CsC or CsA and (iv) a conjugate of an antibody for CsA and biotin. The combination is subjected to conditions for binding of CsA, if present, to the antibody for CsA. The photosensitizer is irradiated with light and the amount of luminescence generated by the chemiluminescent composition is detected, the amount of luminescence being related to the presence and/or amount of CsA in the sample.

For assays in accordance with Format 1 the following reagents discussed above were employed: streptavidin-photosensitizer beads (streptavidin sensibeads), CsA- or CsC-chemibeads and anti-CsA Mab-PEO$_4$-biotin (18) (Mab is monoclonal antibody). The samples were calibrators that contained 0, 80.00, 180.00, 330.00 and 500.00 ng/mL of CsA, calibrators 1-5, respectively. The appropriate reagents and samples were added to a reaction vessel of the DIMENSION RxL analyzer as follows: Into the reaction vessel, 20 μL of anti-CSA (2G4) Mab-biotin was added followed by 20 μL of streptavidin sensibeads followed by 15 μL of water. Then, 10 μL of sample was added followed by 15 μL of water. The combination was incubated for 219 seconds and 20 μL CsA- or CsC-chemibeads was added followed by 150 μL of water. The combination was incubated for either 366 seconds or 713 seconds at a temperature of 37° C. Then, the combination was irradiated with light at 680 nM for a period of 0.2 to 1 second and the signal (in photon counts referred to as LOCI signal in the tables below) was read using a reader (PerkinElmer CPM Detector, PerkinElmer Life And Analytical Sciences, Inc., Waltham Mass.). The results are summarized below in Tables 1-4 and in FIGS. 24-27.

Figure 24:
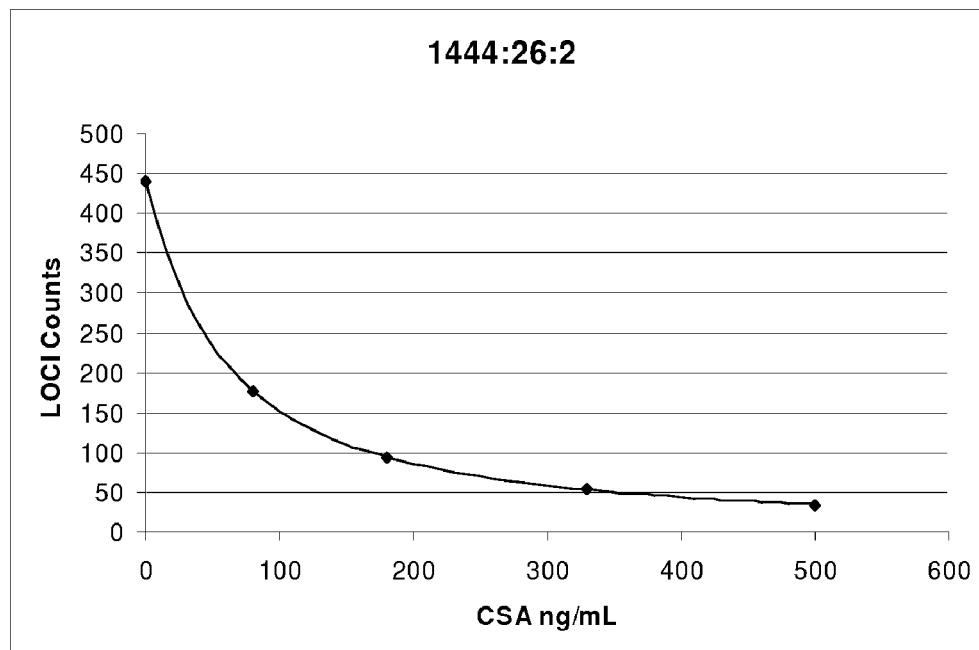
FIG. 24 is graphic depiction of the results of an assay for CsA conducted according to Format 1 of the present embodiments using the following reagents: CsC-DA-10-EPRM chemiluminescent particles (EPRM chemibead), antibody for CsA-biotin, and streptavidin-sensitizer particles.

Table 1 and FIG. 24 summarize the results wherein CsC-DA-10-EPRM chemibead (4) was employed.

TABLE 1

| CsC-DA-10-EPRM chemibead (4) | |
|---|---|
| Calibrator | LOCI Signal |
| 0.00 | 440 |
| 80.00 | 177 |
| 180.00 | 94 |
| 330.00 | 53 |
| 500.00 | 34 |

Figure 25:
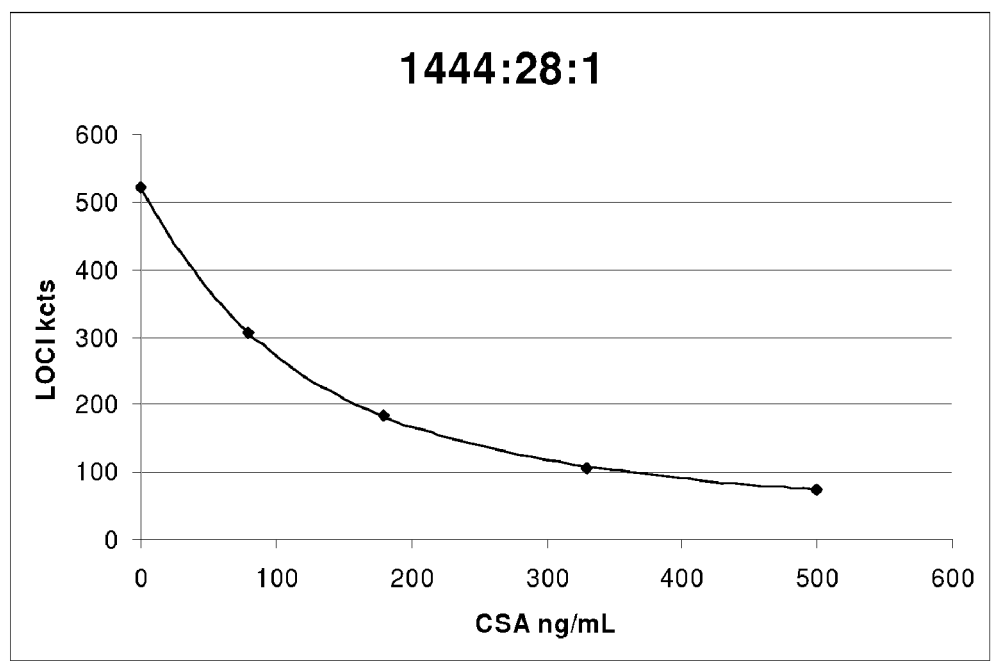
FIG. 25 is graphic depiction of the results of another assay for CsA conducted according to Format 1 of the present embodiments using the following reagents: CsC-DA-10-Hg-APRM chemiluminescent particles, antibody for CsA-biotin, and streptavidin-sensitizer particles.

Table 2 and FIG. 25 summarize the results wherein CsC-DA-10-Hg-APRM chemibead (6) was employed.

TABLE 2

| CsC-DA-10-Hg-APRM chemibead (6) | |
|---|---|
| Calibrator | LOCI Signal |
| 0.00 | 522 |
| 80.00 | 306 |
| 180.00 | 185 |
| 330.00 | 105 |
| 500.00 | 74 |

Figure 26:
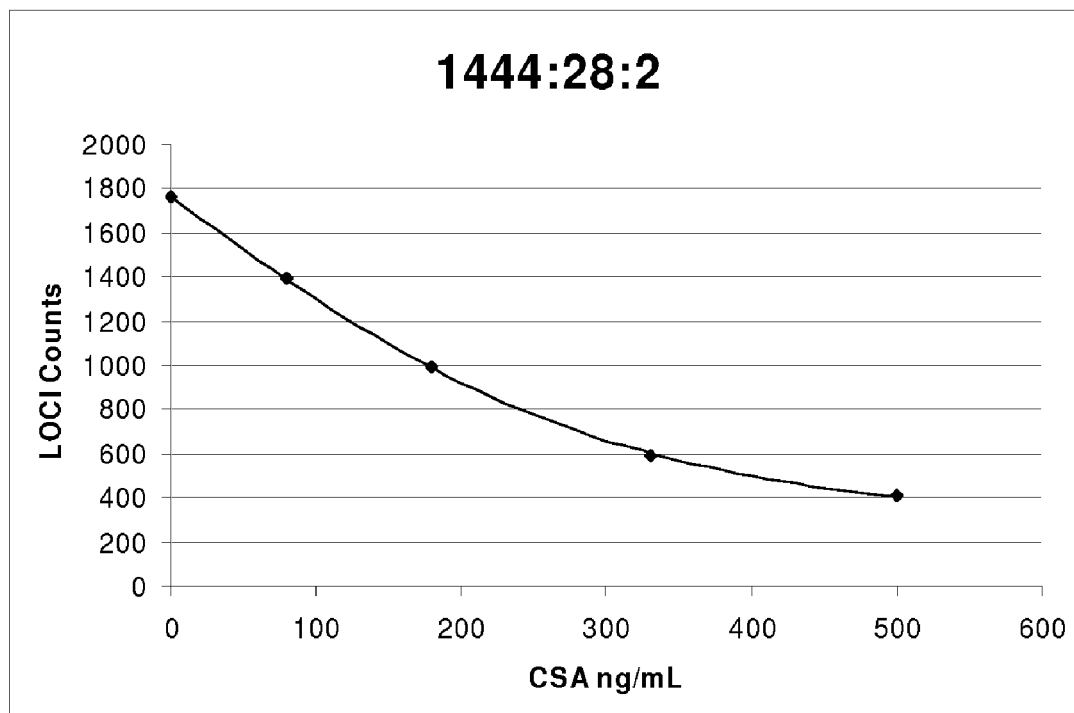
FIG. 26 is graphic depiction of the results of another assay for CsA conducted according to Format 1 of the present embodiments using the following reagents: CsA-DA-10-Hg-APRM chemiluminescent particles, antibody for CsA-biotin, and streptavidin-sensitizer particles.

Table 3 and FIG. 26 summarize the results wherein CsA-DA-10-Hg-APRM chemibead (11) was employed.

TABLE 3

| CsA-DA-10-Hg-APRM chemibead (11) | |
|---|---|
| Calibrator | LOCI Signal |
| 0.00 | 1759 |
| 80.00 | 1391 |
| 180.00 | 995 |
| 330.00 | 589 |
| 500.00 | 411 |

Figure 27:
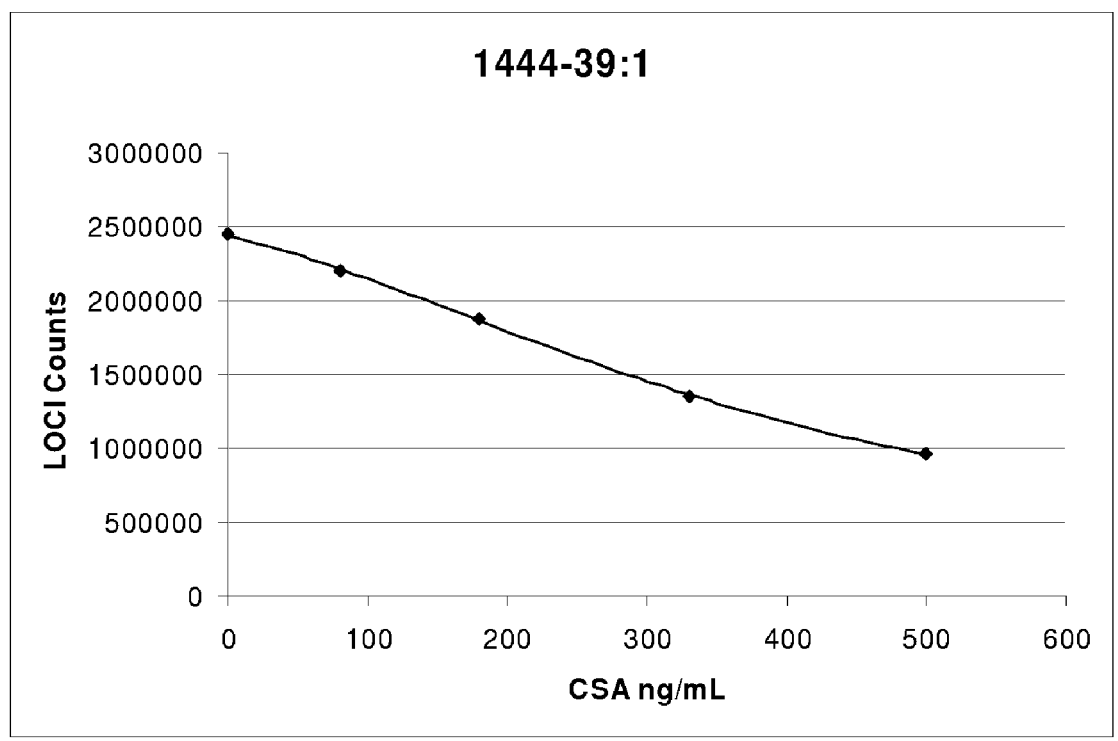
FIG. 27 is graphic depiction of the results of another assay for CsA conducted according to Format 1 of the present embodiments using the following reagents: CsA-DA-10-EPRM chemiluminescent particles, antibody for CsA-biotin, and streptavidin-sensitizer particles.

Table 4 and FIG. 27 summarize the results wherein CsA-DA-10-EPRM chemibead (9) was employed.

TABLE 4

| CsA-DA-10-EPRM chemibead (9) | |
|---|---|
| Calibrator | LOCI Signal |
| 0.00 | 2449 |
| 80.00 | 2198 |
| 180.00 | 1878 |
| 330.00 | 1353 |
| 500.00 | 958 |

As can be seen from the above data, a larger percentage difference between the signal for calibrator 1 (0.00 ng/mL CsA) and calibrator 2 (80.00 ng/mL CsA) is obtained with CsC-DA-10-EPRM chemibead (4) and CsC-DA-10-Hg-APRM chemibead (6) than with the CsA-chemibead reagents. This results in good sensitivity in the medical decision range as discussed above.

Format 2: In this embodiment of a method for determining the presence and/or amount of CsA in a medium suspected of containing CsA, a combination is provided in a medium wherein the combination comprises (i) the sample, (ii) a photosensitizer associated with a first particle and being capable of generating singlet oxygen wherein the first particle comprises a biotin-binding partner, (iii) a conjugate of cyclosporin A and biotin, and (iv) a chemiluminescent composition activatable by singlet oxygen and associated with a second particle wherein the second particle comprises an antibody for cyclosporin A. The combination is subjected to conditions for binding of cyclosporin A to the antibody for cyclosporin A. The photosensitizer is irradiated with light and the amount of luminescence generated by the chemiluminescent composition is detected, the presence and/or amount of luminescence being related to the amount of cyclosporin A in the sample.

For assays in accordance with Format 2 the following reagents discussed above were employed: streptavidin-photosensitizer beads (streptavidin sensibeads), CsA- or CsC-biotin and anti-CsA Mab-chemibeads (19). The samples were calibrators 1-5 as discussed above. The appropriate reagents and samples were added to a reaction vessel of the DIMENSION RxL analyzer as follows: Into the reaction vessel, 20 μL of anti-CSA (2G4) Mab-chemibeads was added followed by 20 μL of streptavidin sensibeads followed by 15 μL of water. Then, 10 μL of sample was added followed by 15 μL of water. The combination was incubated for 219 seconds and 20 μL CsA- or CsC-biotin was added followed by 150 μL of water. The combination was incubated for either 366 seconds or 713 seconds at a temperature of 37° C. Then, the combination was irradiated with light at 680 nM for a period of 0.2 to 1 second and the signal (in photon counts referred to as LOCI signal in the tables below) was read using a reader (Perkin-Elmer CPM Detector). The results are summarized below in Tables 5 and 6 and in FIGS. 28 and 29.

Figure 28:
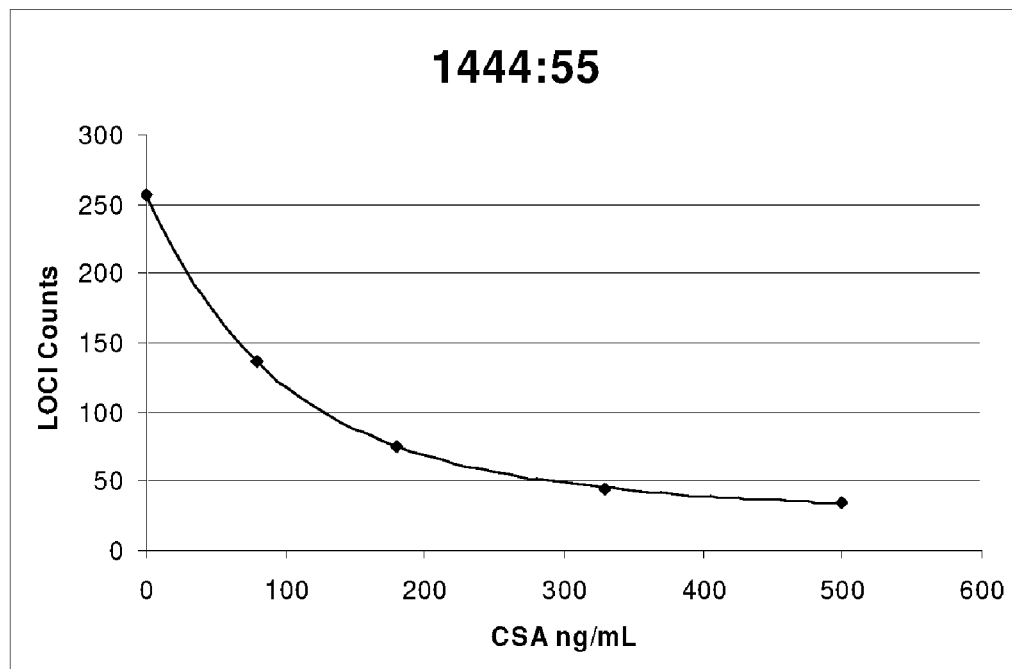
FIG. 28 is graphic depiction of the results of another assay for CsA conducted according to Format 2 of the present embodiments using the following reagents: antibody for CsA-chemiluminescent particles, CsA-biotin, and streptavidin-sensitizer particles.

Table 5 and FIG. 28 summarize the results wherein CsA-DA-10-BgG-biotin (20) was employed.

TABLE 5

| CsA-DA-10-BgG-biotin (20) | |
|---|---|
| Calibrator | LOCI Signal |
| 0.00 | 257 |
| 80.00 | 136 |
| 180.00 | 75 |
| 330.00 | 45 |
| 500.00 | 34 |

Figure 29:
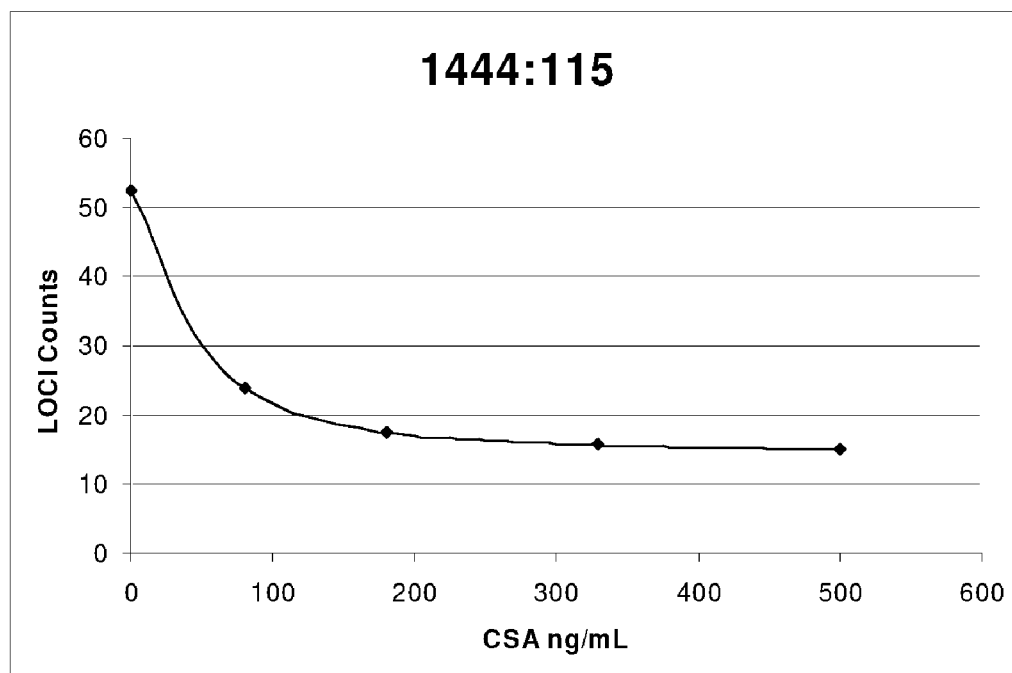
FIG. 29 is graphic depiction of the results of another assay for CsA conducted according to Format 2 of the present embodiments using the following reagents: antibody for CsA-chemiluminescent particles, CsA-DA-10-hG-BgG-biotin, and streptavidin-sensitizer particles.

Table 6 and FIG. 29 summarize the results wherein CsC-DA-10-BgG-biotin (33) was employed.

TABLE 6

| CsC-DA-10-BgG-biotin (33) | |
|---|---|
| Calibrator | LOCI Signal |
| 0.00 | 52 |
| 80.00 | 24 |
| 180.00 | 17 |
| 330.00 | 16 |
| 500.00 | 15 |

As can be seen from the above data, more signal and a larger difference between the signal for calibrator 1 (0.00 ng/mL CsA) and calibrator 2 (80.00 ng/mL CsA) is obtained with CsA-DA-10-BgG-biotin (20) than with CsC-DA-10-BgG-biotin (33). This results in good sensitivity in the medical decision range as discussed above.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A composition comprising cyclosporin A conjugated, at an amide nitrogen at position 7 or position 8, to bis-biotin by means of a linking group that has the formula:

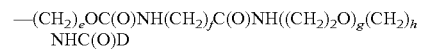

wherein D is

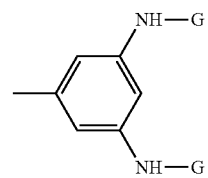

wherein G is $-C(O)(CH_2)_j NE-$, and
wherein e is 1 to 3, f is 1 to 3, g is 1 to 4, h is 1 to 3, and j is 1 to 6.

2. The composition according to claim 1 wherein e is 2, f is 1, g is 2, h is 2 and j is 5.

* * * * *